US009480733B2

(12) United States Patent
Ladner et al.

(10) Patent No.: US 9,480,733 B2
(45) Date of Patent: *Nov. 1, 2016

(54) PREVENTION AND REDUCTION OF BLOOD LOSS

(71) Applicant: DYAX CORP., Cambridge, MA (US)

(72) Inventors: Robert C. Ladner, Ijamsville, MD (US); Arthur C. Ley, Newton, MA (US); Shirish Hirani, Arlington, MA (US); Anthony Williams, Melrose, MA (US)

(73) Assignee: Dyax Corp., Burlington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/263,764

(22) Filed: Apr. 28, 2014

(65) Prior Publication Data

US 2014/0349940 A1 Nov. 27, 2014

Related U.S. Application Data

(63) Continuation of application No. 12/951,543, filed on Nov. 22, 2010, now Pat. No. 8,710,007, which is a continuation of application No. 11/929,729, filed on Oct. 30, 2007, now Pat. No. 8,124,586, which is a continuation of application No. 11/796,272, filed on Apr. 27, 2007, now abandoned, which is a continuation of application No. 11/322,960, filed on Dec. 30, 2005, now abandoned, which is a continuation of application No. 10/456,986, filed on Jun. 6, 2003, now Pat. No. 7,064,107.

(60) Provisional application No. 60/407,003, filed on Aug. 28, 2002, provisional application No. 60/387,239, filed on Jun. 7, 2002.

(51) Int. Cl.
| | |
|---|---|
| A61K 38/55 | (2006.01) |
| A61P 7/00 | (2006.01) |
| A61K 38/57 | (2006.01) |
| C12N 9/64 | (2006.01) |
| A61K 9/00 | (2006.01) |

(52) U.S. Cl.
CPC .............. *A61K 38/55* (2013.01); *A61K 38/57* (2013.01); *C12N 9/6445* (2013.01); *A61K 9/0019* (2013.01)

(58) Field of Classification Search
None
See application file for complete search history.

(56) References Cited

U.S. PATENT DOCUMENTS

| | | |
|---|---|---|
| 3,682,776 A | 8/1972 | Grundmann et al. |
| 3,691,016 A | 9/1972 | Patel |
| 3,969,287 A | 7/1976 | Jaworek et al. |
| 4,118,481 A | 10/1978 | Schnabel et al. |
| 4,153,687 A | 5/1979 | Schnabel et al. |
| 4,179,337 A | 12/1979 | Davis et al. |
| 4,195,128 A | 3/1980 | Hildebrand et al. |
| 4,229,537 A | 10/1980 | Hodgins |
| 4,247,642 A | 1/1981 | Hirohara et al. |
| 4,330,440 A | 5/1982 | Ayers et al. |
| 4,377,572 A | 3/1983 | Schwarz et al. |
| 4,399,216 A | 8/1983 | Axel et al. |
| 4,447,224 A | 5/1984 | DeCant |
| 4,447,233 A | 5/1984 | Mayfield |
| 4,595,674 A | 6/1986 | Tschesche et al. |
| 4,609,725 A | 9/1986 | Brady et al. |
| 4,634,665 A | 1/1987 | Axel et al. |
| 4,657,893 A | 4/1987 | Krantz et al. |
| 4,845,242 A | 7/1989 | Powers et al. |
| 4,881,175 A | 11/1989 | Ladner |
| 4,931,385 A | 6/1990 | Block et al. |
| 4,946,778 A | 8/1990 | Ladner et al. |
| 4,966,852 A | 10/1990 | Wun et al. |
| 5,106,833 A | 4/1992 | Broze et al. |
| 5,118,668 A | 6/1992 | Auerswald et al. |
| 5,166,133 A | 11/1992 | Houston et al. |
| 5,179,017 A | 1/1993 | Axel et al. |
| 5,212,091 A | 5/1993 | Diaz-Collier et al. |
| 5,223,409 A | 6/1993 | Ladner et al. |
| 5,260,203 A | 11/1993 | Ladner et al. |
| 5,278,144 A | 1/1994 | Wolf |
| 5,278,285 A | 1/1994 | Ebbers et al. |
| 5,312,736 A | 5/1994 | Rasmussen et al. |
| 5,372,933 A | 12/1994 | Zamarron et al. |
| 5,373,090 A | 12/1994 | Norris et al. |
| 5,378,614 A | 1/1995 | Petersen et al. |
| 5,407,915 A | 4/1995 | Fritz et al. |
| 5,409,895 A | 4/1995 | Morishita et al. |
| 5,426,224 A | 6/1995 | Lee et al. |

(Continued)

FOREIGN PATENT DOCUMENTS

| | | |
|---|---|---|
| CA | 2180950 A1 | 3/2005 |
| DE | 695 33 472 T2 | 1/2006 |

(Continued)

OTHER PUBLICATIONS

U.S. Appl. No. 10/016,329, filed Oct. 26, 2001, Markland.

(Continued)

*Primary Examiner* — Marsha Tsay
(74) *Attorney, Agent, or Firm* — Wolf, Greenfield & Sacks, P.C.

(57) ABSTRACT

Methods are described for preventing or reducing ischemia and/or systemic inflammatory response in a patient such as perioperative blood loss and/or systemic inflammatory response in a patient subjected to cardiothoracic surgery, e.g. coronary artery bypass grafting and other surgical procedures, especially when such procedures involve extra-corporeal circulation, such as cardiopulmonary bypass.

14 Claims, 4 Drawing Sheets

(56) References Cited

U.S. PATENT DOCUMENTS

| | | |
|---|---|---|
| 5,441,931 A | 8/1995 | Sprecher et al. |
| 5,444,156 A | 8/1995 | Veloso et al. |
| 5,446,090 A | 8/1995 | Harris |
| 5,455,338 A | 10/1995 | Sprecher et al. |
| 5,466,783 A | 11/1995 | Wun et al. |
| 5,563,123 A | 10/1996 | Innis et al. |
| 5,576,294 A | 11/1996 | Norris et al. |
| 5,583,107 A | 12/1996 | Wolf et al. |
| 5,585,089 A | 12/1996 | Queen et al. |
| 5,589,359 A | 12/1996 | Innis et al. |
| 5,618,696 A | 4/1997 | Norris et al. |
| 5,629,176 A | 5/1997 | Bjorn et al. |
| 5,635,187 A | 6/1997 | Bathurst et al. |
| 5,648,331 A | 7/1997 | Koudsi et al. |
| 5,663,143 A | 9/1997 | Ley et al. |
| 5,672,662 A | 9/1997 | Harris et al. |
| 5,677,146 A | 10/1997 | Sprecher et al. |
| 5,693,761 A | 12/1997 | Queen et al. |
| 5,693,762 A | 12/1997 | Queen et al. |
| 5,695,760 A | 12/1997 | Faanes et al. |
| 5,696,088 A | 12/1997 | Innis et al. |
| 5,719,041 A | 2/1998 | Lazarus et al. |
| 5,736,364 A | 4/1998 | Kelley et al. |
| 5,739,208 A | 4/1998 | Harris |
| 5,747,449 A | 5/1998 | Lasters et al. |
| 5,770,568 A | 6/1998 | Auerswald et al. |
| 5,780,265 A | 7/1998 | Dennis et al. |
| 5,786,328 A | 7/1998 | Dennis et al. |
| 5,795,865 A | 8/1998 | Markland et al. |
| 5,795,954 A | 8/1998 | Lazarus et al. |
| 5,800,385 A | 9/1998 | Demopulos et al. |
| 5,804,376 A | 9/1998 | Braxton et al. |
| 5,824,870 A | 10/1998 | Baszczynski et al. |
| 5,834,244 A | 11/1998 | Dennis et al. |
| 5,843,895 A | 12/1998 | Lazarus et al. |
| 5,849,992 A | 12/1998 | Meade et al. |
| 5,853,723 A | 12/1998 | Jacobs et al. |
| 5,863,893 A | 1/1999 | Dennis et al. |
| 5,869,637 A | 2/1999 | Au-Young et al. |
| 5,874,407 A | 2/1999 | Kelley et al. |
| 5,880,256 A | 3/1999 | Dennis et al. |
| 5,900,461 A | 5/1999 | Harris |
| 5,914,316 A | 6/1999 | Brown et al. |
| 5,932,462 A | 8/1999 | Harris et al. |
| 5,951,974 A | 9/1999 | Gilbert et al. |
| 5,962,266 A | 10/1999 | White et al. |
| 5,990,237 A | 11/1999 | Bentley et al. |
| 5,994,125 A | 11/1999 | Markland et al. |
| 6,001,596 A | 12/1999 | Hillman et al. |
| 6,004,579 A | 12/1999 | Bathurst et al. |
| 6,008,196 A | 12/1999 | Curran et al. |
| 6,010,880 A | 1/2000 | Markland et al. |
| 6,013,448 A | 1/2000 | Braxton et al. |
| 6,013,763 A | 1/2000 | Braisted et al. |
| 6,017,723 A | 1/2000 | Rao et al. |
| 6,057,287 A | 5/2000 | Markland et al. |
| 6,063,764 A | 5/2000 | Creasey et al. |
| 6,071,723 A | 6/2000 | Markland et al. |
| 6,087,473 A | 7/2000 | Conklin et al. |
| 6,090,916 A | 7/2000 | Vlasuk et al. |
| 6,103,499 A | 8/2000 | Markland et al. |
| 6,103,500 A | 8/2000 | Innis et al. |
| 6,113,896 A | 9/2000 | Lazarus et al. |
| 6,126,933 A | 10/2000 | Warne et al. |
| 6,159,938 A | 12/2000 | Gyorkos et al. |
| 6,171,587 B1 | 1/2001 | Wun et al. |
| 6,174,721 B1 | 1/2001 | Innis et al. |
| 6,180,607 B1 | 1/2001 | Davies et al. |
| 6,214,966 B1 | 4/2001 | Harris |
| 6,242,414 B1 | 6/2001 | Johnson et al. |
| 6,258,351 B1 | 7/2001 | Harris |
| 6,261,279 B1 | 7/2001 | Demopulos et al. |
| 6,306,884 B1 | 10/2001 | Buckman et al. |
| 6,333,402 B1 | 12/2001 | Markland et al. |
| 6,348,558 B1 | 2/2002 | Harris et al. |
| 6,362,254 B2 | 3/2002 | Harris et al. |
| 6,362,276 B1 | 3/2002 | Harris et al. |
| 6,376,604 B2 | 4/2002 | Kozlowski |
| 6,407,213 B1 | 6/2002 | Carter et al. |
| 6,413,507 B1 | 7/2002 | Bentley et al. |
| 6,423,498 B1 | 7/2002 | Markland et al. |
| 6,432,397 B1 | 8/2002 | Harris |
| 6,455,639 B1 | 9/2002 | Yasukohchi et al. |
| 6,472,195 B2 | 10/2002 | Hillman et al. |
| 6,515,100 B2 | 2/2003 | Harris |
| 6,534,276 B1 | 3/2003 | Wun et al. |
| 6,548,262 B2 | 4/2003 | Gentz et al. |
| 6,576,235 B1 | 6/2003 | Williams et al. |
| 6,583,108 B1 | 6/2003 | Tamburini et al. |
| 6,610,281 B2 | 8/2003 | Harris |
| 6,624,246 B2 | 9/2003 | Kozlowski |
| 6,664,331 B2 | 12/2003 | Harris et al. |
| 6,689,582 B1 | 2/2004 | Davies et al. |
| 6,710,125 B2 | 3/2004 | Kozlowski |
| 6,774,180 B2 | 8/2004 | Kozlowski et al. |
| 6,783,960 B2 | 8/2004 | Innis et al. |
| 6,783,965 B1 | 8/2004 | Sherman et al. |
| 6,806,360 B2 | 10/2004 | Wun et al. |
| 6,814,982 B2 | 11/2004 | Poncin et al. |
| 6,914,135 B2 | 7/2005 | Sheppard et al. |
| 6,953,674 B2 | 10/2005 | Markland et al. |
| 6,989,369 B2 | 1/2006 | Ladner et al. |
| 7,064,107 B2 | 6/2006 | Ladner et al. |
| 7,067,144 B2 | 6/2006 | Demopulos et al. |
| 7,078,383 B2 | 7/2006 | Ley et al. |
| 7,153,829 B2 | 12/2006 | Ladner et al. |
| 7,166,576 B2 | 1/2007 | Cicardi et al. |
| 7,235,530 B2 | 6/2007 | Blair et al. |
| 7,276,480 B1 | 10/2007 | Ladner et al. |
| 7,550,427 B2 | 6/2009 | Ley et al. |
| 7,628,983 B2 | 12/2009 | Markland et al. |
| 7,704,949 B2 | 4/2010 | Ladner et al. |
| 7,718,617 B2 | 5/2010 | Cicardi et al. |
| 7,811,991 B2 | 10/2010 | Ladner et al. |
| 7,851,442 B2 | 12/2010 | Ladner et al. |
| 7,919,462 B2 | 4/2011 | Markland et al. |
| 8,034,775 B2 | 10/2011 | Ladner et al. |
| 8,124,586 B2 | 2/2012 | Ladner et al. |
| 8,188,045 B2 | 5/2012 | Blair et al. |
| 8,283,321 B2 | 10/2012 | Markland et al. |
| 8,710,007 B2 | 4/2014 | Ladner et al. |
| 8,716,225 B2 | 5/2014 | Blair et al. |
| 8,828,703 B2 | 9/2014 | Ladner |
| 9,107,928 B2 | 8/2015 | Belichard |
| 9,114,144 B2 | 8/2015 | Ladner et al. |
| 2001/0027180 A1 | 10/2001 | Isaacs |
| 2002/0102703 A1 | 8/2002 | Sheppard et al. |
| 2002/0111460 A1 | 8/2002 | Holloway |
| 2003/0012969 A1 | 1/2003 | Clark |
| 2003/0096733 A1 | 5/2003 | Ny et al. |
| 2003/0100070 A1 | 5/2003 | Holloway |
| 2003/0113726 A1 | 6/2003 | Tsuchihashi et al. |
| 2003/0114372 A1 | 6/2003 | White et al. |
| 2003/0153046 A1 | 8/2003 | Jensen et al. |
| 2003/0175919 A1 | 9/2003 | Ley et al. |
| 2003/0223977 A1 | 12/2003 | Ley et al. |
| 2004/0038893 A1 | 2/2004 | Ladner et al. |
| 2004/0044075 A1 | 3/2004 | Staveski et al. |
| 2004/0049018 A1 | 3/2004 | Bailon et al. |
| 2004/0053206 A1 | 3/2004 | Cicardi et al. |
| 2004/0062746 A1 | 4/2004 | Martinez et al. |
| 2004/0062748 A1 | 4/2004 | Martinez et al. |
| 2004/0106747 A1 | 6/2004 | Bailon et al. |
| 2004/0126361 A1 | 7/2004 | Saifer et al. |
| 2004/0152633 A1 | 8/2004 | Jorgensen et al. |
| 2004/0171794 A1 | 9/2004 | Ladner et al. |
| 2004/0180827 A1 | 9/2004 | Chen et al. |
| 2004/0209243 A1 | 10/2004 | Nixon et al. |
| 2005/0004021 A1 | 1/2005 | Sprecher et al. |
| 2005/0075665 A1 | 4/2005 | Brenzel et al. |
| 2005/0089515 A1 | 4/2005 | Ley et al. |
| 2005/0164928 A1 | 7/2005 | Ladner et al. |
| 2005/0164945 A1 | 7/2005 | Nixon et al. |
| 2005/0180977 A1 | 8/2005 | Nixon et al. |

(56) References Cited

U.S. PATENT DOCUMENTS

| | | |
|---|---|---|
| 2006/0069020 A1 | 3/2006 | Blair et al. |
| 2006/0194727 A1 | 8/2006 | Ladner et al. |
| 2006/0205671 A1 | 9/2006 | Vinten-Johansen |
| 2006/0228331 A1 | 10/2006 | Peschke et al. |
| 2006/0264603 A1 | 11/2006 | Markland et al. |
| 2007/0020252 A1 | 1/2007 | Ladner et al. |
| 2007/0041959 A1 | 2/2007 | Ley et al. |
| 2007/0049522 A1 | 3/2007 | Ladner et al. |
| 2007/0065407 A1 | 3/2007 | Patten et al. |
| 2007/0079096 A1 | 4/2007 | Chen |
| 2007/0100133 A1 | 5/2007 | Beals et al. |
| 2007/0117752 A1 | 5/2007 | Larsen et al. |
| 2007/0213275 A1 | 9/2007 | Clark et al. |
| 2007/0249807 A1 | 10/2007 | Ladner et al. |
| 2007/0253949 A1 | 11/2007 | Golz et al. |
| 2007/0270344 A1 | 11/2007 | Belichard |
| 2008/0031426 A1 | 2/2008 | Weeks |
| 2008/0038276 A1 | 2/2008 | Sinha et al. |
| 2008/0050716 A1 | 2/2008 | Cicardi et al. |
| 2008/0064637 A1 | 3/2008 | Ladner et al. |
| 2008/0076712 A1 | 3/2008 | Ladner et al. |
| 2008/0131426 A1 | 6/2008 | Ladner et al. |
| 2008/0139473 A1 | 6/2008 | Ladner et al. |
| 2008/0152656 A1 | 6/2008 | Ladner et al. |
| 2008/0182283 A1 | 7/2008 | Markland et al. |
| 2008/0188409 A1 | 8/2008 | Blair et al. |
| 2008/0200646 A1 | 8/2008 | Ladner et al. |
| 2008/0221031 A1 | 9/2008 | Blair et al. |
| 2008/0226655 A1 | 9/2008 | Ladner et al. |
| 2008/0255025 A1 | 10/2008 | Ladner |
| 2008/0260752 A1 | 10/2008 | Ladner et al. |
| 2008/0299050 A1 | 12/2008 | Bortz et al. |
| 2009/0023651 A1 | 1/2009 | Markland et al. |
| 2009/0062195 A1 | 3/2009 | Ladner et al. |
| 2009/0075887 A1 | 3/2009 | McPherson |
| 2009/0082267 A1 | 3/2009 | Ladner et al. |
| 2009/0105142 A1 | 4/2009 | Moscicki |
| 2009/0117130 A1 | 5/2009 | Ladner et al. |
| 2009/0123475 A9 | 5/2009 | Siegel |
| 2009/0215119 A1 | 8/2009 | Ladner |
| 2009/0221480 A1 | 9/2009 | Blair et al. |
| 2009/0227494 A1 | 9/2009 | Blair et al. |
| 2009/0227495 A1 | 9/2009 | Blair et al. |
| 2009/0233852 A1 | 9/2009 | Blair et al. |
| 2009/0234009 A1 | 9/2009 | Blair et al. |
| 2009/0247452 A1 | 10/2009 | Ellis et al. |
| 2009/0247453 A1 | 10/2009 | Blair et al. |
| 2009/0264350 A1 | 10/2009 | Blair et al. |
| 2010/0034805 A1 | 2/2010 | Ladner et al. |
| 2010/0183625 A1 | 7/2010 | Sternlicht |
| 2010/0273721 A1 | 10/2010 | Belichard |
| 2010/0286061 A1 | 11/2010 | Devy et al. |
| 2011/0008762 A1 | 1/2011 | Cicardi et al. |
| 2011/0086801 A1 | 4/2011 | Ladner et al. |
| 2011/0136746 A1 | 6/2011 | Markland et al. |
| 2011/0172140 A1 | 7/2011 | Ley et al. |
| 2011/0200611 A1 | 8/2011 | Sexton |
| 2012/0015881 A1 | 1/2012 | Ladner et al. |
| 2012/0201756 A1 | 8/2012 | Sexton |
| 2012/0322744 A1 | 12/2012 | Ley et al. |
| 2012/0328517 A1 | 12/2012 | Markland et al. |
| 2013/0012438 A1 | 1/2013 | Blair et al. |
| 2014/0288001 A1 | 9/2014 | Blair et al. |
| 2015/0368359 A1 | 12/2015 | Belichard |

FOREIGN PATENT DOCUMENTS

| | | |
|---|---|---|
| EP | 0 132 732 A2 | 2/1985 |
| EP | 0 255 011 A2 | 2/1988 |
| EP | 0 274 826 A1 | 7/1988 |
| EP | 0 285 123 A2 | 10/1988 |
| EP | 0 301 122 A1 | 2/1989 |
| EP | 0 307 592 A2 | 3/1989 |
| EP | 0 318 451 A2 | 5/1989 |
| EP | 0 401 508 A2 | 12/1990 |
| EP | 0 486 001 A1 | 5/1992 |
| EP | 0 621 870 B1 | 5/1997 |
| EP | 0 621 871 B1 | 7/1997 |
| EP | 0 739 355 B1 | 9/2004 |
| EP | 1 484 339 A2 | 12/2004 |
| JP | 07-504891 T | 6/1995 |
| JP | 09-059838 A | 3/1997 |
| JP | 09-509048 | 9/1997 |
| JP | 09-511131 T | 11/1997 |
| JP | 10-503375 A | 3/1998 |
| JP | 10-510996 | 10/1998 |
| JP | 2002-524076 A | 8/2002 |
| JP | 2002-543147 | 12/2002 |
| WO | WO-89/10374 A1 | 11/1989 |
| WO | WO-90/02809 A1 | 3/1990 |
| WO | WO-92/06111 A1 | 4/1992 |
| WO | WO-93/09233 A2 | 5/1993 |
| WO | WO-93/14120 A1 | 7/1993 |
| WO | WO-93/14121 A1 | 7/1993 |
| WO | WO-93/14122 A1 | 7/1993 |
| WO | WO-95/18830 A2 | 7/1995 |
| WO | WO-95/21601 A2 | 8/1995 |
| WO | WO-95/23860 A3 | 9/1995 |
| WO | WO-96/04377 A1 | 2/1996 |
| WO | WO-96/04378 A3 | 2/1996 |
| WO | WO-96/20278 A2 | 7/1996 |
| WO | WO-96/35788 A2 | 11/1996 |
| WO | WO-97/33996 A2 | 9/1997 |
| WO | WO-98/52976 A1 | 11/1998 |
| WO | WO 99/21558 | 5/1999 |
| WO | WO-99/63090 A2 | 12/1999 |
| WO | WO-00/14235 A1 | 3/2000 |
| WO | WO-00/34317 A2 | 6/2000 |
| WO | WO-01/09968 A1 | 2/2001 |
| WO | WO-01/14424 A2 | 3/2001 |
| WO | WO-01/68707 A1 | 9/2001 |
| WO | WO-01/79480 A1 | 10/2001 |
| WO | WO-02/06334 A1 | 1/2002 |
| WO | WO-02/06539 A1 | 1/2002 |
| WO | WO 02/20569 | 3/2002 |
| WO | WO 02/30393 | 4/2002 |
| WO | WO-02/092147 A2 | 11/2002 |
| WO | WO-02/094200 A2 | 11/2002 |
| WO | WO-03/006860 A1 | 1/2003 |
| WO | WO-03/066824 A2 | 8/2003 |
| WO | WO-03/103475 A2 | 12/2003 |
| WO | WO-2004/019968 A1 | 3/2004 |
| WO | WO-2004/062646 A1 | 7/2004 |
| WO | WO-2004/062657 A | 7/2004 |
| WO | WO-2004/062689 A1 | 7/2004 |
| WO | WO-2005/021556 A2 | 3/2005 |
| WO | WO-2005/021557 A2 | 3/2005 |
| WO | WO-2005/075665 A2 | 8/2005 |
| WO | WO-2006/017538 A2 | 2/2006 |
| WO | WO-2006/036860 A2 | 4/2006 |
| WO | WO-2006/066878 A1 | 6/2006 |
| WO | WO-2006/089005 A2 | 8/2006 |
| WO | WO-2007/079096 A2 | 7/2007 |
| WO | WO-2007/106746 A2 | 9/2007 |
| WO | WO-2008/000833 A1 | 1/2008 |
| WO | WO-2009/026334 A2 | 2/2009 |
| WO | WO-2009/026539 A1 | 2/2009 |
| WO | WO-2009/102927 A1 | 8/2009 |
| WO | WO-2010/003475 A2 | 1/2010 |
| WO | WO-2010/006746 | 1/2010 |
| WO | WO-2011/085103 A2 | 7/2011 |
| WO | WO-2012/094587 A1 | 7/2012 |

OTHER PUBLICATIONS

U.S. Appl. No. 11/860,853, filed Sep. 25, 2007, Ladner et al.
U.S. Appl. No. 11/930,700, filed Oct. 31, 2007, Ladner et al.
U.S. Appl. No. 11/931,695, filed Oct. 31, 2007, Ladner.
U.S. Appl. No. 12/471,875, filed May 26, 2009, Ley et al.
U.S. Appl. No. 13/571,138, filed Aug. 9, 2012, Markland et al.
A.F. Williams; A.N. Barclay, Ann. Rev Immunol., 1988, vol. 6, pp. 381-405.

(56) References Cited

OTHER PUBLICATIONS

Abuchowski et al., "Alteration of Immunological Properties of Bovine Serum Albumin by Covalent Attachment of Polyethylene Glycol," J. Bio. Chem., 1977, vol. 252, pp. 3578-3581.
Abuchowski et al., "Cancer Therapy with Chemically Modified Enzymes, I., Antitumor Properties of Polyethylene Glycol-Asparaginase Conjugates," Cancer Biochem. Biophys., 1984, vol. 7, pp. 175-186.
Abuchowski et al., "Effect of Covalent Attachment of Polyethylene Glycol on Immunogenicity and Circulating Life of Bovine," J. Biol. Chem., 1977, vol. 252, pp. 3582-3586.
Adams et al: "The Role of Viscosupplementation with Hylan G-F 20 (Synvisc(R)) in the Treatment of Osteoarthritis of the Knee: a Canadian Multicenter Trial Comparing Hylan G-F 20 Alone, Hylan G-F 20 with Non-Steroidal Anti- Inflammatory Drugs (NSAIDs) and NSAIDs Alone", Osteoarthritis and Cartilage, Bailliere Tindall, London, GB, vol. 3, No. 4, pp. 213-225, (Dec. 1, 1995).
Adelman, et al., Proteolysis of Platelet Glycoprotein Ib by Plasmin Is Facilitated by Plasmin Lysine-Binding Regions. Blood, vol. 68 (6): 1280-1284, (Dec. 1986).
Albrecht, et al., Elastase Inhibition by the Inter-a-Trypsin Inhibitor and Derived Inhibitors of Man and Cattle, Hoppe-Seyler's Z. Physiol. Chem., vol. 364: 1703-1708, (Dec. 1983).
Albrecht, et al., Kunitz-Type Proteinase Inhibitors Derived by Limited Proteolysis of the Inter-a-Trypsin Inhibitors From several Mammalian Sera, Hoppe-Seyler's Z. Physiol. Chem., vol. 364: 1697-1702, (Dec. 1983).
Altschul et al., "Gapped BLAST and PSI-BLAST: a New Generation of Protein Database Search Programs," Nucleic Acids Research, 1997, vol. 25, pp. 3389-3402, Oxford University Press.
Anba, et al., Improving the Stability of a Foreign Protein in the Periplasmic Space of Escherichia coli, Biochimie, vol. 70(6): 727-733, (1988).
Angliker, et al., The Synthesis of Lysylflouromethanes and their Properties as Inhibitors of Trypsin, Plasmin and Cathepsin B, Biochemistry, 241:871-875, (1987).
Appendix A—alignment of SEQ ID No. 23 (DX-890) and SEQ ID No. 12 (IT102), 1 page, Jun. 27, 2007.
Asano M. et al., "Effects of a Nonpeptide Bradykinin B2 Receptor Antagonist, FR167344, on Different in Vivo Animal Models of Inflammation", Br J Pharmacol, vol. 122, p. 1436-1440 (1997).
Asano M. et al., Br J Pharmacol, vol. 122, p. 1436-1440 (1997).
Atherton, et al., Peptide Synthesis. Part 2. Procedures for Solid Phase Synthesis using Na-Fluorenylmethycarbonylamino-acids on Polyamide Supports. Synthesis of Substance P and of Acyl Carrier Protein 65-74 Decapeptide, J. Chem. Soc. Perkins Trans, 1:538-546, (1981).
Attwood, The Babel of Bioinformatics; Science, vol. 290, pp. 471-473 (2000).
Auerswald et al., Expression, Isolation and Characterization of Recombinant [Arg15, Glu52] Aprotinin, Bio. Chem. Hoppe-Seyler, 369:(Suppl)27-35 (1988).
Baba, M et al., States of Tyrosyl Residues and Circular Dichroism of Kunitz Trypsin Inhibitor, J. BIOCHEM 65 (1):113-121 (1969).
Balduyck, et al., Human Urinary Proteinase Inhibitor: Inhibitory Properties and Interaction with Bovine Trypsin, Bio. Chem. Hoppe-Seyler, vol. 366: 9-14, (1985).
Baneyx et al., Construction and Characterization of Escherichia coli Strains Deficient in Multiple Secreted Proteases: Protease III Degrades High-Molecular-Weight Substrates In Vivo, J Bacteriol., 173:2696-2703 (1991).
Baneyx et al., "In Vivo Degradation of Secreted Fusion Proteins by the Escherichia coli Outer Membrane Protease OmpT", J. Bacteriol., 172:491-494, (1990).
Basu et al., "Structure-Function Engineering of Interferon-b-1 b for Improving Stability, Solubility, Potency, Immunogenicity, and Pharmacokinetic Properties by Site-Selective Mono-PEGylation," Bioconjugate Chemistry, 2006, vol. 17, pp. 618-630.
Bayes et al., "Gateways to Clinical Trials" Methods Find Exp. Clin. Pharmacol., vol. 28(3): pp. 185-206 (2006).

Beckmann et al., "Preparation of Chemically 'Mutated' Aprotinin Homologues by Semisynthesis-P1 Substitutions Change Inhibitory Specificity," Eur. J. Biochem., vol. 176, pp. 675-682 (1988).
Berge, S.M., et al., "Pharmaceutical Salts", J. Pharm. Sci. 66:1-19 (1977).
Bergthorsdotiir et al., "Signals that Initiate Somatic Hypermutation of B Cell in Vitro", J. Immunol., p. 166:2228 (2001).
Berndt, et al.,"Designed Replacement of an Internal Hydration Water Molecule in BPTI: Structural and Functional Implications of a Glycine-to-Serine Mutation," Biochemistry, 32: 4564-4570 (1993).
Bhoola et al., "Bioregulation of Kinins: Kallikreins, Kininogens and Kininases," Pharmacological Reviews, 44 :1-80 (1992).
Blaber et al., "Targeting Kallikrein 6-Proteolysis Attenuates CNS Inflammatory Disease," The FASEB Journal, express article published online Mar. 19, 2004.
Blijlevens et al: "Palifermin (Recombinant Keratinocyte Growth Factor-1 ): a Pleiotropic Growth Factor with Multiple Biological Activities in Preventing Chemotherapy- and rAdiotherapy-Induced Mucositis", Annals of Oncology, vol. 18, No. 5, Jan. 1, 2007, pp. 817-826.
Bork, "Powers and Pitfalls in Sequence Analysis: the 70% Hurdle," Genome Research, vol. 10, pp. 398-400 (2000).
Borregaard et al., "Granules of the Human Neutrophilic Polymorphonuclear Leukocyte," Blood, 1997, vol. 89, No. 10, pp. 3503-3521.
Bowdish K, et. al., "Yeast Expression of a Catalytic Antibody with Chorismate Mutase Activity.", J Biol Chem.; 266 (18):11901-8 (Jun. 25, 1991).
Branden et al., "Prediction, Engineering, and Design of Protein," Introduction to Protein Structure, 1991, pp. 247, Garland Publishing Inc., New York.
Brenner, "Errors in Genome Annotation," Trends in Genetics, vol. 15, No. 4, pp. 132-133 (1999).
Brinkmann et al., "Design of an Aprotinin Variant with Inhibitory Activity Against Chymotrypsin and Cathepsin G by Recombinant DNA Technology," Biol. Chem. Hoppe-Seyler, vol. 371, pp. 43-52 (1990).
Browne et al., "Expression of Recombinant Human Plasminogen and Aglycoplasminogen in HeLa Cells," GeneBank, Accession No. M74220 (1991).
Broze et al., "Regulation of Coagulation by a Multivalent Kunitz-Type Inhibitor," Biochemistry, 29:7539-7546, (1990).
Brus et al., "Disease Severity Is Correlated with Plasma Clotting and Fibrinolytic and Kinin-Kallikrein Activity in Neonatal Respiratory Distress Syndrome," Pediatric Research, 41 :120-127, (1997).
Buchan et al., "A New Model of Temporary Focal Neocortical Ischemia in the Rat", Stroke 23 (2): 273-9 (1992).
Budavari, ed., Merck index, 11th ed., ISBN 911910-28-X, entries 923, 1745, 2740, 7425, (1989).
Burrage et al., "Matrix Metalloproteinases: Role in Arthritis," Frontiers in Bioscience, 2006, vol. 11, pp. 529-543.
Cantor, J.O., et al., "Elastin and Elastases in Lung Disease", Elastin and Elastases, Chapter 16, vol. 11, pp. 159-168 (1989).
Carey et al., Advanced Organic Chemistry, 3rd Edition, Part B: Reactions and Synthesis, Plenum Press, New York: 678-686 (1990).
Carlson et al., "The Determination of Recombinant Human Tissue-Type Plasminogen Activator Activity by Turbidimetry Using a Microcentrigual Analyzer," Anal. Biochem., 1988, vol. 168, pp. 428-435.
Carmichael, "Rodent Models oF Focal Stroke: Size, Mechanism, and Purpose", NeuroRx 2: 396-409 (2005).
Carpenter et al., "Rational Design of Stable Lyophilized Protein Formulations: Theory and Practice," Pharmaceutical Biotechnology, vol. 13, pp. 109-133 (2002).
Casati et al., "Cardiopulmonary Support and Physiology—Tranexamic Acid Compared with High-Dose Aprotinin in Primary Elective Heart Operations: Effects on Perioperative Bleeding and Allogeneic Transfusions," The Journal of Thoracic and Cardiovascular Surgery, vol. 120, pp. 520-527 (2000).
Cassim et al., "Kallikrein Cascade and Cytokines in Inflamed Joints," Pharmacology and Therapeutics, 2002, vol. 94, pp. 1-34.

(56) References Cited

OTHER PUBLICATIONS

Cernak, "Animal Models of Head Trauma", NeuroRx. 2(3): 410-422 (2005).
Chen et al., "A Model of Focal Ischemic Stroke in the Rat: Reproducible Extensive Cortical Infarction", Stroke 17 (4): 738-43 (1986).
Chen et al., "Establishment of an Animal Model of Oral Mucositis Induced by Conditioning Regimen of Hematopoietic Stem Cell Transplantation" Zhonghua Kou Qiang Yi Xue Za Zhi. 42(11 ):672-6 (2007). (Abstract only).
Chen et al., Solution Structure of a Kunitz-type Chymotrypsin Inhibitor Isolated from the Elapid Snake Bungarus Fasciatus, J. Biological Chemistry 276:45079-45087 (2001).
Chen, et al. "Refined 2-5 A X-ray Crystal Structure of the Complex Formed by Porcine Kallikrein A and the Bovine Pancreatic Trypsin Inhibitor—Crystallization, Patterson Search, Structure Determination, Refinement, Structure and Comparison with its Components and with the Bovine Trypsin-Pancreatic Trypsin Inhibitor Complex" J. Mol. Biol. vol. 164, pp. 283-311 (1983).
Chothia, Cyrus et al., "Canoical Structures for the Hypervariable Regions of Immunoglobins" J. Mol. Biol., (1987), vol. 196, pp. 901-917.
Chung et al., "Human Plasma Prekallikrein, a Zumogen to a Serine Protease that Contains Four Tandem Repeats," GenBank, Accession #P03952 (1986).
Churg et al., "Proteases and Emphysema," Curr. Opin. Pulm. Med., 2005, vol. 11, pp. 153-159.
Colman et al., "Activation of the Kallikrein-Kinin System in Arthritis and Enterocolitis in Genetically Susceptible Rats: Modulation by a Selective Plasma Kallikrein Inhibitor," Proc. Assoc. Am. Physicians, 109:10-22 (1997).
Colman et al., Hemostasis and Thrombosis Basic Principles and Clinical Practice, Chapter 1, 2nd Edition, 3-17 (1987).
Colman et al., "The Plasma Kallikrein-Kinin System in Sepsis, Inflammatory Arthritis, and Enterocolitis" Clinical Reviews in Allergy and Immunology, vol. 16, pp. 365-384 (1998).
Colman R. W., "Plasma and Tissue Kallikrein in Arthritis and Inflammatory Bowel Disease", Immunopharmacology, Jan. 1, 1999, pp. 103-108, vol. 43, No. 2/03, Elsevier Science Publishers, BV.
Colman, et al., "Contact System: A Vascular Biology Modulator With Anticoagulant, Profibrinolytic, Antiadhesive, and Proinflammatory Attributes" Blood, 90, 3819-3843 (1997).
Colman., "Plasma and Tissue Kallikrein in Arthritis and Inflammatory Bowel Disease" Immunopharmacology, vol. 43, pp. 103-108 (1999).
Communication from the European Patent Office for EP Application No. 10180484.7 (105493-0254) dated Dec. 11, 2013, 3 pages.
Communication received in EP Patent Application 03791557.6, dated Nov. 20, 2008.
Communication received in EP Patent No. 1 484 339 (App. No. 04019920.0), dated Sep. 29, 2005.
Corpet et al., "Recent Improvements of the ProDom Database of Protein Domain Families," Nucl. Acids Res., 1999, vol. 27, pp. 263-267.
Cumming et al., "Hemodynamic, Renal, and Hormonal Aprotinin in an Ovine Model of Septic Shock," Critical Care Medicine, 20:1134-1139 (1992).
Cunningham et al., "Structural and Functional Characterization of Tissue Factor Pathway Inhibitor Following Degradation by Matrix Metalloproteinase-8," Biochem. J., 2002, vol. 367, pp. 451-458.
Currie, B. "Design and Synthesis of a Bicyclic Non-Peptide β-Bend Mimetic of Enkephalin," Tetrahedron, 49:3489-3500 (1993).
De Campos, et al., "Antioedematogenic and Antinociceptive Actions of NPC 18521, a Novel Bradykinin B2 Receptor Antagonist", Eur J Pharmacol316, 277-286 (1996).
De Haard, et al. "A Large Non-Immunized Human Fab Fragment Phage Library that Permits Rapid Isolation and Kinetic Analysis of High Affinity Antibodies". J. Biol. Chem 274:18218-30, (1999).

De Wildt, et al. "Antibody Arrays for High-Throughput Screening of Antibody-Antigen Interactions", Nat. Biotechnol. 18:989-994 (2000).
De Wildt, et al., "Characterization of Human Variable Domain Antibody Fragments Against the U1 RNA-Associated A Protein, Selected from a Synthetic and Patient-Derived Combinatorial V Gene Library" Eur J Immunol. 26(3):629-39 (1996).
Debiopharm Brochure, "Engineered Protein Inhibitor of Human Neutrophil Elastase EPIO-hNE4 (DX-890)," Dated Oct. 2004, printed from www.debio.com/e/pdf/fiche_epi_hne4_e.pdf.
Dela Cadena et al., "Role of Kallikrein-Kinin System in the Pathogenesis of Bacterial Cell Wall-Induced Inflammation and Enterocolitis," Transact. Assoc. Am. Physicians, 105:229-237 (1992).
Dela Cadena, et al., "Inhibition of Plasma Kallikrein Prevents Peptidoglycan-Induced Arthritis in the Lewis Rat," FASEB Journal, 9:446-452 (1995).
Delacourt et al., "Protection Against Acute Lung Injury by Intravenous or Intratracheal Pretreatment with EPI-HNE-4, a New Potent Neutrophil Elastase Inhibitor," Am. J. Respir. Cell Mol. Biol., Mar. 26, 2002, vol. 26, No. 3, pp. 290-297.
Delaria et al., "Characterization of Placental Bikunin, a Novel Human Serine Protease Inhibitor," J. Biological Chemistry, May 2, 1997, vol. 272, No. 18, pp. 12209-12214.
Delgado et al., "The Uses and Properties of PEG-Linked Proteins," Critical Review in Therapeutic Drug Carrier Systems, 1992, vol. 9, No. 3,4, pp. 249-304.
Deng, et. al., "Production of Recombinant Humanized Anti-HBsAg Fab Antibody by Fermentation" Sheng Wu Gong Cheng Xue Bao, 20(5):800-4 (Sep. 2004) (Abstract Only).
Dennis & Lazarus, "Kunitz Domain Inhibitors of Tissue Factor-Factor Vlla (I. Potent Inhibitors Selected from Libraries by Phage Display)," Journal of Biological Chemistry 269:22129-22136 (1994).
Dennis & Lazarus, "Kunitz Domain Inhibitors of Tissue Factor-Factor Vlla (II. Potent and Specific Inhibitors by Competitive Phage Selection)," Journal of Biological Chemistry, 269:22137-22144 (1994).
Dennis et al., "Potent and Selective Kunitz Domain Inhibitors of Plasma Kallikrein Designed by Phage Display," J. Biol. Chem., 270:25411-25417 (1995).
Devani et al., "Kallikrein-Kinin System in Inflammatory Bowel Disease: Intestinal Involvement and Correlation with the Degree of Tissue Inflammation," Digestive and Liver Disease, 2005, vol. 37, pp. 665-673.
Dhalluin et al., "Structural, Kinetic, and Thermodynamic Analysis of the Binding of the 40kDa PEG-interferon-a-2a and its Individual Positional Isomers to the Extracellular Domain of the Receptor IFNAR2," Bioconjugate Chemistry, 2005, vol. 16, pp. 518-527.
Diaz et al., "The Design of Water Soluble β-Sheet Structure Based on a Nucleation Strategy," Tetrahedron, 49:3533-3534 (1993).
Dimaio et al., "A New Class of Potent Thrombin Inhibitors That Incorporates a Scissile Pseudopeptide Bond," FEBS Lett., 282(1):47-52 (1991).
Dittmar et al., "External Carotid Artery Territory Ischemia Impairs Outcome in the Endovascular Filament Model of Middle Cerebral Artery Occlusion in Rats" Stroke 34: 2252-7 (2003).
Dittmar et al.. "Fischer-344 Rats are Unsuitable for the MCAO Filament Model Due to Their Cerebrovascular Anatomy" J Neurosci Methods 156: 50 (2006).
Doerks, et al., "Protein Annotation: Detective Work for Function Prediction", Trends in Genetics, vol. 14 (6), pp. 248-250. (1998).
Donnelly et al., "Therapy for Chronic Obstructive Pulmonary Disease in the 21st Century," Drugs, 2003, vol. 63, pp. 1973-1998.
Dragosits, el. al., "The Response to Unfolded Protein is Involved in Osmotolerance of *Pichia pastoris*" BMC Genomics. Mar. 26, 2010;11 :207.
Dufton, "Proteinase Inhibitors and Dendrotoxins," Eur. J. Biochem., vol. 153, pp. 647-654. (1985).
Eigenbrot et al. "Structural Effects Induced by Removal of a Disulfide-Bridge: The X-ray Structure of the C30A/ C51A Mutant of Basic Pancreatic Trypsin Inhibitor at 1.6 A," Protein Engineering, 3:591-598 (1990).

(56) References Cited

OTHER PUBLICATIONS

Ellis et al., "The Urokinase Receptor: Involvement in Cell Surface Proteolysis and Cancer Invasion," Ann. NY. Acad. Sci., 667:13-31 (1992).
English Translation of Final Office Action for Japanese Application No. 2004-510605 (105493-0274) dated Apr. 28, 2010, 3 pages.
English Translation of Office Action for Japanese Application No. 2010-004265 (105493-0275) dated May 1, 2012, 3 pages.
English Translation of Office Action for Japanese Patent Application No. 2004-510605 (105493-0274) dated Jul. 10, 2009, 6 pages.
English Translation of Office Action for JP 2011-164650 (105493-0369) mailed Oct. 2, 2013, 5 pages.
English Translation of Official Action for Japanese Application No. 2007-533689 (105493-0368) dated Apr. 27, 2011, 6 pages.
English Translation of Official Action for Japanese Application No. 2007-533689 (105493-0368), mail date Nov. 18, 2011, 8 pages.
English Translation of Official Action for Japanese Application No. 2007-533689 (105493-0368), mail date Sep. 18, 2012, 5 pages.
English Translation of Official Action for Japanese Application No. 2011-164650 (105493-0369), mail date Mar. 21, 2013, 5 pages.
English Translation of Official Action for Japanese Application No. 2012-242083 (105493-0448) dated May 26, 2014, 2 pages.
Enzon Pharmaceuticals, Macromolecular Engineering Technologies, 2004, pp. 1-14.
European Search Report for EP Application No. 07023364.8 (105493-0253), mail date Jun. 6, 2008, 7 pages.
European Search Report for EP Application No. 10180484.7 (105493-0254), mail date Mar. 9, 2011, 7 pages.
European Search Report for EP Application No. 10180486.2 (105493-0255), mail date Feb. 15, 2011, 6 pages.
Examination Report for Canadian Application No. 2581680 (105493-0365) dated Feb. 17, 2012, 5 pages.
Examination Report No. 1 for Australian Patent Application No. 2011201811 (105493-0239) dated Feb. 11, 2013, 7 pages.
Examination Report No. 2 on Australian Patent Application No. 2008202377 (105493-0238) dated Oct. 4, 2010, 2 pages.
Examination Report No. 2 on Australian Patent Application No. 2011201811 (105493-0239) dated Feb. 13, 2013, 3 pages.
Examiners First Report on Australian Patent Application No. 2003243394 (105493-0237) dated Sep. 6, 2006, 2 pages.
Examiners First Report on Australian Patent Application No. 2005289621 (105493-0363) dated Apr. 29, 2010, 2 pages.
Examiners First Report on Australian Patent Application No. 2008202377 (105493-0238) dated Aug. 12, 2009, 2 pages.
Examiners First Report on Australian Patent Application No. 2011218732 (105493-0364) dated Apr. 30, 2012, 1 page.
Examiners Report for Canadian Application No. 2488558 (105493-0243) dated Mar. 7, 2012, 2 pages.
Examiners Report for Canadian Application No. 2488558 (105493-0243) dated Nov. 12, 2010, 3 pages.
Examiners Report No. 2 on Australian Patent Application No. 2003243394 (105493-0237) dated Sep. 26, 2007, 3 pages.
Examiners Report No. 3 on Australian Patent Application No. 2008202377 (105493-0238) dated Jan. 31, 2011, 2 pages.
Extended European Search Report and Search Opinion from European Application No. 10180486.2 dated Feb. 9, 2011.
Extended European Search Report and Search Opinion from European Application No. 10180486.2 dated Feb. 23, 2011.
Extended European Search Report and Search Opinion from European Application No. 10180484.7, mail date Mar. 9, 2011.
Extended European Search Report and Search Opinion from European Application No. 08018863.4, mail date Apr. 1, 2009.
Extended European Search Report and Search Opinion from European Application No. 10164197.5 dated Oct. 1, 2010.
Extended European Search Report and Search Opinion from European Application No. 8798517.2 dated Oct. 26, 2010.
Extended European Search Report for EP Application No. 13174097.9 (105493-0491) dated Nov. 15, 2013, 16 pages.
Extended European Search Report from European Application No. 10 72 9465 dated Jan. 18, 2013.
Extended European Search Report from European Application Serial No. 07758271.6 dated Jun. 24, 2010.
Falquet et al., "The PROSITE Databse, its Status in 2002," Nucleic Acids Res., 2002, vol. 30, pp. 235-238.
Fidler & Ellis, "The Implications of Angiogenesis for the Biology and Chemistry of Cancer Metastasis," Cell, 79:185-188 (1994).
Fields & Noble, "Solid Phase Peptide Synthesis Utilizing 9-fluorenylmethocarbonyl Amino Acids," Int. J. Peptide Protein Research, 35:161-214 (1990).
Fife, et al, "Cartilage Matrix Glycoprotein is Present in Serum in Experimental Canine Osteoarthritis" J Clin Invest. 84(5): 1432-1439 (1989).
Final Office Action for U.S. Appl. No. 11/931,373 (105493-0232) dated Jan. 4, 2010, 14 pages.
Final Office Action for U.S. Appl. No. 10/456,986 (105493-0223) dated May 18, 2005, 9 pages.
Final Office Action for U.S. Appl. No. 11/804,388 (105493-0353) dated Nov. 17, 2011, 9 pages.
Final Office Action for U.S. Appl. No. 11/929,729 (105493-0228) dated Aug. 22, 2011, 7 pages.
Final Office Action for U.S. Appl. No. 12/951,543 (105493-0234) dated Jul. 18, 2013.
Final Office Action on U.S. Appl. No. 11/930,018 (105493-0230) dated Jan. 11, 2010, 12 pages.
Final Office Action on U.S. Appl. No. 13/228,300 (105493-0351) dated May 21, 2014, 9 pages.
Final Office Action on U.S. Appl. No. 13/458,086 (105493-0362) dated Aug. 7, 2013, 7 pages.
Fraedrich et al., "Reduction of Blood Transfusion Requirement in Open Heart Surgery by Administration of High Doses of Aprotinin-Preliminary Results," Thorac. Cardiovasc. Surg., 37:89-91 (1989).
Freidinger, et al., "Protected Lactam-Bridged Dipeptides for Use as Conformational Constraints in Peptides," Journal of Organic Chemistry, 47:104-109 (1982).
Fries et al., "Inter-a-inhibitor, Hyaluronan and Inflammation," Acta Biochimica Polonica, 2003, vol. 50, No. 3, pp. 735-742.
Frisbie, "An Animal Model for Venous Thrombosis and Spontaneous Pulmonary Embolism." Spinal Cord 43, 635-639 (2005).
G Yetkin et al: "The Healing Effect of TGF-[alpha] on Gastric Ulcer Induced by Acetylsalicylic Acid in Rats", International Journal of Pharmaceutics, vol. 277, No. 1-2, Jun. 1, 2004, pp. 163-172.
Galeffi, et. al., "Functional Expression of a Single-Chain Antibody to ErbB-2 in Plants and Cell-Free Systems" J Transl Med. Sep. 29, 2006;4:39.
Gardell, et al., "The Search for the Ideal Thrombolytic Agent: Maximize the Benefit and Minimize the Risk," Toxicologic Pathology, 21(2):190-198 (1993).
Gerriets et al., "Complications and Pitfalls in Rat Stroke Models for Middle Cerebral Artery Occlusion: a Comparison Between the Suture and the Macrosphere Model Using Magnetic Resonance Angiography", Stroke 35: 2372-2377 (2004).
Girard et al., "Functional Significance of the Kunitz-type Inhibitory Domains of Lipoprotein-Associated Coagulation Inhibitor," Nature, 338:518-520 (1989).
Girard et al., "Structure of the Human Lipoprotein-associated Coagulation Inhibitor Gene," J. Biol. Chem., 266:5036-5041 (1991).
Goldenberg et al., "Circular and Circularly Permuted Forms of Bovine Pancreatic Trypsin Inhibitor," J. Mol. Biol., vol. 165, pp. 407-413 (1983).
Gonzalez-Quevedo et al., The Synthetic Kunitz Domain Protein DX88 to Treat Angioedema in Patients with Hereditary Angioedema, International Immunopharmacology 2(9):1318 Abstract 205 (2002).
Goodson et al., "Site-directed PEGylation of recombinant interleukin-2 at its glycosylation site," Bio Technology, 1990, vol. 8, pp. 343-346.
Gouzy et al., "Whole Genome Protein Domain Analysis Using a New Method for Domain Clustering," Computers and Chemistry, 1999, vol. 23, pp. 333-340.
Graham et al., "Animal Models of Ischemic Stroke: Balancing Experimental Aims and Animal Care", Comp Med 54: 486-496 (2004).

(56) References Cited

OTHER PUBLICATIONS

Greilich et al., "Antifibrinolytic Therapy During Cardiopulmonary Bypass Reduces Proinflammatory Cytokine Levels: a Randomized, Double-Blind, Placebo-Controlled Study of x-aminocaproic Acid and Aprotinin," J. Thorac. Cardiovasc. Surg., 2003, vol. 126, pp. 1498-1503.
Gribskov et al., "Profile Analysis: Detection of Distantly Related Proteins," Proc. Natl. Acad. Sci. USA, 1987, vol. 84, pp. 4355-4358.
Gribskov et al., "Profile Analysis", Meth. Enzymol., 1990, vol. 183, pp. 146-159.
Grimaldi et al., "Trasylol in the Treatment of Acute Arthritis Due to Microcrystals," Reumatismo, vol. 23, No. 5, pp. 217-221, (1971) (Abstract only).
Gulberg et al., "Biosynthesis, Processing and Sorting of Neutrophil Proteins: Insight Into Neutrophil Granule Development," Eur. Journal of Hematology, 1997, vol. 58, pp. 137-153.
Guzman et al. "Mono-Iodoacetate-Induced Histologic Changes in Subchondral Bone and Articular Cartilage of Rat Femorotibial Joints: an Animal Model of Osteoarthritis." Toxicol Pathol. 31(6):619-24 (2003).
Hagihara et al., "Screening for Stable Mutants with Amino Acid Pairs Substituted for the Disulfide Bond Between Residues 14 and 38 of Bovine Pancreatic Trypsin Inhibitor (BPTI)," The Journal of Biological Chemistry, 2002, vol. 277, No. 52, pp. 51043-51048.
Han, Eun D. et al., Increased Vascular Permeability in C1 Inhibitor-Deficient Mice Mediated by the Bradykinin Type 2 Receptor, J. Clinical Investigation 109(8):1057-1063 (2002).
Han, Eun D. Reversal of the Increased Vascular Permeability in C1 Inhibitor Deficient Mice: Therapeutic Approaches, International Immunopharmacology 2(9):1315 Abstract 176 (2002).
Hanes et al., "Picomolar Affinity Antibodies from a Fully Synthetic Naive Library Selected and Evolved by Ribosome Display" Nat Biotechnol. 18:1287-92 (2000).
Herter et al., "Hepatocyte Growth Factor is a Preferred in Vitro Substrate for the Human Hepsin, a Membrane-Anchored Serine Protease Implicated in Prostate and Ovarian Cancers," Biochem. J., 2005, vol. 390, pp. 125-136.
Hoet, et al., "Generation of High-Affinity Human Antibodies by Combining Donor-Derived and Synthetic Complementarity-Determining-Region Diversity" Nat Biotechnol. 23(3)344-8 (2005).
Hoogenboom et al. "Natural and Designer Binding Sites Made by Phage Display Technology" Immunol Today 2:371-8 (2000).
Hoogenboom et al., "Antibody Phage Display Technology and its Applications" Immunotechnology 4:1-20 (1998).
Hoover et al., "Amino Acids of the Recombinant Kringle 1 Domain of Human Plasminogen That Stabilize Its Interaction with ω-Amino Acids," Biochemistry, 32: 10936-10943 (1993).
Hortin, et al., "Allosteric Changes in Thrombin's Activity Produced by peptides Corresponding to Segments of Natural Inhibitors and Substrates," The Journal of Biological Chemistry, 266:6866-6871 (1991).
Horwitz, et. al., "Secretion of Functional Antibody and Fab Fragment from Yeast Cells.", Proc Natl Acad Sci U S A. 85 (22):8678-82 (Nov. 1988).
Hostomsky, et al., "Solid Phase Assembly of Cow Colostrum Trypsin Inhibitor Gene," Nucleic Acids Research, 15:4849-4856 (1987).
Huang et al., "Kinetics of Factor Xa Inhibition by Tissue Factor Pathway Inhibitor," The Journal of Biological Chemistry, 1993, vol. 268, No. 36, pp. 26950-26955.
Huang et al., "Novel Peptide Inhibitors of Angiotensin-Converting Enzyme 2," The Journal of Biological Chemistry, 2003, vol. 278, No. 18, pp. 15532-15540.
Huge et al. "A Model to Investigate Postoperative Ileus with Strain Gauge Transducers in Awake Rats" J Surg Res. 74 (2):112-8 (1998). (Abstract Only).
Hwang I K et al: "Copper Chaperone for Cu,Zn-SOD Supplement Potentiates the Cu,Zn-SOD Function of Neuroprotective Effects Against Ischemic Neuronal Damage in the Gerbil Hippocampus", Free Radical Biology and Medicine, Elsevier Science, US, vol. 39, No. 3, Aug. 1, 2005, pp. 392-402.
Hynes et al., "X-Ray Crystal Structure of the Protease Inhibitor Domain of Alzheimer's Amyloid B-Protein Precursor," Biochemistry, 1990, vol. 29, pp. 10018-10022.
International Preliminary Examination Report for International Application No. PCT/US2003/017665 dated Mar. 30, 2005, 10 pages.
International Preliminary Report on Patentability for International Application No. PCT/US2005/034335 dated Mar. 3, 2009, 7 pages.
International Preliminary Report on Patentability from International Application No. PCT/US11/20377, mail date Jul. 19, 2012.
International Preliminary Report on Patentability from International Application No. PCT/US2008/073665, mail date Mar. 4, 2010.
International Preliminary Report on Patentability from International Application No. PCT/US2008/074061 dated Mar. 4, 2010.
International Search Report for Application No. PCT/US2003/017665 (105493-0293), mail date Jan. 6, 2005, 2 pages.
International Search Report from International Application No. PCT/US05/34335 dated Jul. 21, 2008.
International Search Report from International Application No. PCT/US07/63703 dated Dec. 21, 2007.
International Search Report from International Application No. PCT/US12/20470 dated Apr. 30, 2012.
International Search Report from International Application No. PCT/US2008/074061 dated Dec. 29, 2008.
International Search Report from International Application No. PCT/US2010/020257 dated Jun. 1, 2010.
International Search report from International Application No. PCT/US2004/028256 dated Jun. 22, 2005.
International Search Report from International Application No. PCT/US11/20377 dated Jun. 28, 2011.
International Search Report including Written Opinion from International Application No. PCT/08/73665 dated Feb. 5, 2008.
International Search Report of International Application No. PCT/US06/49322 mailed Dec. 7, 2007.
Invitation to Correct Deficiencies for EP Application No. 05799587.0 (105493-0366) dated Dec. 17, 2012, 1 page.
Kaplan, et. al., "A Prealbumin Activator of Preallirrein. 3. Appearance of Chemotactic Activity for Human Neutrophils by the Conversion of Human Prekallikrein", J. Exp. Med. vol. 135(1), p. 81-97; p. 92 Fig 10, p. 93 (1972).
Katre et al., "Chemical Modification of Recombinant Interleukin 2 by Polyethylene Glycol Increases its Potency in the Murine Meth a Sarcoma Model," PNAS USA, 1987, vol. 84, pp. 1487-1491.
Katre et al., "Immunogenicity of Recombinant IL-2 Modified by Covalent Attachment of Polyethylene Glycol," J. Immunol., 1990, vol. 144, pp. 209-213.
Kaufman, et al., "Amplification and Expression of Sequences Cotransfected with a Modular Dihydrofolate Reductase Complementary DNA Gene", Mol. Biol. 159:601 621 (1982).
Kelly et al., "Diabetes Insipidus in Uricase-Deficient Mice: a Model for Evaluating Therapy with Poly(ethylene glycol)-Modified," J. Am. Soc. Nephroi., 2001, vol. 12, pp. 1001-1009.
Kemp et al., "Synthesis of Peptide-Functionalized Daicylaminoepinodolidiones," Tetrahedron Letters, 29:5077-5080 (1988).
Kido et al., "Kunitz-Type Protease Inhibitor Found in Rat Mast Cells," J. Biol. Chem., 263:18104-18107 (1988).
Kido et al., "Protease Specificity of Kunitz Inhibitor Domain of Alzheimer's Disease Amyloid Protein Precursor," Biochemical and Biophysical Research Communications, 167:716-721 (1990).
Kirchhofer et al., "Hepsin Activates Pro-Hepatocyte Growth Factor and is Inhibited by Hepatocyte Growth Factor Activator-1 B (HAI-1B) and HAI-2," FEBS Letters, 2005, vol. 579, pp. 1945-1950.
Kirchhoff, et al., "A Major Human Epididymis-Specific cDNA Encodes a Protein with Sequence Homology to Extracellular Proteinase Inhibitors," Biology of Reproduction, 45:350-357 (1991).
Kline, et al., "Hirulog Peptides with Scissile Bond Replacements Resistant to Thrombin Cleavage," Biochem. Biophys. Res. Comm., 177:1049-1055 (1991).

(56) References Cited

OTHER PUBLICATIONS

Knappik et al., "Fully Synthetic Human Combinatorial Antibody Libraries (HuCAL) Based on Modular Consensus Frameworks and CDRs Randomized with Trinucleotides", J. Mol. Biol. 296:57-86 (2000).

Krogh et al., "Hidden Markov Models in Computational Biology," J. Mol. Biol., 1994, vol. 235, pp. 1501-1531.

Kuno et al., "Possible Involvement of Neutrophil Elastase in Impaired Mucosal Repair in Patients with Ulcerative Colitis," Journal of Gastroenterology, 2002, vol. 37, Supple XIV, pp. 22- 32.

Kurjan et al., "Structure of a Yeast Pheromone Gene (MFα): A Putative α-Factor Precursor Contains Four Tandem Copies of Mature α-Factor," Cell, (1982), vol. 30, pp. 933-943.

L. Bergamaschini et al: "Abstracts from the XXth International Complement Workshop: Abstract 16: Neuroprotective Effect of Plasma Kallikrein Inhibitor DX-88 on Brain Ischemia/Reperfusion Brain Injury", Molecular Immunology, vol. 41, No. 2-3, 16, Jun. 2004, pp. 201-333.

Laskowski, et al., "Inhibitors with Class-Specific Reactive Sites," Ann. Rev. Biochem., 49:593-626 (1980).

Leatherbarrow, et al., "Design of a Small Peptide-Based Proteinase Inhibitor by Modeling the Active-Site Region of Barley Chymotrypsin Inhibitor 2," Biochemistry, 30:10717-10721 (1991).

Leeb-Lundberg et al. "International Union of Pharmacology. XLV. Classification of the Kinin Receptor Family: from Molecular Mechanisms to Pathophysiological Consequences", (2005) Pharmacol Rev 57, 27-77.

Leonetti et al., "Increasing Immunogenicity of Antigens Fused to Ig-Binding Proteins by Cell Surface Targeting," The Journal of Immunology, 1998, vol. 160, pp. 3820-3827.

Levy Jerrold H et al: "The Therapeutic Potential of a Kallikrein Inhibitor for Treating Hereditary Angioedema.", Expert Opinion on Investigational Drugs Sep. 2006 LNKD-PUBMED:16916274,vol. 15, No. 9, Sep. 2006, pp. 1077-1090.

Ley et al., "Obtaining a Family of High-Affinity, High Specificity Protein Inhibitors of Plasmin and Plasma Kallikrein," Molecular Diversity, 2:119-124, (1996).

Lilla et al., "Active Plasma Kallikrein Localizes to Mast Cells and Regulates Epithelial Cell Apoptosis, Adipocyte Differentiation, and Stromal Remodeling During Mammary Gland Involution" J Biol Chem. 284(20):13792-13803 (2009).

Lohmann, et al., Plasmin- and Plasminogen-Activator Inhibitors after Excimer Laser Photorefractive Keratectomy: New Concept in Prevention of Postoperative Myopic Regression and Haze, Refractive and Corneal Surgery, 9:300-302, (1993).

Longa et al., "Reversible Middle Cerebral Artery Occlusion Without Craniectomy in Rats" Stroke 20 (1): 84-91 (1989).

Lucas, et al., "The Binding of Human Plasminogen to Fibrin and Fibrinogen," J. Biol. Chem., 258:4249-4256 (1983).

Lumry et al, Interim Results of EDEMA2, A Multicenter, Open-Label, Repeat-Dosing Study of Intravenous and Subcutaneous Administration of Ecallantide (DX-88) in Hereditary Angioedema. J. Allergy and Clinical Immunology 117(2)(Suppl. 1):S179 Abstract 699 (2006).

MacGilchrist et al., "Effect of the Serine Protease Inhibitor, Aprotinin, on Systemic Haemodynamics and Renal Function in Patients with Hepatic Cirrhosis and Ascites," Clin. Sci., 87:329-335 (1994).

Magklara et al., "Characterization of the Enzymatic Activity of Human Kallikrein 6: Autoactivation, Substrate Specificity and Regulation by Inhibitors," Biochem. Biophys. Res. Commun., Aug. 8, 2003, vol. 307, No. 4, pp. 948-955, Abstract Only.

Mann et al., Hemostasis and Thrombosis, Chapter 10, 2nd Edition, Basic Principles and Clinical Practice: 148-161 (1987).

Mannucci, "Hemostatic Drugs" New England Journal of Medicine, Drug Therapy, 339(4):245-253 (1998).

March, Jerry, Advanced Organic Chemistry, 3rd Edition, Reactions, Mechanisms, and Structure, John Wiley and Sons, New York: 396-398; 1057-1060; 1099-1100 (1985).

Markland et al., "Iterative Optimization of High-Affinity Protease Inhibitors Using Phage Display. 1. Plasmin," Biochemistry, 35:8045-8057 (1996).

Markland et al., "Selection for Protease Inhibitors Using Bacteriophage Display," Methods Enzymol., 267:28-51 (1996).

Markland et al., Iterative optimization of high-affinity protease inhibitors using phage display. 2. Plasma kallikrein and thrombin. Biochemistry. Jun. 18, 1996;35(24):8058-67.

Mathews, C.K., et al., Biochemistry, The Benjamin Cummins Publishing Co., Inc., Redwood City, CA.: pp. 208-212, (1990).

Mattheakis, Larry C. et al. "An in Vitro Polysome Display System for Identifying Ligands from Very Large Peptide Libraries" Proc. Natl. Acad. Sci. USA, (Sep. 1994), vol. 91, No. 19, pp. 9022-9026.

Maxfield et al., "Conformation of Poly(Ethylene Oxide) in the Solid State, Melt and Solution Measured by Raman scattering," Polymer, 1975, vol. 16, pp. 505-509.

McCarty, "Crystal-Induced Inflammation of the Joints," Annual Reviews of Medicine, vol. 21, pp. 357-366 (1970).

McConnell et al., "New Leupeptin Analogues: Synthesis and Inhibition Data," J. Med. Chem., 33:86-93 (1990).

Merriam-Webster reference for the term "prevent." web date: 2010. 2 pages.

Merrifield, B., "Solid Phase Synthesis," Science, 232:341-347 (1986).

Merrifield, R., "Solid Phase Peptide Synthesis. I. The Synthesis of a Tetrapeptide," J. Amer. Chem. Soc., 85:2149-2154 (1963).

Migliore, Alberto et al: "Open Pilot Study of Ultrasound-Guided Intra-Articular Injection of Hylan G-F 20 (Synvisc) in the Treatment of Symptomatic Hip Osteoarthritis", Clinical Rheumatology; Journal of the International League of Associations for Rheumatology, Springer-Verlag, LO, vol. 24, No. 3, pp. 285-289 (Jun. 1, 2005).

Mine et al., "Structural Mechanism for Heparin-Binding of the Third Kunitz Domain of Human Tissue Factor Pathway Inhibitor," Biochemistry, 2002, vol. 41, pp. 78-85.

Miyajima et al., "Secretion of Mature Mouse Interleukin-2 by *Saccharomyces cerevisiae*: Use of a General Secretion Vector Containing Promoter and Leader Sequences of the Mating Pheromone α-Factor," Gene, 37:155-161 (1985).

Molineux, Pegylation: "Engineering Improved Pharmaceuticals for Enhanced Therapy". Cancer Treatment Reviews, Apr. 2002. 28, Supplement A; 13-6.

Monteseirin. et al., "Plasma Kallikrein Amidolytic Activity in Bronchial Asthma," Allergol. Immunopathol., (Madr)., 20:211-214 (1992).

Moreland, "Intra-Articular Hyaluronan (Hyaluronic Acid) and Hylans for the Treatment of Osteoarthritis: Mechanisms of Action," Arthritis Res. Ther., 2003, vol. 5, pp. 54-67.

Murkin et al., "Aprotinin Significantly Decreases Bleeding and Transfusion Requirements in Patients Receiving Aspirin and Undergoing Cardiac Operations," J. Thorac. Cardiovasc. Surg., vol. 107, pp. 554-561 (1994).

Naess, et al., "Effects of a Combined Drug Regimen on Tumour Necrosis Factor and Plasma Kallikrein Activity in Experimental Endotoxaemia," Eur. J. Surg., 160:77-86 (1994).

Nagai and Sato, "Synthesis of a Bicyclic Dipeptide with the Shape of β-Turn Central Part ," Tetrahedron Lett., 26(5):647-650 (1985).

Nagai et al., "Bicyclic Turned Dipeptide (BTD) as a β-Turn Mimetic: its Design, Synthesis and Incorporation into Bioactive Peptides," Tetrahedron, 49:3577-3592 (1993).

Needleman; Wunsch, "A General Method Applicable to the Search for Similarities in the Amino Acid Sequence of Two Proteins". Mol. Biol., 1970, vol. 48, pp. 443-453.

Nektartm—Transforming Therapeutics, Nektar Advanced PEGylation: Polyethylene Glycol and Derivatives for Advanced PEGylation, pp. 1-24, catalogue 2004.

Nektartm—Transforming Therapeutics, Nektar Molecule Engineering: Polyethylene Glycol and Derivatives for Advanced PEGylation, pp. 1-20, catalogue-2003.

Neuhaus, et al., "Effect of Aprotinin on Intraoperative Bleeding and Fibrinolysis in Liver Transplantation," Lancet, 2: 924-925 (1989).

(56) References Cited

OTHER PUBLICATIONS

Ngo, et al., "Computational Complexity, Protein Structure Prediction, and the Levinthal Paradox", The Protein Folding Problem and Tertiary Structure Prediction, Chapter 14, pp. 433-440 and 492-495 only (1994).
Ning, el. al., "Production of Recombinant Humanized Anti-HBsAg Fab Fragment from *Pichia pastoris* by Fermentation.", J Biochem Mol Biol. ;38(3):294-9. (May 31, 2005).
NM_008455.2 (GI: 236465804): "Plasma Kallikrein Precursor", GenBank Record created on Dec. 29, 2010 GenBank [online] Bethesda, MD USA: United States National Library of Medicine, retrieved from internet using <URL: http://www.ncbi.nlm.nih.gov/nuccore/236465804?sat=14&satkey=4833839> GenBank Accession No. NM 008455.2 (GI: 236465804).
NM_012725.2 (GI:162138904): "Plasma Kallikrein Precursor", GenBank Record created on Dec. 26, 2010 GenBank [online] Bethesda, MD USA: United States National Library of Medicine, retrieved from internet using <URL: http://www.ncbi.nlm.nih.gov/nuccore/162138904?sat=14&satkey=5346361 > GenBank Accession No. NM_012725.2 (GI:162138904).
NOF Corporation, "PEG Derivatives, Phospholipid and Drug Delivery Materials for Pharmaceutical Products and Formulations," pp. 1-59, catalogue Ver. 8—Apr. 2006.
NOF Corporation, "PEG Derivatives, Phospholipid and Drug Delivery Materials for Pharmaceuticals," pp. 1-46, catalogue—2003, 1st.
NOF Corporation, "PEG Derivatives, Phospholipid and Drug Delivery Materials for Pharmaceuticals," pp. 1-50, catalogue—2003 2nd.
Non-Final Office Action for U.S. Appl. No. 11/931,635 (105493-0231) dated Nov. 12, 2008, 8 pages.
Non-Final Office Action for U.S. Appl. No. 10/456,986 (105493-0223) dated Oct. 21, 2004, 17 pages.
Non-Final Office Action for U.S. Appl. No. 10/953,902 (105493-0343) dated Dec. 14, 2005, 10 pages.
Non-Final Office Action for U.S. Appl. No. 11/125,639 (105493-0352) dated Jul. 5, 2006, 8 pages.
Non-Final Office Action for U.S. Appl. No. 11/322,960 (105493-0224) dated Oct. 31, 2006, 9 pages.
Non-Final Office Action for U.S. Appl. No. 11/323,261 (105493-0225) dated Aug. 2, 2006, 4 pages.
Non-Final Office Action for U.S. Appl. No. 11/323,261 (105493-0225) dated Dec. 26, 2006, 5 pages.
Non-Final Office Action for U.S. Appl. No. 11/323,261 (105493-0225) dated Mar. 22, 2007, 7 pages.
Non-Final Office Action for U.S. Appl. No. 11/466,979 (105493-0344) dated Dec. 5, 2008, 8 pages.
Non-Final Office Action for U.S. Appl. No. 11/466,979 (105493-0344) dated Jun. 12, 2008, 9 pages.
Non-Final Office Action for U.S. Appl. No. 11/796,272 (105493-0226) dated Feb. 2, 2009, 11 pages.
Non-Final Office Action for U.S. Appl. No. 11/796,272 (105493-0226) dated Jan. 13, 2010, 8 pages.
Non-Final Office Action for U.S. Appl. No. 11/804,388 (105493-0353) dated Dec. 8, 2009, 9 pages.
Non-Final Office Action for U.S. Appl. No. 11/804,388 (105493-0353) dated Jun. 10, 2011, 8 pages.
Non-Final Office Action for U.S. Appl. No. 11/804,388 (105493-0353) dated Jun. 15, 2010, 12 pages.
Non-Final Office Action for U.S. Appl. No. 11/860,853 (105493-0227) dated Apr. 17, 2009, 8 pages.
Non-Final Office Action for U.S. Appl. No. 11/929,685 (105493-0347) dated Dec. 2, 2008, 13 pages.
Non-Final Office Action for U.S. Appl. No. 11/929,729 (105493-0228) dated Aug. 26, 2009, 12 pages.
Non-Final Office Action for U.S. Appl. No. 11/929,729 (105493-0228) dated Dec. 29, 2010, 9 pages.
Non-Final Office Action for U.S. Appl. No. 11/929,729 (105493-0228) dated May 26, 2010, 9 pages.
Non-Final Office Action for U.S. Appl. No. 11/929,822 (105493-0346) dated Feb. 9, 2010, 6 pages.
Non-Final Office Action for U.S. Appl. No. 11/929,822 (105493-0346) dated Jan. 10, 2011, 5 pages.
Non-Final Office Action for U.S. Appl. No. 11/929,876 (105493-0345) dated Dec. 1, 2009, 10 pages.
Non-Final Office Action for U.S. Appl. No. 11/930,012 (105493-0229) dated Aug. 27, 2009, 9 pages.
Non-Final Office Action for U.S. Appl. No. 11/930,018 (105493-0230) dated Nov. 12, 2008, 14 pages.
Non-Final Office Action for U.S. Appl. No. 11/930,700 (105493-0348) dated Nov. 9, 2009, 8 pages.
Non-Final Office Action for U.S. Appl. No. 11/930,802 (105493-0349) dated Jan. 8, 2010, 9 pages.
Non-Final Office Action for U.S. Appl. No. 11/930,897 (105493-0350) dated Nov. 6, 2009, 9 pages.
Non-Final Office Action for U.S. Appl. No. 11/931,361 (105493-0357) dated Dec. 8, 2009, 8 pages.
Non-Final Office Action for U.S. Appl. No. 11/931,361 (105493-0357) dated Jun. 15 2010, 10 pages.
Non-Final Office Action for U.S. Appl. No. 11/931,373 (105493-0232) dated Jun. 12, 2009, 7 pages.
Non-Final Office Action for U.S. Appl. No. 11/931,373 (105493-0232) dated May 4, 2010, 11 pages.
Non-Final Office Action for U.S. Appl. No. 11/931,665 (105493-0355) dated Dec. 2, 2009, 10 pages.
Non-Final Office Action for U.S. Appl. No. 11/931,665 (105493-0355) dated Jun. 14, 2010, 12 pages.
Non-Final Office Action for U.S. Appl. No. 11/931,810 (105493-0354) dated Dec. 9, 2009, 10 pages.
Non-Final Office Action for U.S. Appl. No. 11/931,810 (105493-0354) dated Jul. 12, 2010, 17 pages.
Non-Final Office Action for U.S. Appl. No. 11/931,941 (105493-0361) dated Oct. 28, 2009, 8 pages.
Non-Final Office Action for U.S. Appl. No. 11/932,015 (105493-0359) dated Oct. 27, 2009, 7 pages.
Non-Final Office Action for U.S. Appl. No. 11/932,098 (105493-0358) dated Mar. 5, 2010, 12 pages.
Non-Final Office Action for U.S. Appl. No. 11/932,184 (105493-0360) dated Oct. 27, 2009, 8 pages.
Non-Final Office Action for U.S. Appl. No. 12/951,543 (105493-0234) dated Feb. 12, 2013, 10 pages.
Non-Final Office Action on U.S. Appl. No. 11/796,272 (105493-0226) dated Jul. 31, 2009, 11 pages.
Non-Final Office Action on U.S. Appl. No. 13/228,300 (105493-0351) dated Dec. 11, 2013, 12 pages.
Non-Final Office Action on U.S. Appl. No. 13/458,086 (105493-0362) dated Feb. 28, 2013, 15 pages.
Notice of Allowance for U.S. Appl. No. 10/456,986 (105493-0223) dated Dec. 21, 2005, 6 pages.
Notice of Allowance for U.S. Appl. No. 10/953,902 (105493-0343) dated May 31, 2006, 8 pages.
Notice of Allowance for U.S. Appl. No. 11/125,639 (105493-0352) dated Mar. 19, 2007, 6 pages.
Notice of Allowance for U.S. Appl. No. 11/323,261 (105493-0225) dated Jun. 27, 2007, 6 pages.
Notice of Allowance for U.S. Appl. No. 11/466,979 (105493-0344) dated Aug. 13, 2009, 7 pages.
Notice of Allowance for U.S. Appl. No. 11/466,979 (105493-0344) dated Dec. 4, 2009, 6 pages.
Notice of Allowance for U.S. Appl. No. 11/804,388 (105493-0353) dated Feb. 16, 2012, 8 pages.
Notice of Allowance for U.S. Appl. No. 11/929,729 (105493-0228) dated Dec. 21, 2011, 10 pages.
Notice of Allowance for U.S. Appl. No. 11/929,822 (105493-0346) dated Jun. 10, 2011, 9 pages.
Notice of Allowance for U.S. Appl. No. 11/930,012 (105493-0229) dated Jun. 3, 2010, 7 pages.
Notice of Allowance for U.S. Appl. No. 11/931,373 (105493-0232) dated Sep. 22, 2010, 13 pages.
Notice of Allowance for U.S. Appl. No. 12/951,543 (105493-0234) dated Dec. 12, 2013, 11 pages.

(56) References Cited

OTHER PUBLICATIONS

Notice of Allowance for U.S. Appl. No. 13/458,086 (105493-0362) dated Dec. 20, 2013, 8 pages.
Novotny et al., "Purification and Characterization of the Lipoprotein-Associated Coagulation Inhibitor from Human Plasma," J Biol. Chem., 264:18832-18837 (1989).
NP_000217.2 (GI:55956899): "Keratin, Type I Cytoskeletal 9", GenBank Record created on Dec. 27, 2010 GenBank [online] Bethesda, MD USA: United States National Library of Medicine, retrieved from internet using <URL: http://www.ncbi.nlm.nih.gov/protein/55956899?sat=14&satkey=4890700> GenBank Accession No. NP_000217.2 (GI:55956899).
NP_000418.2 (GI:109255251 ): "Loricrin", GenBank Record created on Nov. 3, 2010 GenBank [online] Bethesda, MD USA: United States National Library of Medicine, retrieved from internet using <URL:http://www.ncbi.nlm.nih.gov/ protein/109255251?sat=14&satkey=6156833> GenBank Accession No. NP_000418.2 (GI:109255251).
NP_000883.2 (GI: 78191798): "Plasma Kallikrein Preproprotein". GenBank Record created on Nov. 21, 2010, GenBank [online] Bethesda, MD USA: United States National Library of Medicine, retrieved from internet using <URL: http://www.ncbi.nlm.nih.gov/protein/78191798?sat=14&satkey=4530481> GenBank Accession No. NP_000883.2 (GI: 78191798).
NP_000892 (GI: 158508572): "Mineralocorticoid Receptor Isoform 1", GenBank Record created on Dec. 27, 2010, GenBank [online] Bethesda, MD USA: United States National Library of Medicine, retrieved from internet using <URL: http://www.ncbi.nlm.nih.gov/protein/158508572?sat=14&satkey=4536058> GenBank Accession No. NP_000892.2 (GI: 158508572).
NP_005850.1 (GI:5032007): "Transcriptional Activator Protein Pur-Alpha", GenBank Record created on Dec. 28, 2010, GenBank [online] Bethesda, MD USA: United States National Library of Medicine, retrieved from internet using <URL: http://www.ncbi.nlm.nih.gov/protein/5032007?sat=14&satkey=4526134> GenBank Accession No. NP_005850.1 (GI:5032007).
NP_006228.3 (GI:110347449): "POU Domain, Class 4, Transcription Factor 1", GenBank Record created on Dec. 27, 2010, GenBank [online] Bethesda, MD USA: United States National Library of Medicine, retrieved from internet using <URL:http://www.ncbi.nlm.nih.gov/protein/110347449?sat=14&satkey=4536081> GenBank Accession No. NP_006228.3 (GI:110347449).
NP_009060.2 (GI:22547197): "Zinc Finger Protein ZIC 2", GenBank Record created on Dec. 24, 2010, GenBank [online] Bethesda, MD USA: United States National Library of Medicine, retrieved from internet using <URL: http://www.ncbi.nlm.nih.gov/protein/22547197?sat=14&satkey=4290853> GenBank Accession No. NP_009060.2 (GI:22547197).
NP_031393.2 (GI:21396480): "RNA-Binding Protein Raly Isoform 2", GenBank Record created on Dec. 25, 2010, GenBank [online] Bethesda, MD USA: United States National Library of Medicine, retrieved from internet using <URL: http://www.ncbi.nlm.nih.gov/protein/21396480?sat=14&satkey=4835374> GenBank Accession No. NP_031393.2 (GI:21396480).
NP_032481.2 (GI: 236465805): "Plasma Kallikrein Precursor", GenBank Record created on Dec. 29, 2010 GenBank [online] Bethesda, MD USA: United States National Library of Medicine, retrieved from internet using <URL: http://www.ncbi.nlm.nih.gov/protein/236465805?sat=14&satkey=4833839> GenBank Accession No. NP_032481.2 (GI:236465805).
NP_036857.2 (GI:162138905): "Plasma Kallikrein Precursor", GenBank Record created on Dec. 26, 2010 GenBank [online] Bethesda, MD USA: United States National Library of Medicine, retrieved from internet using <URL: http://www.ncbi.nlm.nih.gov/protein/162138905?sat=14&satkey=5346361 > GenBank Accession No. NP_036857.2 (GI:162138905).
NP_056932.2 (GI:153791670): "Plasma Kallikrein Preproprotein", GenBank Record created on Dec. 27, 2010, GenBank [online] Bethesda, MD USA: United States National Library of Medicine, retrieved from internet using <URL: http://www.ncbi.nlm.nih.gov/protein/153791670?sat=14&satkey=4553701 > GenBank Accession No. NP_056932.2 (GI:153791670).
NP_061856.1 (GI:9506713): "H/ACA Ribonucleoprotein Complex Subunit 1", GenBank Record created on Dec. 24, 2010, GenBank [online] Bethesda, MD USA: United States National Library of Medicine, retrieved from internet using <URL: http://www.ncbi.nlm.nih.gov/protein/9506713?sat=14&satkey=4524138> GenBank Accession No. NP_061856.1 (GI:9506713).
NP_065104.1 (GI:9966841 ): "Cell Death Regulator Aven", GenBank Record created on Dec. 26, 2010, GenBank [online] Bethesda, MD USA: United States National Library of Medicine, retrieved from internet using <URL: http://www.ncbi.nlm.nih.gov/protein/9966841?sat=14&satkey=4843224> GenBank Accession No. NP_065104.1 (GI:9966841).
NP_115818.2 (GI:53829370): "Neuralized-Like Protein 4 Isoform 1", GenBank Record created on Dec. 27, 2010, GenBank [online] Bethesda, MD USA: United States National Library of Medicine, retrieved from internet using <URL: http://www.ncbi.nlm.nih.gov/protein/53829370?sat=14&satkey=4560911 > GenBank Accession No. NP_115818.2 (GI:53829370).
NP_476429.2 (GI:109148552): "Keratin, Type II Cytoskeletal 3", GenBank Record created on Dec. 24, 2010 GenBank [online] Bethesda, MD USA: United States National Library of Medicine, retrieved from internet using <URL: http://www.ncbi.nlm.nih.gov/protein/109148552?sat=14&satkey=6358709> GenBank Accession No. NP_NP_476429.2 (GI:109148552).
NP_631961.1 (GI:21327701): "TATA-Binding Protein-Associated Factor 2N Isoform 1", GenBank Record created on Dec. 25, 2010, GenBank [online] Bethesda, MD USA: United States National Library of Medicine, retrieved from internet using <URL: http://www.ncbi.nlm.nih.gov/protein/21327701 ?sat=14&satkey=4528109> GenBank Accession No. NP_631961.1 (GI:21327701 ).
NP_787059.2 (GI:40068462): "AT-Rich Interactive Domain-Containing Protein 1B Isoform 3", GenBank Record created on Mar. 4, 2010, GenBank [online] Bethesda, MD USA: United States National Library of Medicine, retrieved from internet using <URL: http://www.ncbi.nlm.nih.gov/protein/Np_787059.2?report=genpept> GenBank Accession No. NP_787059.2 (GI:40068462).
Nwariaku, et al., "Effect of a Bradykinin Antagonist on the Local Inflammatory Response Following Thermal Injury" Burns, 22:324-327 (1996).
Office Action for European Application No. 03757339.1 (105493-0252) dated Aug. 20, 2008, 5 pages.
Office Action for European Application No. 03757339.1 (105493-0252) dated Dec. 8, 2008, 4 pages.
Office Action for European Application No. 03757339.1 (105493-0252) dated May 11, 2009, 4 pages.
Office Action for European Application No. 07023364.8 (105493-0253) dated Mar. 18, 2010, 5 pages.
Office Action for European Application No. 10180484.7 (105493-0254) dated Feb. 16, 2012, 5 pages.
Office Action for European Application No. 10180486.2 (105493-0255) dated Dec. 17, 2013, 4 pages.
Office Action for European Application No. 10180486.2 (105493-0255) dated Feb. 16, 2012, 4 pages.
Office Action for European Application No. 10180486.2 (105493-0255) dated Nov. 3, 2014, 4 pages.
Official Action for Japanese Patent Application No. 2013-114068 (105493-0488) dated Jun. 25, 2014, 2 pages. (English translation not available).
Okamoto, et al., "A Finding of Highly Selective Synthetic Inhibitor of Plasma Kallikrein; Its Action to Bradykinin Generation, Intrinsic Coagulation and Experimental DIC," Agents Actions Suppl., 38(1):198-205 (1992).
O'Reilly et al., "Angiostatin: A Novel Angiogenesis Inhibitor That Mediates the Suppression of Metastases by a Lewis Lung Carcinoma," Cell, 79:315-328 (1994).
Pan et al., "Reperfusion Injury Following Cerebral Ischemia: Pathophysiology, MR Imaging, and Potential Therapies," Neuroradiology, 2007, vol. 49, pp. 93-102.

(56) References Cited

OTHER PUBLICATIONS

Park, et al., "Three Dimensional Structure of the Kringle Sequence: Structure of Prothrombin Fragment 1," Biochemistry, 25:3977-3982 (1986).
PCT International Search Report dated Jul. 21, 2008 and issued in PCT/US05/34335.
PCT Written Opinion dated Jul. 21, 2008 and issued in PCT/US05/34335.
Petersen et al., "Inhibitory Properties of Separate Recombinant Kunitz-Type-Protease-Inhibitor Domains from Tissue-Factor-Pathway Inhibitor," Eur. J. Biochem., 1996, vol. 235, pp. 310-316.
Phillips, "The Challenge of Gene Therapy and DNA Dellicery," J. Pharm. Pharmacology, vol. 53, pp. 1169-1174 (2001).
Pintigny et al., "Aprotinin Can Inhibit the Proteolytic Activity of Thrombin: a Fluorescence and an Enzymatic Study," Eur. J. Biochem., 1992, vol. 207, pp. 89-95.
Piro et al., "Role for the Kunitz-3 Domain of Tissue Factor Pathway Inhibitor-A in Cell Surface Binding," Circulation, 2004, vol. 110, pp. 3567-3572.
Pirollo et al.. "Targeted Delivery of Small Interfering RNA: Approaching Effective Cancer Therapies," Cancer Res., 2008, vol. 68, No. 5, pp. 1247-1250.
Pitt et al., "Rabbit Monoarticular Arthritis as a Model for Intra-Articular Drug Injections. The Local Action of Administered Cortisol and Alpha-1 Proteinase Inhibitor." Agents and Actions, vol. 15, No. 5-6, abstract online, retrieved from internet <URl:http://www.springerlink.com/content/j82860503948741/p> (Dec. 1984).
Polypure, Products; PEG amines; PEG acids and amino acids, PEG thiols and disulfides; BIOTINS, Apr. 2005.
Polypure, Products; PEG amines; PEG acids and amino acids; PEG thiols and disulfides; BIOTINS, Apr. 2004.
Poznansky et al., "Growth Hormone-Albumin-Conjugates Reduced Renal Toxicity and Altered Plasma Clearance," 1988, vol. 239, pp. 18-22.
Putterman, C., "Aprotinin Therapy in Septic Shock," Acta Chir. Scand., 155:367 (1989).
Quanta Biodesign, Labeling, Derivatization and Crosslinking Reagents for Biological and Related Materials with dPEGTM, pp. 1-38, Mar. 12, 2004.
Quanta Biodesign, Labeling, Modification and Crosslinking Reagents incorporating our unique monodispersed dPEGTM, pp. 1-31, Nov. 5, 2004.
Quanta Biodesign, Leading innovator, producer and provider of monodisperse discrete PEGTM (dPEGTM) derivatives, Product Catalogue, pp. 1-51, Updated: Jul. 18, 2005.
Quanta Biodesign, Leading innovator, producer and provider of monodisperse discrete PEGTM (dPEGTM) derivatives, Product Catalogue, pp. 1-51, Updated: Nov. 17, 2005.
Rahman et al., "Identification and Functional Importance of Plasma Kallikrein in the Synovial Fluids of Patients with Rheumatoid, Psoriatic, and Osteoarthritis," Annals of the Rheumatic Diseases, vol. 54, pp. 345-350 (1995).
Reichert, "Technology Evaluation: Lumiliximab, Biogen Idec" Curr Opin Mol Ther., 6(6):675-83 (2004). (Abstract only).
Robbins, K.C. et al., Hemostasis and Thrombosis, Chapter 21, 2nd Edition, Basic Principles and Clinical Practice: 340-357 (1987).
Roberts et al., "Directed Evolution of a Protein: Selection of Potent Neurtophil Elastase Inhibitor Displayed on M13 Fusion Phage," PNAS USA, vol. 89, pp. 2429-2433 (1992).
Roberts et al., "Protease Inhibitor Display M13 Phage: Selection of High-Affinity Neurtophil Elastase Inhibitors," Gene, vol. 121, pp. 9-15 (1992).
Roberts, M.J. et al., "Chemistry for Peptide and Protein PEGylation", Advanced Drug Delivery Reviews, 54, pp. 459-476, 2002.
Rossi, E. et al., The Synthetic Peptide DX88 Binds to Endothelial Cells In Vitro and Retains the Inhibitory Activity on Kallikrein, International Immunopharmacology 2(9):1313, Abstract 142 (2002).
Sainz I.M. et al., "Fifty Years of Research on the Plasma Kallikrein-Kinin System: from Protein Structure and Function to Cell Biology and in-Vivo Pathophysiology" Thromb Haemost 98, 77-83, 2007.
Sartor, R.B., et al., "Selective Kallikrein-Kinin System Activation in Inbred Rats Differentially Susceptible to Granulomatous Enterocolitis," Gastroenterology, 110:1467-1481 (1996).
Scarff et al., "Targeted Disruption of SP13/Serpinb6 Does Not Result in Development of Growth Defects, Leukocyte Dysfunction, or Susceptibility to Stroke," Molecular and Cellular Biology, May 2004, pp. 4075-4082.
Scatchard, George, The Attractions of Proteins for Small Molecules and Ions, ANN. NY ACAD. SCI, 51:660-672 (1949).
Schechter, et al., On the Active Site of Proteases, III. Mapping the Active Site of Papain; Specific Peptide Inhibitors of Papain, Biochemical and Biophysical Research Communications, vol. 32 (5): 898-902, (1968).
Schechter, et al., On the Size of the Active Site on Proteases, I. Papain, Biochemical and Biophysical Research Communications, vol. 27 (2): 157-162, (1967).
Schmaier A.H."Assembly, Activation, and Physiologic Influence of the Plasma Kallikrein/Kinin System" (2008) Int Immunopharmacology, 161-165.
Schmaier et al., Hemostasis and Thrombosis, Chapter 2, 2nd Edition, Basic Principals and Clinical Practice: 18-38 (1987).
Schmid-Elsaesser, et al., "A Critical Reevaluation of the Intraluminal Thread Model of Focal Cerebral Ischemia: Evidence of Inadvertent Premature Reperfusion and Subarachnoid Hemorrhage in Rats by Laser-Doppler Flowmetry" Stroke 29 (10): 2162-70 (1989).
Schmidt et al., "A Male Accessory Gland Peptide with Protease Inhibitory Activity in *Drosophila funebris*," Swiss-Prot, Accession #P11424 (1992).
Schnabel et al., Aprotinin: Preparation by Partial Desulphurization of Aprotinin by Means of Raney Nickel and Comparison with Other Aprotinin Derivatives, Biol. Chem. Hoppe-Seyler, 367:1167-1176 (1986).
Schoonooghe, et. al., "Efficient Production of Human Bivalent and Trivalent Anti-MUC1 Fab-scFv Antibodies in *Pichia pastoris*", BMC Biotechnol. Aug. 11, 2009;9:70.
Schopf, "IDEC-114 (IDEC)" Curr Opin Investig Drugs, 2(5):635-8 (2001). (Abstract only).
Schultz et al., "SMART, a Simple Modular Architecture Research Tool: Identification of Signaling Domains," PROC. NATL. ACAD. SCI. USA, 1998, vol. 95, p. 5857.
Schultz et al., "SMART: a Web-Based Tool for the Study of Genetically Mobile Domains," NUCL. ACIDS RES, 2000, vol. 28, p. 231-234.
Schwarz et al., "Stability Studies on Derivatives of the Bovine Trypsin Inhibitor," Biochemistry, vol. 26, pp. 3544-3551 (1987).
Shearwater Polymers, Inc., Polyethylene Glycol and Derivatives, pp. 1-50, catalogue—Jul. 1997.
Shearwater Corporation, Polyethylene Glycol and Derivatives for Biomedical Applications, pp. 1-17, catalogue—2001.
Shearwater Polymers, Inc., Polyethylene Glycol Derivatives: Functionalized Biocompatible Polymers for Research and Pharmaceuticals, pp. 1-50, catalogue—2000.
Shearwater Polymers, Inc., pp. 2-49, catalogue—Mar. 1995.
Sheppard, et al., Acid-Labile Resin Linkage Agents for Use in Solid Phase Peptide Synthesis, Int. J. Peptide Protein Res., 20:451-454 (1982).
Sheridan, et al., A Multicenter Trial of the Use of the Proteolytic Enzyme Inhibitor Aprotinin in Colorectal Surgery, Dis. Colon Rectum, 32:505-508 (1989).
Sherman et al., "Chapter 11: Conjugation of High-Molecular Weight Poly(Ethylene Glycol) to Cytokines: Granulocyte- Macrophage Colony-Stimulating Factors as Model Substrates," American Chemical Society, 1997, pp. 155-169.
Shibuya, et. al., "Primary Structure of Guinea Pig Plasma Prekallikrein", Immunopharmacology, vol. 45 (1-3), p. 127-34, Abstract p. 131, Fig 1, 2 (1999).
Siebeck et al., "Inhibition of Plasma Kallikrein with Aprotinin in Porcine Endotoxin Shock," J. Trauma, vol. 34, pp. 193-198 (1993).

(56) References Cited

OTHER PUBLICATIONS

Sik Eum W et al: "In Vivo Protein Transduction: Biologically Active Intact Pep-1-Superoxide Dismutase Fusion Protein Efficiently Protects Against Ischemic Insult", Free Radical Biology and Medicine, Elsevier Science, US, vol. 37, No. 10, Nov. 15, 2004, pp. 1656-1669.

Skolnick and Fetrow, From Genes to Protein Structure and Function: Novel Applications of Computational Approaches in the Genomic Era; Trends in Biotechnology, vol. 18, pp. 34-39 (2000). Skolnick et al. (Trends in Biotech. 18: 34-39, 2000).

Sonhammer et al., "PFAM: A Comprehensive Database of Protein Domain Families Based on Seed Alignments," Proteins, 1997, vol. 28 (3), pp. 405-420.

Sonis et al. "An Animal Model for Mucositis Induced by Cancer Chemotherapy" (1990) Oral Surg Oral Med Oral Pathol. 69:437-43.

Sonis et al. "Validation of a New Scoring System for the Assessment of Clinical Trial Research of Oral Mucositis Induced by Radiation or Chemotherapy. Mucositis Study Group." (1999) Cancer 85:2103-13.

Sprecher et al., "Molecular Cloning, Expression, and Partial Characterization of a Second Human Tissue-Factor-Pathway Inhibitor," Proc. Natl., Acad. Sci. USA, 91:3353-3357 (1994).

Stadnicki et al., "Activation of Plasma Contact and Coagulation Systems and Neutrophils in the Active Phase of Ulcerative Colitis," Digestive Diseases and Sciences, 1997, vol. 42, No. 1, pp. 2356-2366.

Stadnicki et al.. "Selective Plasma Kallikrein Inhibitor Attenuates Acute Intestinal Inflammation in Lewis Rat." Dig. Dis. Sci., 41:912-920 (1996).

Stadnicki, A., et al., 10th World Cong. Gastroenterology, Poster #1166P, (1994).

Strom et al., Therapeutic Immunology, Austen et al. (Ed.), Blackwell Science, Cambridge MA, 1996; pp. 451-456.

Stultz et al., "Structural Analysis Based on State-Space Modeling," PROTEIN SCI., 1993, vol. 2, pp. 305-314.

Sunkureddi et al., "Clinical Signs of Gout," Hospital Physician, 2006, pp. 39-41.

Supplemental European Search Report and Search Opinion from European Application No. 3791557.6 dated Oct. 19, 2007.

Supplemental European Search Report from EP App. No. 04786615.7 dated Jan. 20, 2009.

Supplemental Final Office Action on U.S. Appl. No. 11/930,018 (105493-0230) dated Mar. 18, 2010, 13 pages.

Supplementary European Search Report and European Search Opinion for European Application No. 05799587.0 (105493-0366) dated Nov. 28, 2012, 27 pages.

Supplementary European Search Report dated Jan. 19, 2009 from EP App. No. 04782687.0.

Supplementary European Search Report for EP Application No. 03757339.1 (105493-0252), mail date Apr. 23, 2008, 3 pages.

Supplementary European Search Report from European Application no. 8798232 dated Feb. 1, 2012.

Supplementary European Search Report including the European Search Opinion from corresponding European Application No. EP06848187.8, dated Dec. 7, 2009.

Taby et al., "Inhibition of Activated Protein C by Aprotinin and the Uses of the Insolubilized Inhibitor for Its Purification," Thrombosis Research, 1990, vol. 59, pp. 27-35.

Taggart et al., "Inactivation of Human-b-Defensins 2 and 3 by Elastolytic Cathepsins1 ," The Journal of Immunology, 2003, vol. 170, pp. 931-937.

Takahashi, et al., "Production of Humanized Fab Fragment Against Human High Affinity IgE Receptor in *Pichia pastoris*" Biosci Biotechnol Biochem 64(10):2138-44 (2000).

Tamura, et al., "Focal Cerebral Ischemia in the Rat: 1. Description of Technique and Early Neuropathological Consequences Following Middle Cerebral Artery Occlusion" J Cereb Blood Flow Metab 1: 53-60 (1981).

The Merck Index: pp. 145, 263, 427, 428, 1183, and 1184, (1989).

Tian et al., "Synthesis of Optically Pure Cα-methyl-arginine," Int. J. Peptide Protein Res., 40: 119-126 (1992).

Travis et al., "Pulmonary Perspective: Potential Problems in Designing Elastase Inhibitors for Therapy," Am. Rev. Respir. Dig., 1991, vol. 143, pp. 1412-1415.

Tremblay et al., "Anti-Inflammatory Activity of Neutrophil Elastase Inhibitors," Current Opinion in Investigational Drugs, 2003, vol. 4, No. 5, pp. 556-565.

Tschesche et al., "Semisynthetic Engineering of Proteinase Inhibitor Homologues," Biochim. Biophys. Acta, vol. 913, pp. 97-101 (1987).

Uebel,"Die Behandlung Con Kniegelenksarthrosen Mit Trasylol," Langenbacks Arch. Chir., vol. 325, pp. 356-358 (1969). English Abstract Only.

Urlaub et al., "Isolation of Chinese hamster Cell Mutants Deficient in Dihydrofolate Reductase Activity", Proc. Natl. Acad. Sci. USA 77:4216-4220 (1980).

van der Logt et al., "Intron-Exon Organization of the Human Gene Coding for the Lipoprotein-Associated Coagulation Inhibitor: The Factor Xa Dependent Inhibitor of the Extrinsic Pathway of Coagulation," Biochem., 30: 1571-1577 ( 1991).

van DijlI et al., "Signal Peptidase I of *Bacillus subtilis*: Patterns of Conserved Amino Acids in Prokaryotic and Eukaryotic Type I Signal Peptidases," EMBO J., 11:2819-2828 (1992).

Varadi and Patthy, "Location of Plasminogen-Binding Sites in Human Fibrin(ogen)," Biochem., 22:2440-2446 (1983).

Varadi and Patthy, "Segment of Fibrinogen is in a Region Essential for Plasminogen Binding by Fibrin Fragment E," Biochem., 23:2108-2112 (1984).

Vedvick, et al., "High-Level Secretion of Biologically Active Aprotinin from the Yeast *Pichia Pastoris*," J. Ind. Microbiol., 7:197-201 (1991).

Veronese, "Peptide and Protein PEGylation: a Review of Problems and Solutions," Biomaterials, Mar. 1, 2001, vol. 22, No. 5, pp. 405-417.

Vidal et al., "Making Sense of Antisense," European Journal of Cancer, 2005, vol. 41, pp. 2812-2818.

Viswanathan M. et al., "Engineered Protein Protease Inhibitors", Current Enzyme Inhibition, Jan. 1, 2009, pp. 87-98, vol. 5, No. 2, Betham Science Publishers Ltd., Hilversum, NL.

Volpe-Junior et al., "Augmented Plasma and Tissue Kallikrein Like Activity in Synovial Fluid of Patients with Inflammatory Articular Diseases," Inflamm. Res., 1996, vol. 45, pp. 198-202.

Wade et al., "Solid-Phase Synthesis of α-Human Atrial Natriuretic Factor: Comparison of the BocPolystyrene and Fmoc-Polyamide Methods," Biopolymers, 25:S21-37 (1986).

Wagner et al., "High Level Expression, Purification, and Characterization of the Kunitz-Type Protease Inhibitor Domain of Protease Nexin-2/Amyloid β-Protein Precursor," Biochem. Biophys. Res. Comm., 186:1138-1145 (1992).

Wang et al., "Monitoring of Heparin-Induced Anticoagulation with Kaolin-Activated Clotting Time in Cardiac Surgical Patients Treated with Aprotinin," Anesthesiology, vol. 77, pp. 1080-1084 (1992).

Wark P.A., "DX-890 (Dyax)", iDrugs, 5, pp. 586-589, Jun. 2002.

Wellington et al., "Tranexamic Acid: A Review of Its Use in the Management of Menorrhagia", Drugs, vol. 63, No. 13, pp. 1417-1433, 2003.

Wells. "Addivity of Mutational Effects in Proteins". Biochemistry, vol. 29 (37), pp. 8509-8517 (1990).

Wendel et al., Lower Cardiac Troponin T Levels in Patients Undergoing Cardiopulmonary Bypass and Receiving High-Dose Aprotinin Therapy Indicate Reduction of Perioperative Myocardial Damage; Journal of Thoracic Cardiovascular Surgery, vol. 109, No. 6, pp. 1164-1172 (1995).

Wilson, et al., "The Calculation and Synthesis of a Template Molecule," Tetrahedron, 49:3655-3663 (1993).

Wood, Alastair, J.J, "Hemostatic Drugs" New England Journal of Medicine, Drug Therapy, vol. 339, No. 4, pp. 245-253 (1998).

Worthy et al., "Current Status Review Kallikreins and Kinins: Mediators in Inflammatory Joint Disease," Int. J. Exp, 1990.

(56) References Cited

OTHER PUBLICATIONS

Worthy, K. et al., "Kallikreins and Kinins: Mediators in Inflammatory Joint Disease?", International Review of Experimental Pathology, pp. 587-601, vol. 71, No. 4, Blackwell Scientific, Oxford GB (Aug. 1, 1990).

Written Opinion from International Application No. PCT/US05/34335 dated Jul. 21, 2008.

Written Opinion from International Application No. PCT/US11/20377 dated Jun. 28, 2011.

Written Opinion from International Application No. PCT/US2008/074061 dated Dec. 29, 2008.

Wun et al., "Cloning and Characterization of a cDNA Coding for the Lipoprotein-associated Coagulation Inhibitor Shows that it Consists of Three Tandem Kunitz-type Inhibitory Domains," J. Biol. Chem., 263:6001-6004 (1988).

XP_376532.2 (GI:51465288): "Predicted: KIAA0408", GenBank Record created on Aug. 19, 2004, GenBank [online] Bethesda, MD USA: United States National Library of Medicine, retrieved from internet using <URL:http://www. ncbi.nlm.nih.gov/protein/XP_376532.2?report=genpepl > GenBank Accession No. XP_376532.2 (GI:51465288).

Xu et al., "The Crystal Structure of Bikunin from the Inter-a-Inhibitor Complex: a Serine Protease Inhibitor with Two Kumit2 Domains," J. Mol. Biol. Mar. 13, 1998, vol. 276, No. 5, pp. 955-966.

Feener, Plasma kallikrein and diabetic macular edema. Curr Diab Rep. Aug. 2010;10(4):270-5.

Phipps et al., Plasma kallikrein mediates angiotensin II type 1 receptor-stimulated retinal vascular permeability. Hypertension. Feb. 2009; 53(2):175-81. Epub Jan. 5, 2009.

*5AOX1*

```
                                                                BstB I
-------------------------------------->
CG ACT TTT AAC GAC AAC TTG AGA AGA TCA AAA AAC AAC TAA TTA TTC GAA
ACG    ATG AGA TTC CCA TCT ATC TTC ACT GCT GTT TTG TTC GCT GCT
        M   R   F   P   S   I   F   T   A   V   L   F   A   A
TCC TCT GCT TTG GCT GCT CCA GTT AAC ACC ACT ACT GAA GAC GAG ACT
 S   S   A   L   A   A   P   V   N   T   T   T   E   D   E   T
GCT CAA ATT CCT GCT GAG GCT GTC ATC GGT TAC TCT GAC TTG GAA GGT
 A   Q   I   P   A   E   A   V   I   G   Y   S   D   L   E   G
GAC TTC GAC GTC GCT GTT TTG CCA TTC TCT AAC TCT ACT AAC AAC GGT
 D   F   D   V   A   V   L   P   F   S   N   S   T   N   N   G
TTG TTG TTC ATC AAC ACT ACC ATC GCT TCT ATC GCT GCT AAG GAG GAA
 L   L   F   I   N   T   T   I   A   S   I   A   A   K   E   E
GGT GTT TCC CTC GAG AAG AGA GAG GCT ATG CAC TCT TTC TGT GCT TTC
 G   V   S   L   E   K   R   E   A   M   H   S   F   C   A   F
AAG GCT GAC GAC GGT CCG TGC AGA GCT GCT CAC CCA AGA TGG TTC TTC
 K   A   D   D   G   P   C   R   A   A   H   P   R   W   F   F
AAC ATC TTC ACG CGT CAA TGC GAG GAG TTC ATC TAC GGT GGT TGT GAG
 N   I   F   T   R   Q   C   E   E   F   I   Y   G   G   C   E
GGT AAC CAA AAC AGA TTC GAG TCT CTA GAG GAG TGT AAG AAG ATG TGT
 G   N   Q   N   R   F   E   S   L   E   E   C   K   K   M   C
                    EcoR I
ACT AGA GAC TAG TAA GAA TTC GCC TTA GAC ATG ACT GTT CCT CAG TTC
 T   R   D   *   *                                        <-------
                                                          3' AOX1
AAG TTG GGC ACT TAC GAG AAG
---------------------------
        3' AOX1
```

FIG. 2

```
SEQ ID 2:   (amino acids 3-60)    ----MHSFCAFKA-DDGPCRAAHPRWFFNIFTRQCEEFIYGG
SEQ ID 4:                         ----MHSFCAFKA-DDGPCKANHLRFFFNIFTRQCEEFSYGG
SEQ ID 5:                         ----MHSFCAFKA-DDGHCKANHQRFFFNIFTRQCEEFTYGG
SEQ ID 6:                         ----MHSFCAFKA-DDGHCKANHQRFFFNIFTRQCEQFTYGG
SEQ ID 7:                         ----MHSFCAFKA-DDGHCKASLPRFFFNIFTRQCEEFIYGG
SEQ ID 8:                         ----MHSFCAFKA-DDGHCKANHQRFFFNIFTRQCEEFSYGG
SEQ ID 9:                         ----MHSFCAKFA-DDGHCKGAHLRFFFNIFTRQCEEFIYGG
SEQ ID 10:                        ----MHSFCAFKA-DDGRCKGAHLRFFFNIFTRQCEEFIYGG
SEQ ID 11:                        ----MHSFCAFKA-DGGRCRGAHPRWFFNIFTRQCEEFSYGG
SEQ ID 12:                        ----MHSFCAFKA-DDGPCRAAHPRWFFNIFTRQCEEFSYGG
SEQ ID 13:                        ----MHSFCAFKA-DVGRCRGAHPRWFFNIFTRQCEEFSYGG
SEQ ID 14:                        ----MHSFCAFKA-DVGRCRGAQPRFFFNIFTRQCEEFSYGG
SEQ ID 15:                        ----MHSFCAFKA-DDGSCRAAHLRWFFNIFTRQCEEFSYGG
SEQ ID 16:                        ----MHSFCAFKA-EGGSCRAAHQRWFFNIFTRQCEEFSYGG
SEQ ID 17:                        ----MHSFCAFKA-DDGPCRGAHLRFFFNIFTRQCEEFSYGG
SEQ ID 18:                        ----MHSFCAFKA-DDGHCRGALPRWFFNIFTRQCEEFSYGG
SEQ ID 19:                        ----MHSFCAFKA-DSGNCRGNLPRFFFNIFTRQCEEFSYGG
SEQ ID 20:                        ----MHSFCAFKA-DSGRCRGNHQRFFFNIFTRQCEEFSYGG
SEQ ID 21:                        ----MHSFCAFKA-DGGRCRAIQPRWFFNIFTRQCEEFSYGG
SEQ ID 22:                        ----MHSFCAFKA-DDGRCRGAHPRWFFNIFTRQCEEFSYGG
BPTI (SEQ ID 29):                 ----RPDFCLEPP-YTGPCKARIIRYFYNAKAGLCQTFVYGG
ITI-D1 (SEQ ID 30):               ----KEDSCQLGY-SAGPCMGMTSRYFYNGTSMACETFQYGG
ITI-D2 (SEQ ID 31):               ----TVAACNLPI-VRGPCRAFIQLWAFDAVKGKCVLFPYGG
LACI-D1 (SEQ ID 32):              ----MHSFCAFKA-DDGPCKAIMKRFFFNIFTRQCEEFIYGG
LACI-D2 (SEQ ID 33):              ----KPDFCFLEE-DPGICRGYITRYFYNNQTKQCERFKYGG
LACI-D3 (SEQ ID 34):              ----GPSWCLTPA-DRGLCRANENRFYYNSVIGKCRPFKYSG
HKI B9 (SEQ ID 35):               ----LPNVCAFPM-EKGPCQTYMTRWFFNFETGECELFAYGG
Cα3 (SEQ ID 36):                  ----ETDICKLPK-DEGTCRDFILKWYYDPNTKSCARFWYGG
TFPI-2 D1 (SEQ ID 37):            ----NAEICLLPL-DYGPCRALLLRYYYDRYTQSCRQFLYGG
TFPI-2 D2 (SEQ ID 38):            ----VPKVCRLQVSVDDQCEGSTEKYFFNLSSMTCEKFFSGG
TFPI-2 D3 (SEQ ID 39):            ----IPSFCYSPK-DEGLCSANVTRYYFNPRYRTCDAFTYTG
APP-I (SEQ ID 40):                ---RNREVCSEQA-ETGPCRAMISRWYFDVTEGKCAPFFYGG
EpiNE7 (SEQ ID 41):               ----RPDFCLEPP-YTGPCVAMFPRYFYNAKAGLCQTFVYGG
BITI-E7-141 (SEQ ID 42):          ----RPDFCQLGY-SAGPCVAMFPRYFYNGTSMACQTFVYGG
MUTT26A (SEQ ID 43):              ----RPDFCQLGY-SAGPCVAMFPRYFYNGASMACQTFVYGG
MUTQE (SEQ ID 44):                ----RPDFCQLGY-SAGPCVAMFPRYFYNGTSMACETFVYGG
MUT1619 (SEQ ID 45):              ----RPDFCQLGY-SAGPCVGMFSRYFYNGTSMACQTFVYGG
EPI-HNE-1 (SEQ ID 46):            EAEARPDFCLEPP-YTGPCIAFFPRYFYNAKAGLCQTFVYGG
EPI-HNE-2 (SEQ ID 47):            ------AACNLPI-VRGPCIAFFPRWAFDAVKGKCVLFPYGG
EPI-HNE-3 (SEQ ID 48):            ------AACNLPI-VRGPCIAFFPRWAFDAVKGKCVLFPYGG
EPI-HNE-4 (SEQ ID 49):            ------EACNLPI-VRGPCIAFFPRWAFDAVKGKCVLFPYGG
DPI14 KR (SEQ ID 50):             --EAVREVCSEQA-ETGPCIAFFPRWYFDVTEGKCAPFFYGG
DPI24 KR (SEQ ID 51):             --EANAEICLLPL-DYGPCIAFFPRYYYDRYTQSCRQFLYGG
DPI68 KR (SEQ ID 52):             --EAKPDFCFLEE-DPGICIGFFPRYFYNNQAKQCERFVYGG
DPI84 KR (SEQ ID 53):             --EAETDICKLPK-DEGTCIAFFPRWYYDPNTKSCARFVYGG
```

FIG. 3A

| | | |
|---|---|---|
| SEQ ID 2: | (cont.) | CEGNQ--NRFESLEECKKMCTRD |
| SEQ ID 4: | (cont.) | CGGNQ--NRFESLEECKKMCTRD |
| SEQ ID 5: | (cont.) | CGGNQ--NRFESLEECKKMCTRD |
| SEQ ID 6: | (cont.) | CAGNQ--NRFESLEECKKMCTRD |
| SEQ ID 7: | (cont.) | CGGNQ--NRFESLEECKKMCTRD |
| SEQ ID 8: | (cont.) | CGGNQ--NRFESLEECKKMCTRD |
| SEQ ID 9: | (cont.) | CEGNQ--NRFESLEECKKMCTRD |
| SEQ ID 10: | (cont.) | CEGNQ--NRFESLEECKKMCTRD |
| SEQ ID 11: | (cont.) | CGGNQ--NRFESLEECKKMCTRD |
| SEQ ID 12: | (cont.) | CGGNQ--NRFESLEECKKMCTRD |
| SEQ ID 13: | (cont.) | CGGNQ--NRFESLEECKKMCTRD |
| SEQ ID 14: | (cont.) | CGGNQ--NRFESLEECKKMCTRD |
| SEQ ID 15: | (cont.) | CGGNQ--NRFESLEECKKMCTRD |
| SEQ ID 16: | (cont.) | CGGNQ--NRFESLEECKKMCTRD |
| SEQ ID 17: | (cont.) | CGGNQ--NRFESLEECKKMCTRD |
| SEQ ID 18: | (cont.) | CGGNQ--NRFESLEECKKMCTRD |
| SEQ ID 19: | (cont.) | CGGNQ--NRFESLEECKKMCTRD |
| SEQ ID 20: | (cont.) | CGGNQ--NRFESLEECKKMCTRD |
| SEQ ID 21: | (cont.) | CGGNQ--NRFESLEECKKMCTRD |
| SEQ ID 22: | (cont.) | CGGNQ--NRFESLEECKKMCTRD |
| BPTI (SEQ ID 29): | (cont.) | CRAKR--NNFKSAEDCMRTCGGA |
| ITI-D1 (SEQ ID 30): | (cont.) | CMGNG--NNFVTEKECLQTCRTV |
| ITI-D2 (SEQ ID 31): | (cont.) | CQGNG--NKFYSEKECREYCGVP |
| LACI-D1 (SEQ ID 32): | (cont.) | CEGNQ--NRFESLEECKKMCTRD |
| LACI-D2 (SEQ ID 33): | (cont.) | CLGNM--NNFETLEECKNICEDG |
| LACI-D3 (SEQ ID 34): | (cont.) | CGGNE--NNFTSKQECLRACKKG |
| HKI B9 (SEQ ID 35): | (cont.) | CGGNS--NNFLRKEKCEKFCKFT |
| Cα3 (SEQ ID 36): | (cont.) | CGGNE--NKFGSQKECEKVCAPV |
| TFPI-2 D1 (SEQ ID 37): | (cont.) | CEGNA--NNFYTWEACDDACWRI |
| TFPI-2 D2 (SEQ ID 38): | (cont.) | CHRNRIENRFPDEATCMGFCAPK |
| TFPI-2 D3 (SEQ ID 39): | (cont.) | CGGND--NNFVSREDCKRACAKA |
| APP-I (SEQ ID 40): | (cont.) | CGGNR--NNFDTEEYCMAVCGSA |
| EpiNE7 (SEQ ID 41): | (cont.) | CMGNG--NNFKSAEDCMRTCGGA |
| BITI-E7-141 (SEQ ID 42): | (cont.) | CMGNG--NNFVTEKDCLQTCRGA |
| MUTT26A (SEQ ID 43): | (cont.) | CMGNG--NNFVTEKDCLQTCRGA |
| MUTQE (SEQ ID 44): | (cont.) | CMGNG--NNFVTEKDCLQTCRGA |
| MUT1619 (SEQ ID 45): | (cont.) | CMGNG--NNFVTEKDCLQTCRGA |
| EPI-HNE-1 (SEQ ID 46): | (cont.) | CMGNG--NNFKSAEDCMRTCGGA |
| EPI-HNE-2 (SEQ ID 47): | (cont.) | CQGNG--NKFYSEKECREYCGVP |
| EPI-HNE-3 (SEQ ID 48): | (cont.) | CQGNG--NKFYSEKECREYCGVP |
| EPI-HNE-4 (SEQ ID 49): | (cont.) | CQGNG--NKFYSEKECREYCGVP |
| DPI14 KR (SEQ ID 50): | (cont.) | CGGNR--NNFDTEEYCMAVCGSA |
| DPI24 KR (SEQ ID 51): | (cont.) | CEGNA--NNFYTWEACDDACWRI |
| DPI68 KR (SEQ ID 52): | (cont.) | CLGNM--NNFETLEECKNICEDG |
| DPI84 KR (SEQ ID 53): | (cont.) | CGGNE--NKFGSQKECEKVCAPV |

FIG. 3B

SEQUENCE LISTING

<160> NUMBER OF SEQ ID NOS: 54

<210> SEQ ID NO 1
<211> LENGTH: 58
<212> TYPE: PRT
<213> ORGANISM: Artificial Sequence
<220> FEATURE:
<223> OTHER INFORMATION: Polypeptide Inhibiting Kallikrein
<220> FEATURE:
<221> NAME/KEY: VARIANT
<222> LOCATION: 1, 2, 3, 4, 6, 7, 8, 9, 20, 24, 25, 26, 27, 28, 29, 41,
      42, 44, 46, 47, 48, 49, 50, 52, 53, 54, 56, 57, 58
<223> OTHER INFORMATION: Xaa = any amino acid
<220> FEATURE:
<221> NAME/KEY: VARIANT
<222> LOCATION: 10
<223> OTHER INFORMATION: Xaa = Asp or Glu
<220> FEATURE:

```
<221> NAME/KEY: VARIANT
<222> LOCATION: 11
<223> OTHER INFORMATION: Xaa = Asp, Gly, Ser, Val, Asn, Ile, Ala or Thr
<220> FEATURE:
<221> NAME/KEY: VARIANT
<222> LOCATION: 13
<223> OTHER INFORMATION: Xaa = Arg, His, Pro, Asn, Ser, Thr, Ala, Gly,
      Lys or Gln
<220> FEATURE:
<221> NAME/KEY: VARIANT
<222> LOCATION: 15
<223> OTHER INFORMATION: Xaa = Arg, Lys, Ala, Ser, Gly, Met, Asn or Gln
<220> FEATURE:
<221> NAME/KEY: VARIANT
<222> LOCATION: 16
<223> OTHER INFORMATION: Xaa = Ala, Gly, Ser, Asp or Asn
<220> FEATURE:
<221> NAME/KEY: VARIANT
<222> LOCATION: 17
<223> OTHER INFORMATION: Xaa = Ala, Asn, Ser, Ile, Gly, Val, Gln or Thr
<220> FEATURE:
<221> NAME/KEY: VARIANT
<222> LOCATION: 18
<223> OTHER INFORMATION: Xaa = His, Leu, Gln or Ala
<220> FEATURE:
<221> NAME/KEY: VARIANT
<222> LOCATION: 19
<223> OTHER INFORMATION: Xaa = Pro, Gln, Leu, Asn or Ile
<220> FEATURE:
<221> NAME/KEY: VARIANT
<222> LOCATION: 21
<223> OTHER INFORMATION: Xaa = Trp, Phe, Tyr, His or Ile
<220> FEATURE:
<221> NAME/KEY: VARIANT
<222> LOCATION: 22
<223> OTHER INFORMATION: Xaa = Tyr or Phe
<220> FEATURE:
<221> NAME/KEY: VARIANT
<222> LOCATION: 23
<223> OTHER INFORMATION: Xaa = Tyr or Phe
<220> FEATURE:
<221> NAME/KEY: VARIANT
<222> LOCATION: 31
<223> OTHER INFORMATION: Xaa = Glu, Asp, Gln, Asn, Ser, Ala, Val, Leu,
      Ile or Thr
<220> FEATURE:
<221> NAME/KEY: VARIANT
<222> LOCATION: 32
<223> OTHER INFORMATION: Xaa = Glu, Gln, Asp, Asn, Pro, Thr, Leu, Ser,
      Ala, Gly or Val
<220> FEATURE:
<221> NAME/KEY: VARIANT
<222> LOCATION: 34
<223> OTHER INFORMATION: Xaa = Thr, Ile, Ser, Val, Ala, Asn, Gly or Leu
<220> FEATURE:
<221> NAME/KEY: VARIANT
<222> LOCATION: 35
<223> OTHER INFORMATION: Xaa = Tyr, Trp or Phe
<220> FEATURE:
<221> NAME/KEY: VARIANT
<222> LOCATION: 39
<223> OTHER INFORMATION: Xaa = Glu, Gly, Ala, Ser or Asp
<220> FEATURE:
<221> NAME/KEY: VARIANT
<222> LOCATION: 40
<223> OTHER INFORMATION: Xaa = Gly or Ala
<220> FEATURE:
<221> NAME/KEY: VARIANT
<222> LOCATION: 43
<223> OTHER INFORMATION: Xaa = Asn or Gly
<220> FEATURE:
<221> NAME/KEY: VARIANT
<222> LOCATION: 45
<223> OTHER INFORMATION: Xaa = Phe or Tyr

<400> SEQUENCE: 1

Xaa Xaa Xaa Xaa Cys Xaa Xaa Xaa Xaa Xaa Xaa Gly Xaa Cys Xaa Xaa
1               5                   10                  15
```

```
Xaa Xaa Xaa Xaa Xaa Xaa Xaa Xaa Xaa Xaa Xaa Cys Xaa Xaa
            20                  25                  30

Phe Xaa Xaa Gly Gly Cys Xaa Xaa Xaa Xaa Xaa Xaa Xaa Xaa
            35                  40                  45

Xaa Xaa Cys Xaa Xaa Xaa Cys Xaa Xaa Xaa
            50                  55

<210> SEQ ID NO 2
<211> LENGTH: 60
<212> TYPE: PRT
<213> ORGANISM: Artificial Sequence
<220> FEATURE:
<223> OTHER INFORMATION: Isolated Binding Peptide

<400> SEQUENCE: 2

Glu Ala Met His Ser Phe Cys Ala Phe Lys Ala Asp Asp Gly Pro Cys
 1               5                  10                  15

Arg Ala Ala His Pro Arg Trp Phe Phe Asn Ile Phe Thr Arg Gln Cys
            20                  25                  30

Glu Glu Phe Ile Tyr Gly Gly Cys Glu Gly Asn Gln Asn Arg Phe Glu
            35                  40                  45

Ser Leu Glu Glu Cys Lys Lys Met Cys Thr Arg Asp
            50                  55                  60

<210> SEQ ID NO 3
<211> LENGTH: 179
<212> TYPE: DNA
<213> ORGANISM: Artificial Sequence
<220> FEATURE:
<223> OTHER INFORMATION: Coding Sequence of Pep-1

<400> SEQUENCE: 3
gaggctatgc actctttctg tgctttcaag gctgacgacg gtcgtgcaga gctgctcacc        60
caagatggtt cttcaacatc ttcacgcgtc aatgcgagga gttcatctac ggtggttgtg       120
agggtaacca aaacagattc gagtctctag aggagtgtaa gaagatgtgt actagagac        179

<210> SEQ ID NO 4
<211> LENGTH: 58
<212> TYPE: PRT
<213> ORGANISM: Artificial Sequence
<220> FEATURE:
<223> OTHER INFORMATION: Isolated Binding Peptide

<400> SEQUENCE: 4

Met His Ser Phe Cys Ala Phe Lys Ala Asp Asp Gly Pro Cys Lys Ala
 1               5                  10                  15

Asn His Leu Arg Phe Phe Phe Asn Ile Phe Thr Arg Gln Cys Glu Glu
            20                  25                  30

Phe Ser Tyr Gly Gly Cys Gly Gly Asn Gln Asn Arg Phe Glu Ser Leu
            35                  40                  45

Glu Glu Cys Lys Lys Met Cys Thr Arg Asp
            50                  55

<210> SEQ ID NO 5
<211> LENGTH: 58
<212> TYPE: PRT
<213> ORGANISM: Artificial Sequence
<220> FEATURE:
<223> OTHER INFORMATION: Isolated Binding Peptide

<400> SEQUENCE: 5
```

```
Met His Ser Phe Cys Ala Phe Lys Ala Asp Asp Gly His Cys Lys Ala
1               5                   10                  15

Asn His Gln Arg Phe Phe Phe Asn Ile Phe Thr Arg Gln Cys Glu Glu
            20                  25                  30

Phe Thr Tyr Gly Gly Cys Gly Gly Asn Gln Asn Arg Phe Glu Ser Leu
        35                  40                  45

Glu Glu Cys Lys Lys Met Cys Thr Arg Asp
    50                  55
```

<210> SEQ ID NO 6
<211> LENGTH: 58
<212> TYPE: PRT
<213> ORGANISM: Artificial Sequence
<220> FEATURE:
<223> OTHER INFORMATION: Isolated Binding Peptide

<400> SEQUENCE: 6

```
Met His Ser Phe Cys Ala Phe Lys Ala Asp Asp Gly His Cys Lys Ala
1               5                   10                  15

Asn His Gln Arg Phe Phe Phe Asn Ile Phe Thr Arg Gln Cys Glu Gln
            20                  25                  30

Phe Thr Tyr Gly Gly Cys Ala Gly Asn Gln Asn Arg Phe Glu Ser Leu
        35                  40                  45

Glu Glu Cys Lys Lys Met Cys Thr Arg Asp
    50                  55
```

<210> SEQ ID NO 7
<211> LENGTH: 58
<212> TYPE: PRT
<213> ORGANISM: Artificial Sequence
<220> FEATURE:
<223> OTHER INFORMATION: Isolated Binding Peptide

<400> SEQUENCE: 7

```
Met His Ser Phe Cys Ala Phe Lys Ala Asp Asp Gly His Cys Lys Ala
1               5                   10                  15

Ser Leu Pro Arg Phe Phe Phe Asn Ile Phe Thr Arg Gln Cys Glu Glu
            20                  25                  30

Phe Ile Tyr Gly Gly Cys Gly Gly Asn Gln Asn Arg Phe Glu Ser Leu
        35                  40                  45

Glu Glu Cys Lys Lys Met Cys Thr Arg Asp
    50                  55
```

<210> SEQ ID NO 8
<211> LENGTH: 58
<212> TYPE: PRT
<213> ORGANISM: Artificial Sequence
<220> FEATURE:
<223> OTHER INFORMATION: Isolated Binding Peptide

<400> SEQUENCE: 8

```
Met His Ser Phe Cys Ala Phe Lys Ala Asp Asp Gly His Cys Lys Ala
1               5                   10                  15

Asn His Gln Arg Phe Phe Phe Asn Ile Phe Thr Arg Gln Cys Glu Glu
            20                  25                  30

Phe Ser Tyr Gly Gly Cys Gly Gly Asn Gln Asn Arg Phe Glu Ser Leu
        35                  40                  45

Glu Glu Cys Lys Lys Met Cys Thr Arg Asp
    50                  55
```

```
<210> SEQ ID NO 9
<211> LENGTH: 58
<212> TYPE: PRT
<213> ORGANISM: Artificial Sequence
<220> FEATURE:
<223> OTHER INFORMATION: Isolated Binding Peptide

<400> SEQUENCE: 9

Met His Ser Phe Cys Ala Phe Lys Ala Asp Asp Gly His Cys Lys Gly
1               5                   10                  15

Ala His Leu Arg Phe Phe Phe Asn Ile Phe Thr Arg Gln Cys Glu Glu
            20                  25                  30

Phe Ile Tyr Gly Gly Cys Glu Gly Asn Gln Asn Arg Phe Glu Ser Leu
        35                  40                  45

Glu Glu Cys Lys Lys Met Cys Thr Arg Asp
    50                  55

<210> SEQ ID NO 10
<211> LENGTH: 58
<212> TYPE: PRT
<213> ORGANISM: Artificial Sequence
<220> FEATURE:
<223> OTHER INFORMATION: Isolated Binding Peptide

<400> SEQUENCE: 10

Met His Ser Phe Cys Ala Phe Lys Ala Asp Asp Gly Arg Cys Lys Gly
1               5                   10                  15

Ala His Leu Arg Phe Phe Phe Asn Ile Phe Thr Arg Gln Cys Glu Glu
            20                  25                  30

Phe Ile Tyr Gly Gly Cys Glu Gly Asn Gln Asn Arg Phe Glu Ser Leu
        35                  40                  45

Glu Glu Cys Lys Lys Met Cys Thr Arg Asp
    50                  55

<210> SEQ ID NO 11
<211> LENGTH: 58
<212> TYPE: PRT
<213> ORGANISM: Artificial Sequence
<220> FEATURE:
<223> OTHER INFORMATION: Isolated Binding Peptide

<400> SEQUENCE: 11

Met His Ser Phe Cys Ala Phe Lys Ala Asp Gly Gly Arg Cys Arg Gly
1               5                   10                  15

Ala His Pro Arg Trp Phe Phe Asn Ile Phe Thr Arg Gln Cys Glu Glu
            20                  25                  30

Phe Ser Tyr Gly Gly Cys Gly Gly Asn Gln Asn Arg Phe Glu Ser Leu
        35                  40                  45

Glu Glu Cys Lys Lys Met Cys Thr Arg Asp
    50                  55

<210> SEQ ID NO 12
<211> LENGTH: 58
<212> TYPE: PRT
<213> ORGANISM: Artificial Sequence
<220> FEATURE:
<223> OTHER INFORMATION: Isolated Binding Peptide

<400> SEQUENCE: 12

Met His Ser Phe Cys Ala Phe Lys Ala Asp Asp Gly Pro Cys Arg Ala
1               5                   10                  15
```

```
Ala His Pro Arg Trp Phe Phe Asn Ile Phe Thr Arg Gln Cys Glu Glu
            20                  25                  30

Phe Ser Tyr Gly Gly Cys Gly Gly Asn Gln Asn Arg Phe Glu Ser Leu
        35                  40                  45

Glu Glu Cys Lys Lys Met Cys Thr Arg Asp
    50                  55

<210> SEQ ID NO 13
<211> LENGTH: 58
<212> TYPE: PRT
<213> ORGANISM: Artificial Sequence
<220> FEATURE:
<223> OTHER INFORMATION: Isolated Binding Peptide

<400> SEQUENCE: 13

Met His Ser Phe Cys Ala Phe Lys Ala Asp Val Gly Arg Cys Arg Gly
1               5                   10                  15

Ala His Pro Arg Trp Phe Phe Asn Ile Phe Thr Arg Gln Cys Glu Glu
            20                  25                  30

Phe Ser Tyr Gly Gly Cys Gly Gly Asn Gln Asn Arg Phe Glu Ser Leu
        35                  40                  45

Glu Glu Cys Lys Lys Met Cys Thr Arg Asp
    50                  55

<210> SEQ ID NO 14
<211> LENGTH: 58
<212> TYPE: PRT
<213> ORGANISM: Artificial Sequence
<220> FEATURE:
<223> OTHER INFORMATION: Isolated Binding Peptide

<400> SEQUENCE: 14

Met His Ser Phe Cys Ala Phe Lys Ala Asp Val Gly Arg Cys Arg Gly
1               5                   10                  15

Ala Gln Pro Arg Phe Phe Phe Asn Ile Phe Thr Arg Gln Cys Glu Glu
            20                  25                  30

Phe Ser Tyr Gly Gly Cys Gly Gly Asn Gln Asn Arg Phe Glu Ser Leu
        35                  40                  45

Glu Glu Cys Lys Lys Met Cys Thr Arg Asp
    50                  55

<210> SEQ ID NO 15
<211> LENGTH: 58
<212> TYPE: PRT
<213> ORGANISM: Artificial Sequence
<220> FEATURE:
<223> OTHER INFORMATION: Isolated Binding Peptide

<400> SEQUENCE: 15

Met His Ser Phe Cys Ala Phe Lys Ala Asp Asp Gly Ser Cys Arg Ala
1               5                   10                  15

Ala His Leu Arg Trp Phe Phe Asn Ile Phe Thr Arg Gln Cys Glu Glu
            20                  25                  30

Phe Ser Tyr Gly Gly Cys Gly Gly Asn Gln Asn Arg Phe Glu Ser Leu
        35                  40                  45

Glu Glu Cys Lys Lys Met Cys Thr Arg Asp
    50                  55

<210> SEQ ID NO 16
<211> LENGTH: 58
<212> TYPE: PRT
```

<213> ORGANISM: Artificial Sequence
<220> FEATURE:
<223> OTHER INFORMATION: Isolated Binding Peptide

<400> SEQUENCE: 16

Met His Ser Phe Cys Ala Phe Lys Ala Glu Gly Gly Ser Cys Arg Ala
1               5                   10                  15

Ala His Gln Arg Trp Phe Phe Asn Ile Phe Thr Arg Gln Cys Glu Glu
                20                  25                  30

Phe Ser Tyr Gly Gly Cys Gly Gly Asn Gln Asn Arg Phe Glu Ser Leu
            35                  40                  45

Glu Glu Cys Lys Lys Met Cys Thr Arg Asp
    50                  55

<210> SEQ ID NO 17
<211> LENGTH: 58
<212> TYPE: PRT
<213> ORGANISM: Artificial Sequence
<220> FEATURE:
<223> OTHER INFORMATION: Isolated Binding Peptide

<400> SEQUENCE: 17

Met His Ser Phe Cys Ala Phe Lys Ala Asp Asp Gly Pro Cys Arg Gly
1               5                   10                  15

Ala His Leu Arg Phe Phe Phe Asn Ile Phe Thr Arg Gln Cys Glu Glu
                20                  25                  30

Phe Ser Tyr Gly Gly Cys Gly Gly Asn Gln Asn Arg Phe Glu Ser Leu
            35                  40                  45

Glu Glu Cys Lys Lys Met Cys Thr Arg Asp
    50                  55

<210> SEQ ID NO 18
<211> LENGTH: 58
<212> TYPE: PRT
<213> ORGANISM: Artificial Sequence
<220> FEATURE:
<223> OTHER INFORMATION: Isolated Binding Peptide

<400> SEQUENCE: 18

Met His Ser Phe Cys Ala Phe Lys Ala Asp Asp Gly His Cys Arg Gly
1               5                   10                  15

Ala Leu Pro Arg Trp Phe Phe Asn Ile Phe Thr Arg Gln Cys Glu Glu
                20                  25                  30

Phe Ser Tyr Gly Gly Cys Gly Gly Asn Gln Asn Arg Phe Glu Ser Leu
            35                  40                  45

Glu Glu Cys Lys Lys Met Cys Thr Arg Asp
    50                  55

<210> SEQ ID NO 19
<211> LENGTH: 58
<212> TYPE: PRT
<213> ORGANISM: Artificial Sequence
<220> FEATURE:
<223> OTHER INFORMATION: Isolated Binding Peptide

<400> SEQUENCE: 19

Met His Ser Phe Cys Ala Phe Lys Ala Asp Ser Gly Asn Cys Arg Gly
1               5                   10                  15

Asn Leu Pro Arg Phe Phe Phe Asn Ile Phe Thr Arg Gln Cys Glu Glu
                20                  25                  30

Phe Ser Tyr Gly Gly Cys Gly Gly Asn Gln Asn Arg Phe Glu Ser Leu

-continued

```
              35                  40                  45
Glu Glu Cys Lys Lys Met Cys Thr Arg Asp
    50                  55

<210> SEQ ID NO 20
<211> LENGTH: 58
<212> TYPE: PRT
<213> ORGANISM: Artificial Sequence
<220> FEATURE:
<223> OTHER INFORMATION: Isolated Binding Peptide

<400> SEQUENCE: 20

Met His Ser Phe Cys Ala Phe Lys Ala Asp Ser Gly Arg Cys Arg Gly
1               5                   10                  15

Asn His Gln Arg Phe Phe Asn Ile Phe Thr Arg Gln Cys Glu Glu
            20                  25                  30

Phe Ser Tyr Gly Gly Cys Gly Gly Asn Gln Asn Arg Phe Glu Ser Leu
        35                  40                  45

Glu Glu Cys Lys Lys Met Cys Thr Arg Asp
    50                  55

<210> SEQ ID NO 21
<211> LENGTH: 58
<212> TYPE: PRT
<213> ORGANISM: Artificial Sequence
<220> FEATURE:
<223> OTHER INFORMATION: Isolated Binding Peptide

<400> SEQUENCE: 21

Met His Ser Phe Cys Ala Phe Lys Ala Asp Gly Gly Arg Cys Arg Ala
1               5                   10                  15

Ile Gln Pro Arg Trp Phe Phe Asn Ile Phe Thr Arg Gln Cys Glu Glu
            20                  25                  30

Phe Ser Tyr Gly Gly Cys Gly Gly Asn Gln Asn Arg Phe Glu Ser Leu
        35                  40                  45

Glu Glu Cys Lys Lys Met Cys Thr Arg Asp
    50                  55

<210> SEQ ID NO 22
<211> LENGTH: 58
<212> TYPE: PRT
<213> ORGANISM: Artificial Sequence
<220> FEATURE:
<223> OTHER INFORMATION: Isolated Binding Peptide

<400> SEQUENCE: 22

Met His Ser Phe Cys Ala Phe Lys Ala Asp Asp Gly Arg Cys Arg Gly
1               5                   10                  15

Ala His Pro Arg Trp Phe Phe Asn Ile Phe Thr Arg Gln Cys Glu Glu
            20                  25                  30

Phe Ser Tyr Gly Gly Cys Gly Gly Asn Gln Asn Arg Phe Glu Ser Leu
        35                  40                  45

Glu Glu Cys Lys Lys Met Cys Thr Arg Asp
    50                  55

<210> SEQ ID NO 23
<211> LENGTH: 6
<212> TYPE: DNA
<213> ORGANISM: Artificial Sequence
<220> FEATURE:
<223> OTHER INFORMATION: Modified Cloning Site
```

<400> SEQUENCE: 23 ttcgaa                                                                    6

<210> SEQ ID NO 24
<211> LENGTH: 8
<212> TYPE: DNA
<213> ORGANISM: Artificial Sequence
<220> FEATURE:
<223> OTHER INFORMATION: Modified Cloning Site

<400> SEQUENCE: 24 ttcgcgaa                                                                  8

<210> SEQ ID NO 25
<211> LENGTH: 6
<212> TYPE: DNA
<213> ORGANISM: Artificial Sequence
<220> FEATURE:
<223> OTHER INFORMATION: Modified Cloning Site

<400> SEQUENCE: 25 gacgtc                                                                    6

<210> SEQ ID NO 26
<211> LENGTH: 10
<212> TYPE: DNA
<213> ORGANISM: Artificial Sequence
<220> FEATURE:
<223> OTHER INFORMATION: Modified Cloning Site

<400> SEQUENCE: 26
gacgtacgtc                                                               10

<210> SEQ ID NO 27
<211> LENGTH: 548
<212> TYPE: DNA
<213> ORGANISM: Artificial Sequence
<220> FEATURE:
<223> OTHER INFORMATION: Nucleotide Sequence of Fusion Protein

<400> SEQUENCE: 27 cgactttta  acgacaacttg  agaagatcaa  aaaacaacta  attattcgaa  acgatgagat     60
tcccatctat  cttcactgct  gttttgttcg  ctgcttcctc  tgctttggct  gctccagtta   120
acaccactac  tgaagacgag  actgctcaaa  ttcctgctga  ggctgtcatc  ggttactctg   180
acttggaagg  tgacttcgac  gtcgctgttt  tgccattctc  taactctact  aacaacggtt   240
tgttgttcat  caacactacc  atcgcttcta  tcgctgctaa  ggaggaaggt  gtttccctcg   300
agaagagaga  ggctatgcac  tctttctgtg  ctttcaaggc  tgacgacggt  ccgtgcagag   360
ctgctcaccc  aagatggttc  ttcaacatct  tcacgcgtca  atgcgaggag  ttcatctacg   420
gtggttgtga  gggtaaccaa  aacagattcg  agtctctaga  ggagtgtaag  aagatgtgta   480
ctagagacta  gtaagaattc  gccttagaca  tgactgttcc  tcagttcaag  ttgggcactt   540
acgagaag                                                                548

<210> SEQ ID NO 28
<211> LENGTH: 145
<212> TYPE: PRT
<213> ORGANISM: Artificial Sequence
<220> FEATURE:
<223> OTHER INFORMATION: Fusion Protein

<400> SEQUENCE: 28

```
Met Arg Phe Pro Ser Ile Phe Thr Ala Val Leu Phe Ala Ala Ser Ser
 1               5                  10                  15

Ala Leu Ala Ala Pro Val Asn Thr Thr Thr Glu Asp Glu Thr Ala Gln
             20                  25                  30

Ile Pro Ala Glu Ala Val Ile Gly Tyr Ser Asp Leu Glu Gly Asp Phe
         35                  40                  45

Asp Val Ala Val Leu Pro Phe Ser Asn Ser Thr Asn Asn Gly Leu Leu
     50                  55                  60

Phe Ile Asn Thr Thr Ile Ala Ser Ile Ala Lys Glu Glu Gly Val
 65                  70                  75                  80

Ser Leu Glu Lys Arg Glu Ala Met His Ser Phe Cys Ala Phe Lys Ala
                 85                  90                  95

Asp Asp Gly Pro Cys Arg Ala Ala His Pro Arg Trp Phe Phe Asn Ile
             100                 105                 110

Phe Thr Arg Gln Cys Glu Glu Phe Ile Tyr Gly Gly Cys Glu Gly Asn
         115                 120                 125

Gln Asn Arg Phe Glu Ser Leu Glu Glu Cys Lys Lys Met Cys Thr Arg
     130                 135                 140

Asp
145

<210> SEQ ID NO 29
<211> LENGTH: 58
<212> TYPE: PRT
<213> ORGANISM: Artificial Sequence
<220> FEATURE:
<223> OTHER INFORMATION: BPTI Sequence

<400> SEQUENCE: 29

Arg Pro Asp Phe Cys Leu Glu Pro Pro Tyr Thr Gly Pro Cys Lys Ala
 1               5                  10                  15

Arg Ile Ile Arg Tyr Phe Tyr Asn Ala Lys Ala Gly Leu Cys Gln Thr
             20                  25                  30

Phe Val Tyr Gly Gly Cys Arg Ala Lys Arg Asn Asn Phe Lys Ser Ala
         35                  40                  45

Glu Asp Cys Met Arg Thr Cys Gly Gly Ala
     50                  55

<210> SEQ ID NO 30
<211> LENGTH: 58
<212> TYPE: PRT
<213> ORGANISM: Artificial Sequence
<220> FEATURE:
<223> OTHER INFORMATION: ITI-D1 Sequence

<400> SEQUENCE: 30

Lys Glu Asp Ser Cys Gln Leu Gly Tyr Ser Ala Gly Pro Cys Met Gly
 1               5                  10                  15

Met Thr Ser Arg Tyr Phe Tyr Asn Gly Thr Ser Met Ala Cys Glu Thr
             20                  25                  30

Phe Gln Tyr Gly Gly Cys Met Gly Asn Gly Asn Asn Phe Val Thr Glu
         35                  40                  45

Lys Glu Cys Leu Gln Thr Cys Arg Thr Val
     50                  55

<210> SEQ ID NO 31
<211> LENGTH: 58
<212> TYPE: PRT
```

```
<213> ORGANISM: Artificial Sequence
<220> FEATURE:
<223> OTHER INFORMATION: ITI-D2 Sequence

<400> SEQUENCE: 31

Thr Val Ala Ala Cys Asn Leu Pro Ile Val Arg Gly Pro Cys Arg Ala
 1               5                  10                  15

Phe Ile Gln Leu Trp Ala Phe Asp Ala Val Lys Gly Lys Cys Val Leu
                20                  25                  30

Phe Pro Tyr Gly Gly Cys Gln Gly Asn Gly Asn Lys Phe Tyr Ser Glu
            35                  40                  45

Lys Glu Cys Arg Glu Tyr Cys Gly Val Pro
    50                  55

<210> SEQ ID NO 32
<211> LENGTH: 58
<212> TYPE: PRT
<213> ORGANISM: Artificial Sequence
<220> FEATURE:
<223> OTHER INFORMATION: LACI-D1 Sequence

<400> SEQUENCE: 32

Met His Ser Phe Cys Ala Phe Lys Ala Asp Asp Gly Pro Cys Lys Ala
 1               5                  10                  15

Ile Met Lys Arg Phe Phe Phe Asn Ile Phe Thr Arg Gln Cys Glu Glu
                20                  25                  30

Phe Ile Tyr Gly Gly Cys Glu Gly Asn Gln Asn Arg Phe Glu Ser Leu
            35                  40                  45

Glu Glu Cys Lys Lys Met Cys Thr Arg Asp
    50                  55

<210> SEQ ID NO 33
<211> LENGTH: 58
<212> TYPE: PRT
<213> ORGANISM: Artificial Sequence
<220> FEATURE:
<223> OTHER INFORMATION: LACI-D2 Sequence

<400> SEQUENCE: 33

Lys Pro Asp Phe Cys Phe Leu Glu Glu Asp Pro Gly Ile Cys Arg Gly
 1               5                  10                  15

Tyr Ile Thr Arg Tyr Phe Tyr Asn Asn Gln Thr Lys Gln Cys Glu Arg
                20                  25                  30

Phe Lys Tyr Gly Gly Cys Leu Gly Asn Met Asn Asn Phe Glu Thr Leu
            35                  40                  45

Glu Glu Cys Lys Asn Ile Cys Glu Asp Gly
    50                  55

<210> SEQ ID NO 34
<211> LENGTH: 58
<212> TYPE: PRT
<213> ORGANISM: Artificial Sequence
<220> FEATURE:
<223> OTHER INFORMATION: LACI-D3 Sequence

<400> SEQUENCE: 34

Gly Pro Ser Trp Cys Leu Thr Pro Ala Asp Arg Gly Leu Cys Arg Ala
 1               5                  10                  15

Asn Glu Asn Arg Phe Tyr Tyr Asn Ser Val Ile Gly Lys Cys Arg Pro
                20                  25                  30

Phe Lys Tyr Ser Gly Cys Gly Gly Asn Glu Asn Asn Phe Thr Ser Lys
```

```
                    35                  40                  45

Gln Glu Cys Leu Arg Ala Cys Lys Lys Gly
    50                  55

<210> SEQ ID NO 35
<211> LENGTH: 58
<212> TYPE: PRT
<213> ORGANISM: Artificial Sequence
<220> FEATURE:
<223> OTHER INFORMATION: HKI B9 Sequence

<400> SEQUENCE: 35

Leu Pro Asn Val Cys Ala Phe Pro Met Glu Lys Gly Pro Cys Gln Thr
1               5                   10                  15

Tyr Met Thr Arg Trp Phe Phe Asn Phe Glu Thr Gly Glu Cys Glu Leu
            20                  25                  30

Phe Ala Tyr Gly Gly Cys Gly Gly Asn Ser Asn Asn Phe Leu Arg Lys
        35                  40                  45

Glu Lys Cys Glu Lys Phe Cys Lys Phe Thr
    50                  55

<210> SEQ ID NO 36
<211> LENGTH: 58
<212> TYPE: PRT
<213> ORGANISM: Artificial Sequence
<220> FEATURE:
<223> OTHER INFORMATION: C alpha 3 Sequence

<400> SEQUENCE: 36

Glu Thr Asp Ile Cys Lys Leu Pro Lys Asp Glu Gly Thr Cys Arg Asp
1               5                   10                  15

Phe Ile Leu Lys Trp Tyr Tyr Asp Pro Asn Thr Lys Ser Cys Ala Arg
            20                  25                  30

Phe Trp Tyr Gly Gly Cys Gly Gly Asn Glu Asn Lys Phe Gly Ser Gln
        35                  40                  45

Lys Glu Cys Glu Lys Val Cys Ala Pro Val
    50                  55

<210> SEQ ID NO 37
<211> LENGTH: 58
<212> TYPE: PRT
<213> ORGANISM: Artificial Sequence
<220> FEATURE:
<223> OTHER INFORMATION: TFPI-2 D1 Sequence

<400> SEQUENCE: 37

Asn Ala Glu Ile Cys Leu Leu Pro Leu Asp Tyr Gly Pro Cys Arg Ala
1               5                   10                  15

Leu Leu Leu Arg Tyr Tyr Tyr Asp Arg Tyr Thr Gln Ser Cys Arg Gln
            20                  25                  30

Phe Leu Tyr Gly Gly Cys Glu Gly Asn Ala Asn Asn Phe Tyr Thr Trp
        35                  40                  45

Glu Ala Cys Asp Asp Ala Cys Trp Arg Ile
    50                  55

<210> SEQ ID NO 38
<211> LENGTH: 61
<212> TYPE: PRT
<213> ORGANISM: Artificial Sequence
<220> FEATURE:
<223> OTHER INFORMATION: TFPI-2 D2 Sequence
```

```
<400> SEQUENCE: 38

Val Pro Lys Val Cys Arg Leu Gln Val Ser Val Asp Asp Gln Cys Glu
 1               5                  10                  15

Gly Ser Thr Glu Lys Tyr Phe Phe Asn Leu Ser Ser Met Thr Cys Glu
             20                  25                  30

Lys Phe Phe Ser Gly Gly Cys His Arg Asn Arg Ile Glu Asn Arg Phe
         35                  40                  45

Pro Asp Glu Ala Thr Cys Met Gly Phe Cys Ala Pro Lys
     50                  55                  60

<210> SEQ ID NO 39
<211> LENGTH: 58
<212> TYPE: PRT
<213> ORGANISM: Artificial Sequence
<220> FEATURE:
<223> OTHER INFORMATION: TFPI-2 D3 Sequence

<400> SEQUENCE: 39

Ile Pro Ser Phe Cys Tyr Ser Pro Lys Asp Glu Gly Leu Cys Ser Ala
 1               5                  10                  15

Asn Val Thr Arg Tyr Tyr Phe Asn Pro Arg Tyr Arg Thr Cys Asp Ala
             20                  25                  30

Phe Thr Tyr Thr Gly Cys Gly Gly Asn Asp Asn Asn Phe Val Ser Arg
         35                  40                  45

Glu Asp Cys Lys Arg Ala Cys Ala Lys Ala
     50                  55

<210> SEQ ID NO 40
<211> LENGTH: 59
<212> TYPE: PRT
<213> ORGANISM: Artificial Sequence
<220> FEATURE:
<223> OTHER INFORMATION: APP-I Sequence

<400> SEQUENCE: 40

Arg Asn Arg Glu Val Cys Ser Glu Gln Ala Glu Thr Gly Pro Cys Arg
 1               5                  10                  15

Ala Met Ile Ser Arg Trp Tyr Phe Asp Val Thr Glu Gly Lys Cys Ala
             20                  25                  30

Pro Phe Phe Tyr Gly Gly Cys Gly Gly Asn Arg Asn Asn Phe Asp Thr
         35                  40                  45

Glu Glu Tyr Cys Met Ala Val Cys Gly Ser Ala
     50                  55

<210> SEQ ID NO 41
<211> LENGTH: 58
<212> TYPE: PRT
<213> ORGANISM: Artificial Sequence
<220> FEATURE:
<223> OTHER INFORMATION: EpiNE7 Sequence

<400> SEQUENCE: 41

Arg Pro Asp Phe Cys Leu Glu Pro Pro Tyr Thr Gly Pro Cys Val Ala
 1               5                  10                  15

Met Phe Pro Arg Tyr Phe Tyr Asn Ala Lys Ala Gly Leu Cys Gln Thr
             20                  25                  30

Phe Val Tyr Gly Gly Cys Met Gly Asn Gly Asn Asn Phe Lys Ser Ala
         35                  40                  45

Glu Asp Cys Met Arg Thr Cys Gly Gly Ala
     50                  55
```

<210> SEQ ID NO 42
<211> LENGTH: 58
<212> TYPE: PRT
<213> ORGANISM: Artificial Sequence
<220> FEATURE:
<223> OTHER INFORMATION: BITI-E7-141 Sequence

<400> SEQUENCE: 42

Arg Pro Asp Phe Cys Gln Leu Gly Tyr Ser Ala Gly Pro Cys Val Ala
1               5                   10                  15

Met Phe Pro Arg Tyr Phe Tyr Asn Gly Thr Ser Met Ala Cys Gln Thr
            20                  25                  30

Phe Val Tyr Gly Gly Cys Met Gly Asn Gly Asn Asn Phe Val Thr Glu
        35                  40                  45

Lys Asp Cys Leu Gln Thr Cys Arg Gly Ala
    50                  55

<210> SEQ ID NO 43
<211> LENGTH: 58
<212> TYPE: PRT
<213> ORGANISM: Artificial Sequence
<220> FEATURE:
<223> OTHER INFORMATION: MUTT26A Sequence

<400> SEQUENCE: 43

Arg Pro Asp Phe Cys Gln Leu Gly Tyr Ser Ala Gly Pro Cys Val Ala
1               5                   10                  15

Met Phe Pro Arg Tyr Phe Tyr Asn Gly Ala Ser Met Ala Cys Gln Thr
            20                  25                  30

Phe Val Tyr Gly Gly Cys Met Gly Asn Gly Asn Asn Phe Val Thr Glu
        35                  40                  45

Lys Asp Cys Leu Gln Thr Cys Arg Gly Ala
    50                  55

<210> SEQ ID NO 44
<211> LENGTH: 58
<212> TYPE: PRT
<213> ORGANISM: Artificial Sequence
<220> FEATURE:
<223> OTHER INFORMATION: MUTQE Sequence

<400> SEQUENCE: 44

Arg Pro Asp Phe Cys Gln Leu Gly Tyr Ser Ala Gly Pro Cys Val Ala
1               5                   10                  15

Met Phe Pro Arg Tyr Phe Tyr Asn Gly Thr Ser Met Ala Cys Glu Thr
            20                  25                  30

Phe Val Tyr Gly Gly Cys Met Gly Asn Gly Asn Asn Phe Val Thr Glu
        35                  40                  45

Lys Asp Cys Leu Gln Thr Cys Arg Gly Ala
    50                  55

<210> SEQ ID NO 45
<211> LENGTH: 58
<212> TYPE: PRT
<213> ORGANISM: Artificial Sequence
<220> FEATURE:
<223> OTHER INFORMATION: MUT1619 Sequence

<400> SEQUENCE: 45

Arg Pro Asp Phe Cys Gln Leu Gly Tyr Ser Ala Gly Pro Cys Val Gly
1               5                   10                  15

```
Met Phe Ser Arg Tyr Phe Tyr Asn Gly Thr Ser Met Ala Cys Gln Thr
             20                  25                  30

Phe Val Tyr Gly Gly Cys Met Gly Asn Gly Asn Asn Phe Val Thr Glu
         35                  40                  45

Lys Asp Cys Leu Gln Thr Cys Arg Gly Ala
    50                  55
```

<210> SEQ ID NO 46
<211> LENGTH: 62
<212> TYPE: PRT
<213> ORGANISM: Artificial Sequence
<220> FEATURE:
<223> OTHER INFORMATION: EPI-HNE-1 Sequence

<400> SEQUENCE: 46

```
Glu Ala Glu Ala Arg Pro Asp Phe Cys Leu Glu Pro Pro Tyr Thr Gly
 1               5                  10                  15

Pro Cys Ile Ala Phe Phe Pro Arg Tyr Phe Tyr Asn Ala Lys Ala Gly
             20                  25                  30

Leu Cys Gln Thr Phe Val Tyr Gly Gly Cys Met Gly Asn Gly Asn Asn
         35                  40                  45

Phe Lys Ser Ala Glu Asp Cys Met Arg Thr Cys Gly Gly Ala
    50                  55                  60
```

<210> SEQ ID NO 47
<211> LENGTH: 56
<212> TYPE: PRT
<213> ORGANISM: Artificial Sequence
<220> FEATURE:
<223> OTHER INFORMATION: EPI-HNE-2 Sequence

<400> SEQUENCE: 47

```
Ala Ala Cys Asn Leu Pro Ile Val Arg Gly Pro Cys Ile Ala Phe Phe
 1               5                  10                  15

Pro Arg Trp Ala Phe Asp Ala Val Lys Gly Lys Cys Val Leu Phe Pro
             20                  25                  30

Tyr Gly Gly Cys Gln Gly Asn Gly Asn Lys Phe Tyr Ser Glu Lys Glu
         35                  40                  45

Cys Arg Glu Tyr Cys Gly Val Pro
    50                  55
```

<210> SEQ ID NO 48
<211> LENGTH: 56
<212> TYPE: PRT
<213> ORGANISM: Artificial Sequence
<220> FEATURE:
<223> OTHER INFORMATION: EPI-HNE-3 Sequence

<400> SEQUENCE: 48

```
Ala Ala Cys Asn Leu Pro Ile Val Arg Gly Pro Cys Ile Ala Phe Phe
 1               5                  10                  15

Pro Arg Trp Ala Phe Asp Ala Val Lys Gly Lys Cys Val Leu Phe Pro
             20                  25                  30

Tyr Gly Gly Cys Gln Gly Asn Gly Asn Lys Phe Tyr Ser Glu Lys Glu
         35                  40                  45

Cys Arg Glu Tyr Cys Gly Val Pro
    50                  55
```

<210> SEQ ID NO 49
<211> LENGTH: 56

```
<212> TYPE: PRT
<213> ORGANISM: Artificial Sequence
<220> FEATURE:
<223> OTHER INFORMATION: EPI-HNE-4 Sequence

<400> SEQUENCE: 49

Glu Ala Cys Asn Leu Pro Ile Val Arg Gly Pro Cys Ile Ala Phe Phe
1               5                   10                  15

Pro Arg Trp Ala Phe Asp Ala Val Lys Gly Lys Cys Val Leu Phe Pro
            20                  25                  30

Tyr Gly Gly Cys Gln Gly Asn Gly Asn Lys Phe Tyr Ser Glu Lys Glu
        35                  40                  45

Cys Arg Glu Tyr Cys Gly Val Pro
    50                  55

<210> SEQ ID NO 50
<211> LENGTH: 60
<212> TYPE: PRT
<213> ORGANISM: Artificial Sequence
<220> FEATURE:
<223> OTHER INFORMATION: DPI14 KR Sequence

<400> SEQUENCE: 50

Glu Ala Val Arg Glu Val Cys Ser Glu Gln Ala Glu Thr Gly Pro Cys
1               5                   10                  15

Ile Ala Phe Phe Pro Arg Trp Tyr Phe Asp Val Thr Glu Gly Lys Cys
            20                  25                  30

Ala Pro Phe Phe Tyr Gly Gly Cys Gly Gly Asn Arg Asn Asn Phe Asp
        35                  40                  45

Thr Glu Glu Tyr Cys Met Ala Val Cys Gly Ser Ala
    50                  55                  60

<210> SEQ ID NO 51
<211> LENGTH: 60
<212> TYPE: PRT
<213> ORGANISM: Artificial Sequence
<220> FEATURE:
<223> OTHER INFORMATION: DPI24 KR Sequence

<400> SEQUENCE: 51

Glu Ala Asn Ala Glu Ile Cys Leu Leu Pro Leu Asp Tyr Gly Pro Cys
1               5                   10                  15

Ile Ala Phe Phe Pro Arg Tyr Tyr Tyr Asp Arg Tyr Thr Gln Ser Cys
            20                  25                  30

Arg Gln Phe Leu Tyr Gly Gly Cys Glu Gly Asn Ala Asn Asn Phe Tyr
        35                  40                  45

Thr Trp Glu Ala Cys Asp Asp Ala Cys Trp Arg Ile
    50                  55                  60

<210> SEQ ID NO 52
<211> LENGTH: 60
<212> TYPE: PRT
<213> ORGANISM: Artificial Sequence
<220> FEATURE:
<223> OTHER INFORMATION: DPI68 KR Sequence

<400> SEQUENCE: 52

Glu Ala Lys Pro Asp Phe Cys Phe Leu Glu Glu Asp Pro Gly Ile Cys
1               5                   10                  15

Ile Gly Phe Phe Pro Arg Tyr Phe Tyr Asn Asn Gln Ala Lys Gln Cys
            20                  25                  30
```

Glu Arg Phe Val Tyr Gly Gly Cys Leu Gly Asn Met Asn Asn Phe Glu
                 35                  40                  45

Thr Leu Glu Glu Cys Lys Asn Ile Cys Glu Asp Gly
         50                  55                  60

<210> SEQ ID NO 53
<211> LENGTH: 60
<212> TYPE: PRT
<213> ORGANISM: Artificial Sequence
<220> FEATURE:
<223> OTHER INFORMATION: DPI84 KR Sequence

<400> SEQUENCE: 53

Glu Ala Glu Thr Asp Ile Cys Lys Leu Pro Lys Asp Glu Gly Thr Cys
  1               5                  10                  15

Ile Ala Phe Phe Pro Arg Trp Tyr Tyr Asp Pro Asn Thr Lys Ser Cys
                 20                  25                  30

Ala Arg Phe Val Tyr Gly Gly Cys Gly Gly Asn Glu Asn Lys Phe Gly
                 35                  40                  45

Ser Gln Lys Glu Cys Glu Lys Val Cys Ala Pro Val
         50                  55                  60

<210> SEQ ID NO 54
<211> LENGTH: 58
<212> TYPE: PRT
<213> ORGANISM: Artificial Sequence
<220> FEATURE:
<223> OTHER INFORMATION: VARIANT
<220> FEATURE:
<221> NAME/KEY: VARIANT
<222> LOCATION: 10
<223> OTHER INFORMATION: Xaa = Asp or Glu
<220> FEATURE:
<221> NAME/KEY: VARIANT
<222> LOCATION: 11
<223> OTHER INFORMATION: Xaa = Asp, Gly, Ser, Val, Asn, Ile, Ala or Thr
<220> FEATURE:
<221> NAME/KEY: VARIANT
<222> LOCATION: 13
<223> OTHER INFORMATION: Xaa = Arg, His, Pro, Asn, Ser, Thr, Ala, Gly,
      Lys or Gln
<220> FEATURE:
<221> NAME/KEY: VARIANT
<222> LOCATION: 15
<223> OTHER INFORMATION: Xaa = Arg, Ala, Ser, Gly, Met, Asn or Gln
<220> FEATURE:
<221> NAME/KEY: VARIANT
<222> LOCATION: 16
<223> OTHER INFORMATION: Xaa = Ala, Gly, Ser, Asp or Asn
<220> FEATURE:
<221> NAME/KEY: VARIANT
<222> LOCATION: 17
<223> OTHER INFORMATION: Xaa = Ala, Asn, Ser, Ile, Gly, Val, Gln or Thr
<220> FEATURE:
<221> NAME/KEY: VARIANT
<222> LOCATION: 18
<223> OTHER INFORMATION: Xaa = His, Leu, Gln or Ala
<220> FEATURE:
<221> NAME/KEY: VARIANT
<222> LOCATION: 19
<223> OTHER INFORMATION: Xaa = Pro, Gln, Leu, Asn or Ile
<220> FEATURE:
<221> NAME/KEY: VARIANT
<222> LOCATION: 21
<223> OTHER INFORMATION: Xaa = Trp, Phe, Tyr, His or Ile
<220> FEATURE:
<221> NAME/KEY: VARIANT
<222> LOCATION: 31
<223> OTHER INFORMATION: Xaa = Glu, Asp, Gln, Asn, Ser, Ala, Val, Leu,
      Ile or Thr
<220> FEATURE:
<221> NAME/KEY: VARIANT

```
<222> LOCATION: 32
<223> OTHER INFORMATION: Xaa = Glu, Gln, Asp, Asn, Pro, Thr, Leu, Ser,
      Ala, Gly or Val
<220> FEATURE:
<221> NAME/KEY: VARIANT
<222> LOCATION: 34
<223> OTHER INFORMATION: Xaa = Thr, Ile, Ser, Val, Ala, Asn, Gly or Leu
<220> FEATURE:
<221> NAME/KEY: VARIANT
<222> LOCATION: 35
<223> OTHER INFORMATION: Xaa = Tyr, Trp or Phe
<220> FEATURE:
<221> NAME/KEY: VARIANT
<222> LOCATION: 39
<223> OTHER INFORMATION: Xaa = Glu, Gly, Ala, Ser or Asp

<400> SEQUENCE: 54

Met His Ser Phe Cys Ala Phe Lys Ala Xaa Xaa Gly Xaa Cys Xaa Xaa
 1               5                  10                  15

Xaa Xaa Xaa Arg Xaa Phe Phe Asn Ile Phe Thr Arg Gln Cys Xaa Xaa
             20                  25                  30

Phe Xaa Xaa Gly Gly Cys Xaa Gly Asn Gln Asn Arg Phe Glu Ser Leu
         35                  40                  45

Glu Glu Cys Lys Lys Met Cys Thr Arg Asp
         50                  55
```

PREVENTION AND REDUCTION OF BLOOD LOSS

RELATED APPLICATION

This application is a continuation of U.S. patent application Ser. No. 12/951,543, filed Nov. 11, 2010, which is a continuation of U.S. patent application Ser. No. 11/929,729, filed Oct. 30, 2007, which is a continuation of U.S. patent application Ser. No. 11/796,272, filed Apr. 27, 2007, which is a continuation of U.S. patent application Ser. No. 11/322,960, filed Dec. 30, 2005, which is a continuation of U.S. patent application Ser. No. 10/456,986, filed Jun. 6, 2003, which claims the benefit of U.S. Provisional Application No. 60/387,239, filed Jun. 7, 2002, and U.S. Provisional Application No. 60/407,003, filed Aug. 28, 2002.

The entire teachings of the above applications are incorporated herein by reference.

BACKGROUND OF THE INVENTION

Proteases are involved in a broad range of biological pathways. In particular, serine proteases such as kallikrein, plasmin, elastase, urokinase plasminogen activator, thrombin, human lipoprotein-associated coagulation inhibitor, and coagulation factors such as factors VIIa, IXa, Xa, XIa, and XIIa have been implicated in pathways affecting blood flow, e.g., general and focal ischemia, tumor invasion, fibrinolysis, perioperative blood loss, and inflammation. Inhibitors of specific serine proteases, therefore, have received attention as potential drug targets for various ischemic maladies.

One such inhibitor, aprotinin (also called bovine pancreatic trypsin inhibitor or BPTI), obtained from bovine lung, has been approved in the United States for prophylactic use in reducing perioperative blood loss and the need for transfusion in patients undergoing cardiopulmonary bypass (CPB), e.g., in the course of a coronary artery bypass grafting procedure. Aprotinin is commercially available under the trade name TRASYLOL® (Bayer Corporation Pharmaceutical Division, West Haven, Conn.) and was previously approved for use to treat pancreatitis. The effectiveness of aprotinin is associated with its relatively non-specific abilities to inhibit a variety of serine proteases, including plasma kallikrein and plasmin. These proteases are important in a number of pathways of the contact activation system (CAS).

CAS is initially activated when whole blood contacts the surface of foreign substrates (e.g., kaolin, glass, dextran sulfate, or damaged bone surfaces). Kallikrein, a serine protease, is a plasma enzyme that initiates the CAS cascade leading to activation of neutrophils, plasmin, coagulation, and various kinins. Kallikrein is secreted as a zymogen (pre-kallikrein) that circulates as an inactive molecule until activated by a proteolytic event early in the contact activation cascade. Clearly, specific inhibition of kallikrein would be a very attractive approach to control blood loss associated with CPB and the onset of systemic inflammatory response (SIR) as would be encountered during, for example, various invasive surgical procedures:

Despite being the only licensed compound for preventing perioperative blood loss in CPB for coronary artery bypass grafting (CABG) procedures, aprotinin is not as widely used as would be expected. There are serious concerns regarding the use of this bovine polypeptide in patients who require CPB, and in particular the use of this compound in CABG procedures. Aprotinin is not specific for kallikrein, but interacts with additional enzymes (e.g., plasmin) in multiple pathways. Thus, the mechanism of action of aprotinin is largely speculative, and the lack of precise understanding of what is affected during aprotinin treatment produces the risk of complications during treatment. One frequently cited complication is uncontrolled thrombosis, due to aprotinin's actions upon the fibrinolytic pathway. There is concern not only over such hyperacute events as major vessel thrombosis in the perioperative period, but also over graft patency after the CABG procedure. Furthermore, as a naturally occurring protein obtained from bovine lung, administration of aprotinin in humans can elicit severe hypersensitivity or anaphylactic or anaphylactoid reactions after the first and, more often, after repeat administration to patients. This is particularly of concern in the large number of patients who have repeat CABG procedures. In addition, there is an increasing public concern regarding use of material derived from bovine sources as a potential vector for the transmission of bovine spongiform encephalopathy to humans.

These concerns make clear that a need remains for more effective and more specific means and methods for preventing or reducing perioperative blood loss and the onset of SIR in a patient subjected to surgery resulting in activation of the CAS, such as CABG procedures in patients of CPB, or hip replacement.

SUMMARY OF THE INVENTION

This invention is based on the discovery of peptides that inhibit serine proteases. Serine proteases such as, for example, kallikrein, are involved in, for example, pathways leading to excessive perioperative blood loss and the onset of systemic inflammatory response. Preferred kallikrein peptide inhibitors include those described in U.S. Pat. Nos. 6,333,402 and 6,057,287 to Markland et al., the contents of which are incorporated herein by reference in their entirety. The invention is directed in part to the use of the peptides in therapeutic methods and compositions suitable for use in eliminating or reducing various ischemias, including but not limited to perioperative blood loss, and the onset of systemic inflammatory response. Perioperative blood loss results from invasive surgical procedures that lead to contact activation of complement components and the coagulation/fibrinolysis systems. More specifically, the invention provides methods of using kallikrein inhibitors to reduce or prevent perioperative blood loss and a systemic inflammatory response in patients subjected to invasive surgical procedures, especially cardiothoracic surgeries.

In one embodiment, the invention is directed to a method for preventing or reducing ischemia in a patient comprising administering to the patient a composition comprising a polypeptide comprising the amino acid sequence: Xaa1 Xaa2 Xaa3 Xaa4 Cys Xaa6 Xaa7 Xaa8 Xaa9 Xaa10 Xaa11 Gly Xaa13 Cys Xaa15 Xaa16 Xaa17 Xaa18 Xaa19 Xaa20 Xaa21 Xaa22 Xaa23 Xaa24 Xaa25 Xaa26 Xaa27 Xaa28 Xaa29 Cys Xaa31 Xaa32 Phe Xaa34 Xaa35 Gly Gly Cys Xaa39 Xaa40 Xaa41 Xaa42 Xaa43 Xaa44 Xaa45 Xaa46 Xaa47 Xaa48 Xaa49 Xaa50 Cys Xaa52 Xaa53 Xaa54 Cys Xaa56 Xaa57 Xaa58 (SEQ ID NO:1), wherein Xaa1, Xaa2, Xaa3, Xaa4, Xaa56, Xaa57 or Xaa58 are each individually an amino acid or absent; Xaa10 is an amino acid selected from the group consisting of Asp and Glu; Xaa11 is an amino acid selected from the group consisting of: Asp, Gly, Ser, Val, Asn, Ile, Ala and Thr; Xaa13 is an amino acid selected from the group consisting of: Arg, His, Pro, Asn, Ser, Thr, Ala, Gly, Lys and Gln; Xaa15 is an amino acid selected from the group consisting of: Arg, Lys, Ala, Ser, Gly, Met, Asn and Gln; Xaa16 is an amino acid selected from the group consisting of: Ala, Gly, Ser, Asp and Asn; Xaa17 is an amino acid selected from the group consisting of: Ala, Asn, Ser, Ile, Gly, Val, Gln and Thr; Xaa18 is an amino acid selected from the group consisting of: His, Leu, Gln and Ala; Xaa19 is an amino acid selected from the group consisting of: Pro, Gln, Leu, Asn and Ile; Xaa21 is an amino acid selected from the group consisting of: Trp, Phe, Tyr, His and Ile; Xaa22 is an amino acid selected from the group consisting of Tyr and Phe; Xaa23 is an amino acid selected from the group consisting of: Tyr and Phe; Xaa31 is an amino acid selected from the group consisting of: Glu, Asp, Gln, Asn, Ser, Ala, Val, Leu, Ile and Thr; Xaa32 is an amino acid selected from the group consisting of: Glu, Gln, Asp Asn, Pro, Thr, Leu, Ser, Ala, Gly and Val; Xaa34 is an amino acid selected from the group consisting of: Thr, Ile, Ser, Val, Ala, Asn, Gly and Leu; Xaa35 is an amino acid selected from the group consisting of: Tyr, Trp and Phe; Xaa39 is an amino acid selected from the group consisting of: Glu, Gly, Ala, Ser and Asp; Xaa40 is an amino acid selected from the group consisting of Gly and Ala; Xaa43 is an amino acid selected from the group consisting of: Asn and Gly; Xaa45 is an amino acid selected from the group consisting of: Phe and Tyr; and wherein the polypeptide inhibits kallikrein.

In a particular embodiment, the ischemia is perioperative blood loss due to a surgical procedure performed on the patient. The surgical procedure can be a cardiothoracic surgery, such as, for example, cardiopulmonary bypass or coronary artery bypass grafting.

In a particular embodiment, individual amino acid positions of SEQ ID NO:1 can be one or more of the following: Xaa10 is Asp, Xaa11 is Asp, Xaa13 is Pro, Xaa15 is Arg, Xaa16 is Ala, Xaa17 is Ala, Xaa18 is His, Xaa19 is Pro, Xaa21 is Trp, Xaa31 is Glu, Xaa32 is Glu, Xaa34 is Ile, Xaa35 is Tyr, Xaa39 is Glu.

In another embodiment, the invention is directed to a method for preventing or reducing the onset of systemic inflammatory response associated with a surgical procedure in a patient comprising administering to the patient a composition comprising a polypeptide comprising the amino acid sequence: Xaa1 Xaa2 Xaa3 Xaa4 Cys Xaa6 Xaa7 Xaa8 Xaa9 Xaa10 Xaa11 Gly Xaa13 Cys Xaa15 Xaa16 Xaa17 Xaa18 Xaa19 Xaa20 Xaa21 Xaa22 Xaa23 Xaa24 Xaa25 Xaa26 Xaa27 Xaa28 Xaa29 Cys Xaa31 Xaa32 Phe Xaa34 Xaa35 Gly Gly Cys Xaa39 Xaa40 Xaa41 Xaa42 Xaa43 Xaa44 Xaa45 Xaa46 Xaa47 Xaa48 Xaa49 Xaa50 Cys Xaa52 Xaa53 Xaa54 Cys Xaa56 Xaa57 Xaa58 (SEQ ID NO:1), wherein Xaa1, Xaa2, Xaa3, Xaa4, Xaa56, Xaa57 or Xaa58 are each individually an amino acid or absent; Xaa10 is an amino acid selected from the group consisting of: Asp and Glu; Xaa11 is an amino acid selected from the group consisting of: Asp, Gly, Ser, Val, Asn, Ile, Ala and Thr; Xaa13 is an amino acid selected from the group consisting of: Arg, His, Pro, Asn, Ser, Thr, Ala, Gly, Lys and Gln; Xaa15 is an amino acid selected from the group consisting of: Arg, Lys, Ala, Ser, Gly, Met, Asn and Gln; Xaa16 is an amino acid selected from the group consisting of: Ala, Gly, Ser, Asp and Asn; Xaa17 is an amino acid selected from the group consisting of: Ala, Asn, Ser, Ile, Gly, Val, Gln and Thr; Xaa18 is an amino acid selected from the group consisting of: His, Leu, Gln and Ala; Xaa19 is an amino acid selected from the group consisting of Pro, Gln, Leu, Asn and Ile; Xaa21 is an amino acid selected from the group consisting of: Trp, Phe, Tyr, His and Ile; Xaa22 is an amino acid selected from the group consisting of: Tyr and Phe; Xaa23 is an amino acid selected from the group consisting of: Tyr and Phe; Xaa31 is an amino acid selected from the group consisting of Glu, Asp, Gln, Asn, Ser, Ala, Val, Leu, Ile and Thr; Xaa32 is an amino acid selected from the group consisting of Glu, Gln, Asp Asn, Pro, Thr, Leu, Ser, Ala, Gly and Val; Xaa34 is an amino acid selected from the group consisting of: Thr, Ile, Ser, Val, Ala, Asn, Gly and Leu; Xaa35 is an amino acid selected from the group consisting of: Tyr, Trp and Phe; Xaa39 is an amino acid selected from the group consisting of: Glu, Gly, Ala, Ser and Asp; Xaa40 is an amino acid selected from the group consisting of: Gly and Ala; Xaa43 is an amino acid selected from the group consisting of: Asn and Gly; Xaa45 is an amino acid selected from the group consisting of: Phe and Tyr; and wherein the polypeptide inhibits kallikrein. In a particular embodiment, the surgical procedure can be a cardiothoracic surgery, such as, for example, cardiopulmonary bypass or coronary artery bypass grafting. In a particular embodiment, individual amino acid positions of SEQ ID NO:1 can be one or more of the following: Xaa10 is Asp, Xaa11 is Asp, Xaa13 is Pro, Xaa15 is Arg, Xaa16 is Ala, Xaa17 is Ala, Xaa18 is His, Xaa19 is Pro, Xaa21 is Trp, Xaa31 is Glu, Xaa32 is Glu, Xaa34 is Ile, Xaa35 is Tyr, Xaa39 is Glu.

In yet another embodiment, the invention is directed to a method for preventing or reducing the onset of systemic inflammatory response associated with a surgical procedure in a patient comprising administering to the patient a composition comprising a polypeptide consisting of the amino acid sequence: Glu Ala Met His Ser Phe Cys Ala Phe Lys Ala Asp Asp Gly Pro Cys Arg Ala Ala His Pro Arg Trp Phe Phe Asn Ile Phe Thr Arg Gln Cys Glu Glu Phe Ile Tyr Gly Gly Cys Glu Gly Asn Gln Asn Arg Phe Glu Ser Leu Glu Glu Cys Lys Lys Met Cys Thr Arg Asp (SEQ ID NO:2), wherein the polypeptide inhibits kallikrein. In one embodiment, the surgical procedure is a cardiothoracic surgery, such as, for example, cardiopulmonary bypass or coronary artery bypass grafting.

In another embodiment, the invention is directed to a method for preventing or reducing ischemia in a patient comprising administering to the patient a composition comprising a polypeptide consisting of the amino acid sequence: Glu Ala Met His Ser Phe Cys Ala Phe Lys Ala Asp Asp Gly Pro Cys Arg Ala Ala His Pro Arg Trp Phe Phe Asn Ile Phe Thr Arg Gln Cys Glu Glu Phe Ile Tyr Gly Gly Cys Glu Gly Asn Gln Asn Arg Phe Glu Ser Leu Glu Glu Cys Lys Lys Met Cys Thr Arg Asp (SEQ ID NO:2), wherein the polypeptide inhibits kallikrein. In a particular embodiment, the ischemia can be perioperative blood loss due to a surgical procedure performed on the patient. In one embodiment, the surgical procedure is a cardiothoracic surgery, such as, for example, cardiopulmonary bypass or coronary artery bypass grafting.

In yet another embodiment, the invention is directed to a method for preventing or reducing the onset of systemic inflammatory response associated with a surgical procedure in a patient comprising administering to the patient a composition comprising a polypeptide consisting of the amino acid sequence: Met His Ser Phe Cys Ala Phe Lys Ala Asp Asp Gly Pro Cys Arg Ala Ala His Pro Arg Trp Phe Phe Asn Ile Phe Thr Arg Gln Cys Glu Glu Phe Ile Tyr Gly Gly Cys Glu Gly Asn Gln Asn Arg Phe Glu Ser Leu Glu Glu Cys Lys Lys Met Cys Thr Arg Asp (amino acids 3-60 of SEQ ID NO:2), wherein the polypeptide inhibits kallikrein. In one embodiment, the surgical procedure is a cardiothoracic surgery, such as, for example, cardiopulmonary bypass or coronary artery bypass grafting.

In another embodiment, the invention is directed to a method for preventing or reducing ischemia in a patient comprising administering to the patient a composition comprising a polypeptide consisting of the amino acid sequence: Met His Ser Phe Cys Ala Phe Lys Ala Asp Asp Gly Pro Cys Arg Ala Ala His Pro Arg Trp Phe Phe Asn Ile Phe Thr Arg Gln Cys Glu Glu Phe Ile Tyr Gly Gly Cys Glu Gly Asn Gln Asn Arg Phe Glu Ser Leu Glu Glu Cys Lys Lys Met Cys Thr Arg Asp (amino acids 3-60 of SEQ ID NO:2), wherein the polypeptide inhibits kallikrein. In a particular embodiment, the ischemia can be perioperative blood loss due to a surgical procedure performed on the patient. In one embodiment, the surgical procedure is a cardiothoracic surgery, such as, for example, cardiopulmonary bypass or coronary artery bypass grafting.

BRIEF DESCRIPTION OF THE DRAWINGS

FIG. 2 shows a portion of a DNA and corresponding deduced amino acid for a KI polypeptide of the invention in plasmid pPIC-K503. The inserted DNA encodes the mat.alpha. prepro signal peptide of Saccharomyces cerevisiae (underlined) fused in frame to the amino terminus of the PEP-1 KI polypeptide having the amino acid sequence enclosed by the boxed area. The amino acid sequence of the PEP-1 KI polypeptide shown in the boxed region is SEQ ID NO:2, and the corresponding nucleotide coding sequence of the KI polypeptide is SEQ ID NO:3. The dashed arrows indicate the location and direction of two PCR primer sequences in AOX regions that were used to produce sequencing templates. DNA sequence for the entire nucleotide sequence of the figure comprises the structural coding sequence for the fusion protein and is designated SEQ ID NO:27. The entire amino acid sequence is SEQ ID NO:28. The double underlined portion of the sequence indicates a diagnostic probe sequence. BstBI and EcoRI indicate locations of their respective palindromic, hexameric, restriction endonuclease sites in the sequence. Asterisks denote translational stop codons.

FIGS. 3A and 3B show an alignment of amino acid sequences of the preferred embodiments of the invention, the native LACI sequence from which these variants were derived (SEQ ID NO:32), and other known Kunitz domains (SEQ ID NOS:29-31 and 33-53). Cysteine residues are highlighted.

DETAILED DESCRIPTION OF THE INVENTION

Figure 1:
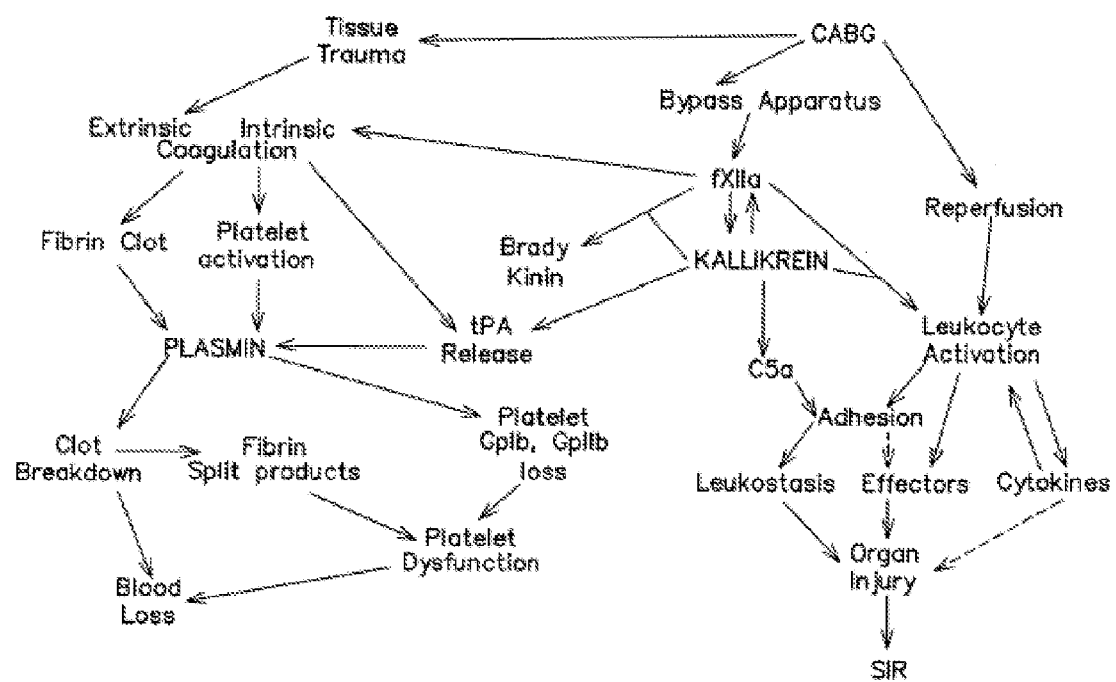
FIG. 1 is a simplified diagram of major multiple pathways and related events involved in the contact activation system and systemic inflammatory response (SIR) that can arise in a patient subjected to soft and bone tissue trauma such as that associated with a coronary artery bypass grafting (CABG) procedure, especially when the CABG procedure involves extra-corporeal blood circulation, such as cardiopulmonary bypass (Bypass Apparatus). Arrows indicate activation from one component or event to another component or event in the cascade. Arrows in both directions indicate activating effects of components or events in both directions. Broken arrows indicate likely participation of one component or event in the activation of another component or event. Abbreviations are as follows: "tPA"=tissue plasminogen activator; "C5a"=a protein component of the complement system; "fXIIa"=activator protein of prekallikrein to form active kallikrein; "Extrinsic"=extrinsic coagulation system; "Intrinsic"=intrinsic coagulation system.

A description of preferred embodiments of the invention follows.

The invention is based on the discovery of a group of kallikrein inhibitor (KI) polypeptides that inhibit plasma kallikrein with a specificity that permits their use in improved methods of preventing or reducing ischemia such as, for example, perioperative blood loss and/or a systemic inflammatory response (SIR) induced by kallikrein, especially, for example, in patients undergoing surgical procedures and particularly surgical procedures involving cardiothoracic surgery, e.g., cardiopulmonary bypass (CPB), such as a coronary artery bypass graft (CABG) procedures. K's can be used specifically for, e.g., pediatric cardiac surgery, lung transplantation, total hip replacement and orthotopic liver transplantation, and to reduce or prevent perioperative stroke during CABG, extracorporeal membrane oxygenation (ECMO) and cerebrovascular accidents (CVA) during these procedures.

Cardiothoracic surgery is surgery of the chest area, most commonly the heart and lungs. Typical diseases treated by cardiothoracic surgery include coronary artery disease, tumors and cancers of the lung, esophagus and chest wall, heart vessel and valve abnormalities, and birth defects involving the chest or heart. Where cardiothoracic surgery is utilized for treatment, the risk of blood loss (e.g., surgery-induced ischemia) and the onset of a systemic inflammatory response (SIR) is incurred. Surgery-induced SIR can result in severe organ dysfunction (systemic inflammatory response syndrome; SIRS).

Polypeptides Useful in the Invention

KI polypeptides useful in the invention comprise Kunitz domain polypeptides. In one embodiment these Kunitz domains are variant forms of the looped structure comprising Kunitz domain 1 of human lipoprotein-associated coagulation inhibitor (LACI) protein. LACI contains three internal, well-defined, peptide loop structures that are paradigm Kunitz domains (Girard, T. et al., 1989. Nature, 338:518-520). The three Kunitz domains of LACI confer the ability to bind and inhibit kallikrein, although not with exceptional affinity. Variants of Kunitz domain 1 of LACI described herein have been screened, isolated and bind kallikrein with enhanced affinity and specificity (see, for example, U.S. Pat. Nos. 5,795,865 and 6,057,287, incorporated herein by reference). An example of a preferred polypeptide useful in the invention has the amino acid sequence defined by amino acids 3-60 of SEQ ID NO:2.

Every polypeptide useful in the invention binds kallikrein, and preferred polypeptides are also kallikrein inhibitors (KI) as determined using kallikrein binding and inhibition assays known in the art. The enhanced affinity and specificity for kallikrein of the variant Kunitz domain polypeptides described herein provides the basis for their use in cardiothoracic surgery, e.g., CPB and especially CABG surgical procedures, to prevent or reduce perioperative blood loss and/or the onset of SIR in patients undergoing such procedures. The KI polypeptides used in the invention have or comprise the amino acid sequence of a variant Kunitz domain polypeptide originally isolated by screening phage display libraries for the ability to bind kallikrein.

KI polypeptides useful in the methods and compositions of the invention comprise a Kunitz domain polypeptide comprising the amino acid sequence:

```
                                           (SEQ ID NO: 1)
Xaa1 Xaa2 Xaa3 Xaa4 Cys Xaa6 Xaa7 Xaa8 Xaa9 Xaa10

Xaa11 Gly Xaa13 Cys Xaa15 Xaa16 Xaa17 Xaa18 Xaa19

Xaa20 Xaa21 Xaa22 Xaa23 Xaa24 Xaa25 Xaa26 Xaa27
```

-continued
```
Xaa28 Xaa29 Cys Xaa31 Xaa32 Phe Xaa34 Xaa35 Gly

Gly Cys Xaa39 Xaa40 Xaa41 Xaa42 Xaa43 Xaa44 Xaa45

Xaa46 Xaa47 Xaa48 Xaa49 Xaa50 Cys Xaa52 Xaa53

Xaa54 Cys Xaa56 Xaa57 Xaa58
```

"Xaa" refers to a position in a peptide chain that can be any of a number of different amino acids. For example, for the KI peptides described herein, Xaa10 can be Asp or Glu; Xaa11 can be Asp, Gly, Ser, Val, Asn, Ile, Ala or Thr; Xaa13 can be Pro, Arg, His, Asn, Ser, Thr, Ala, Gly, Lys or Gln; Xaa15 can be Arg, Lys, Ala, Ser, Gly, Met, Asn or Gln; Xaa16 can be Ala, Gly, Ser, Asp or Asn; Xaa17 can be Ala, Asn, Ser, Ile, Gly, Val, Gln or Thr; Xaa18 can be His, Leu, Gln or Ala; Xaa19 can be Pro, Gln, Leu, Asn or Ile; Xaa21 can be Trp, Phe, Tyr, His or Ile; Xaa31 can be Glu, Asp, Gln, Asn, Ser, Ala, Val, Leu, Ile or Thr; Xaa32 can be Glu, Gln, Asp Asn, Pro, Thr, Leu, Ser, Ala, Gly or Val; Xaa34 can be Ile, Thr, Ser, Val, Ala, Asn, Gly or Leu; Xaa35 can be Tyr, Trp or Phe; Xaa39 can be Glu, Gly, Ala, Ser or Asp. Amino acids Xaa6, Xaa7, Xaa8, Xaa9, Xaa20, Xaa24, Xaa25, Xaa26, Xaa27, Xaa28, Xaa29, Xaa41, Xaa42, Xaa44, Xaa46, Xaa47, Xaa48, Xaa49, Xaa50, Xaa52, Xaa53 and Xaa54 can be any amino acid. Additionally, each of the first four and at last three amino acids of SEQ ID NO:1 can optionally be present or absent and can be any amino acid, if present.

Peptides defined according to SEQ ID NO:1 form a set of polypeptides that bind to kallikrein. For example, in a preferred embodiment of the invention, a KI polypeptide useful in the methods and compositions of the invention has the following variable positions: Xaa (SEQ ID NO: 10)
Met His Ser Phe Cys Ala Phe Lys Ala Asp Asp Gly
Arg Cys Lys Gly Ala His Leu Arg Phe Phe Asn
Ile Phe Thr Arg Gln Cys Glu Glu Phe Ile Tyr Gly
Gly Cys Glu Gly Asn Gln Asn Arg Phe Glu Ser Leu
Glu Glu Cys Lys Lys Met Cys Thr Arg Asp, (SEQ ID NO: 11)
Met His Ser Phe Cys Ala Phe Lys Ala Asp Gly Gly
Arg Cys Arg Gly Ala His Pro Arg Trp Phe Phe Asn
Ile Phe Thr Arg Gln Cys Glu Glu Phe Ser Tyr Gly
Gly Cys Gly Gly Asn Gln Asn Arg Phe Glu Ser Leu
Glu Glu Cys Lys Lys Met Cys Thr Arg Asp, (SEQ ID NO: 12)
Met His Ser Phe Cys Ala Phe Lys Ala Asp Asp Gly
Pro Cys Arg Ala Ala His Pro Arg Trp Phe Phe Asn
Ile Phe Thr Arg Gln Cys Glu Glu Phe Ser Tyr Gly
Gly Cys Gly Gly Asn Gln Asn Arg Phe Glu Ser Leu
Glu Glu Cys Lys Lys Met Cys Thr Arg Asp, (SEQ ID NO: 13)
Met His Ser Phe Cys Ala Phe Lys Ala Asp Val Gly
Arg Cys Arg Gly Ala His Pro Arg Trp Phe Phe Asn
Ile Phe Thr Arg Gln Cys Glu Glu Phe Ser Tyr Gly
Gly Cys Gly Gly Asn Gln Asn Arg Phe Glu Ser Leu
Glu Glu Cys Lys Lys Met Cys Thr Arg Asp, (SEQ ID NO: 14)
Met His Ser Phe Cys Ala Phe Lys Ala Asp Val Gly
Arg Cys Arg Gly Ala Gln Pro Arg Phe Phe Asn
Ile Phe Thr Arg Gln Cys Glu Glu Phe Ser Tyr Gly
Gly Cys Gly Gly Asn Gln Asn Arg Phe Glu Ser Leu
Glu Glu Cys Lys Lys Met Cys Thr Arg Asp, (SEQ ID NO: 15)
Met His Ser Phe Cys Ala Phe Lys Ala Asp Asp Gly
Ser Cys Arg Ala Ala His Leu Arg Trp Phe Phe Asn
Ile Phe Thr Arg Gln Cys Glu Glu Phe Ser Tyr Gly
Gly Cys Gly Gly Asn Gln Asn Arg Phe Glu Ser Leu
Glu Glu Cys Lys Lys Met Cys Thr Arg Asp, (SEQ ID NO: 16)
Met His Ser Phe Cys Ala Phe Lys Ala Glu Gly Gly
Ser Cys Arg Ala Ala His Gln Arg Trp Phe Phe Asn
Ile Phe Thr Arg Gln Cys Glu Glu Phe Ser Tyr Gly
Gly Cys Gly Gly Asn Gln Asn Arg Phe Glu Ser Leu
Glu Glu Cys Lys Lys Met Cys Thr Arg Asp, (SEQ ID NO: 17)
Met His Ser Phe Cys Ala Phe Lys Ala Asp Asp Gly
Pro Cys Arg Gly Ala His Leu Arg Phe Phe Asn
Ile Phe Thr Arg Gln Cys Glu Glu Phe Ser Tyr Gly
Gly Cys Gly Gly Asn Gln Asn Arg Phe Glu Ser Leu
Glu Glu Cys Lys Lys Met Cys Thr Arg Asp, (SEQ ID NO: 18)
Met His Ser Phe Cys Ala Phe Lys Ala Asp Asp Gly
His Cys Arg Gly Ala Leu Pro Arg Trp Phe Phe Asn
Ile Phe Thr Arg Gln Cys Glu Glu Phe Ser Tyr Gly
Gly Cys Gly Gly Asn Gln Asn Arg Phe Glu Ser Leu
Glu Glu Cys Lys Lys Met Cys Thr Arg Asp, (SEQ ID NO: 19)
Met His Ser Phe Cys Ala Phe Lys Ala Asp Ser Gly
Asn Cys Arg Gly Asn Leu Pro Arg Phe Phe Asn
Ile Phe Thr Arg Gln Cys Glu Glu Phe Ser Tyr Gly
Gly Cys Gly Gly Asn Gln Asn Arg Phe Glu Ser Leu
Glu Glu Cys Lys Lys Met Cys Thr Arg Asp, (SEQ ID NO: 20)
Met His Ser Phe Cys Ala Phe Lys Ala Asp Ser Gly
Arg Cys Arg Gly Asn His Gln Arg Phe Phe Asn
Ile Phe Thr Arg Gln Cys Glu Glu Phe Ser Tyr Gly
Gly Cys Gly Gly Asn Gln Asn Arg Phe Glu Ser Leu
Glu Glu Cys Lys Lys Met Cys Thr Arg Asp, (SEQ ID NO: 21)
Met His Ser Phe Cys Ala Phe Lys Ala Asp Gly Gly
Arg Cys Arg Ala Ile Gln Pro Arg Trp Phe Phe Asn
Ile Phe Thr Arg Gln Cys Glu Glu Phe Ser Tyr Gly
Gly Cys Gly Gly Asn Gln Asn Arg Phe Glu Ser Leu
Glu Glu Cys Lys Lys Met Cys Thr Arg Asp, (SEQ ID NO: 22)
Met His Ser Phe Cys Ala Phe Lys Ala Asp Asp Gly
Arg Cys Arg Gly Ala His Pro Arg Trp Phe Phe Asn
Ile Phe Thr Arg Gln Cys Glu Glu Phe Ser Tyr Gly
Gly Cys Gly Gly Asn Gln Asn Arg Phe Glu Ser Leu
Glu Glu Cys Lys Lys Met Cys Thr Arg Asp.

FIGS. 3A and 3B provides an amino acid sequence alignment of these sequences, the native LACI sequence from which these variants were derived (SEQ ID NO:32), and other known Kunitz domains (SEQ ID NOS: 29-31 and 33-53).

The KI polypeptides useful in the methods and compositions described herein can be made synthetically using any standard polypeptide synthesis protocol and equipment. For example, the stepwise synthesis of a KI polypeptide described herein can be carried out by the removal of an amino (N) terminal-protecting group from an initial (i.e., carboxy-terminal) amino acid, and coupling thereto of the carboxyl end of the next amino acid in the sequence of the polypeptide. This amino acid is also suitably protected. The carboxyl group of the incoming amino acid can be activated to react with the N-terminus of the bound amino acid by formation into a reactive group such as formation into a carbodiimide, a symmetric acid anhydride, or an "active ester" group such as hydroxybenzotriazole or pentafluorophenyl esters. Preferred solid-phase peptide synthesis methods include the BOC method, which utilizes tert-butyloxycarbonyl as the .alpha.-amino protecting group, and the FMOC method, which utilizes 9-fluorenylmethloxycarbonyl to protect the .alpha.-amino of the amino acid residues. Both methods are well known to those of skill in the art (Stewart, J. and Young, J., Solid-Phase Peptide Synthesis (W. H. Freeman Co., San Francisco 1989); Merrifield, J., 1963. Am. Chem. Soc., 85:2149-2154; Bodanszky, M. and Bodanszky, A., The Practice of Peptide Synthesis (Springer-Verlag, New York 1984), the entire teachings of these references is incorporated herein by reference). If desired, additional amino- and/or carboxy-terminal amino acids can be designed into the amino acid sequence and added during polypeptide synthesis.

Alternatively, Kunitz domain polypeptides and KI polypeptides useful in the compositions and methods of the invention can be produced by recombinant methods using any of a number of cells and corresponding expression vectors, including but not limited to bacterial expression vectors, yeast expression vectors, baculovirus expression vectors, mammalian viral expression vectors, and the like. Kunitz domain polypeptides and KI polypeptides useful in the compositions and methods of the invention can also be produced transgenically using nucleic acid molecules comprising a coding sequence for a Kunitz domain or KI polypeptide described herein, wherein the nucleic acid molecule can be integrated into and expressed from the genome of a host animal using transgenic methods available in the art. In some cases, it could be necessary or advantageous to fuse the coding sequence for a Kunitz domain polypeptide or a KI polypeptide comprising the Kunitz domain to another coding sequence in an expression vector to form a fusion polypeptide that is readily expressed in a host cell. Preferably, the host cell that expresses such a fusion polypeptide also processes the fusion polypeptide to yield a Kunitz domain or KI polypeptide useful in the invention that contains only the desired amino acid sequence. Obviously, if any other amino acid(s) remain attached to the expressed Kunitz domain or KI polypeptide, such additional amino acid(s) should not diminish the kallikrein binding and/or kallikrein inhibitory activity of the Kunitz domain or KI polypeptide so as to preclude use of the polypeptide in the methods or compositions of the invention.

A preferred recombinant expression system for producing KI polypeptides useful in the methods and compositions described herein is a yeast expression vector, which permits a nucleic acid sequence encoding the amino acid sequence for a KI polypeptide or Kunitz domain polypeptide to be linked in the same reading frame with a nucleotide sequence encoding the mat.alpha. prepro leader peptide sequence of Saccharomyces cerevisiae, which in turn is under the control of an operable yeast promoter. The resulting recombinant yeast expression plasmid can then be transformed by standard methods into the cells of an appropriate, compatible yeast host, which cells are able to express the recombinant protein from the recombinant yeast expression vector. Preferably, a host yeast cell transformed with such a recombinant expression vector is also able to process the fusion protein to provide an active KI polypeptide useful in the methods and compositions of the invention. A preferred yeast host for producing recombinant Kunitz domain polypeptides and KI polypeptides comprising such Kunitz domains is Pichia pastoris.

As noted above, KI polypeptides that are useful in the methods and compositions described herein can comprise a Kunitz domain polypeptide described herein. Some KI polypeptides can comprise an additional flanking sequence, preferably of one to six amino acids in length, at the amino and/or carboxy-terminal end, provided such additional amino acids do not significantly diminish kallikrein binding affinity or kallikrein inhibition activity so as to preclude use in the methods and compositions described herein. Such additional amino acids can be deliberately added to express a KI polypeptide in a particular recombinant host cell or can be added to provide an additional function, e.g., to provide a peptide to link the KI polypeptide to another molecule or to provide an affinity moiety that facilitates purification of the polypeptide. Preferably, the additional amino acid(s) do not include cysteine, which could interfere with the disulfide bonds of the Kunitz domain.

An example of a preferred Kunitz domain polypeptide useful in the methods and compositions of the invention has the amino acid sequence of residues 3-60 of SEQ ID NO:2. When expressed and processed in a yeast fusion protein expression system (e.g., based on the integrating expression plasmid pHIL-D2), such a Kunitz domain polypeptide retains an additional amino terminal Glu-Ala dipeptide from the fusion with the mat.alpha. prepro leader peptide sequence of S. cerevisiae. When secreted from the yeast host cell, most of the leader peptide is processed from the fusion protein to yield a functional KI polypeptide (referred to herein as "PEP-1") having the amino acid sequence of SEQ ID NO:2 (see boxed region in FIG. 2).

Particularly preferred KI polypeptides useful in the methods and compositions described herein have a binding affinity for kallikrein that is on the order of 1000 times higher than that of aprotinin, which is currently approved for use in CABG procedures to reduce blood loss. The surprisingly high binding affinities of such KI polypeptides described herein indicate that such KI polypeptides exhibit a high degree of specificity for kallikrein to the exclusion of other molecular targets (see Table 1, below). Thus, use of such polypeptides according to the invention reduces much of the speculation as to the possible therapeutic targets in a patient. The lower degree of specificity exhibited by, for example, aprotinin, leads to possible pleiotropic side effects and ambiguity as to its therapeutic mechanism.

The polypeptides defined by, for example, SEQ ID NO:1 contain invariant positions, e.g., positions 5, 14, 30, 51 and 55 can be Cys only. Other positions such as, for example, positions 6, 7, 8, 9, 20, 24, 25, 26, 27, 28, 29, 41, 42, 44, 46, 47, 48, 49, 50, 52, 53 and 54 can be any amino acid (including non-naturally occurring amino acids). In a particularly preferred embodiment, one or more amino acids correspond to that of a native sequence (e.g., SEQ ID NO:32, see FIG. 3). In a preferred embodiment, at least one variable position is different from that of the native sequence. In yet another preferred embodiment, the amino acids can each be individually or collectively substituted by a conservative or non-conservative amino acid substitution. Conservative amino acid substitutions replace an amino acid with another amino acid of similar chemical structure and may have no affect on protein function. Non-conservative amino acid substitutions replace an amino acid with another amino acid of dissimilar chemical structure. Examples of conserved amino acid substitutions include, for example, Asn→Asp, Arg→Lys and Ser→Thr. In a preferred embodiment, 1, 2, 3, 4, 5, 6, 7, 8, 9, 10, 11, 12, 13, 14, 15, 16, 17, 18, 19, 20 and/or 21 of these amino acids can be independently or collectively, in any combination, selected to correspond to the corresponding position of SEQ ID NO:2.

Other positions, for example, positions 10, 11, 13, 15, 16, 17, 18, 19, 21, 22, 23, 31, 32, 34, 35, 39, 40, 43 and 45, can be any of a selected set of amino acids. Thus SEQ ID NO:1 defines a set of possible sequences. Each member of this set contains, for example, a cysteine at positions 5, 14, 30, 51 and 55, and any one of a specific set of amino acids at positions 10, 11, 13, 15, 16, 17, 18, 19, 221, 22, 23, 31, 32, 34, 35, 39, 40, 43 and 45. In a preferred embodiment, 1, 2, 3, 4, 5, 6, 7, 8, 9, 10, 11, 12, 13, 14, 15, 16, 17, 18 and/or 19 of these amino acids can be independently or collectively, in any combination, selected to correspond to the corresponding position of SEQ ID NO:2. The peptide preferably has at least 80%, at least 85%, at least 90% or at least 95% identity to SEQ ID NO:2.

Methods and Compositions

The present invention is also directed to methods for preventing or reducing ischemia. Preferred in the invention are methods for preventing or reducing perioperative blood loss and/or a systemic inflammatory response (SIR) in a patient, especially associated with cardiothoracic surgery. A method for treatment involves the administration of a KI polypeptide comprising a Kunitz domain. One embodiment of the method involves using a peptide containing an amino acid sequence of SEQ ID NO:1 that has an affinity for kallikrein that is approximately 1000-fold or more higher than that of a broad range serine protease, e.g., aprotinin, which is isolated from bovine lung and currently approved for use in CABG procedures (TRASYLOL®, Bayer Corporation Pharmaceutical Division, West Haven, Conn.).

Patients subjected to any of a number of surgical procedures, especially those involving extra-corporeal circulation, e.g., cardiothoracic surgery, such as, for example, CPB, and/or bone trauma, such as sternal split or hip replacement, are at risk for perioperative blood loss and inflammation. Contact of a patient's blood with the cut surfaces of bone or of CPB equipment is sufficient to activate one or several undesirable cascade responses, including a contact activation system (CAS), which can lead to extensive perioperative blood loss requiring immediate blood transfusion, as well as a systemic inflammatory response (SIR), which, in turn, can result in permanent damage to tissues and organs. While not desiring to be limited to any particular mechanism or theory, it appears that the blood loss that occurs associated with cardiothoracic surgery, e.g., CPB, as in a CABG procedure, probably results from extensive capillary leakage, which can result in significant loss of blood that must be replaced by immediate blood transfusion.

The methods described herein are useful for preventing or reducing various ischemias including, for example, perioperative blood loss and SIR in a patient subjected to a surgical procedure, and especially wherein the surgical procedure requires extra-corporeal circulation, e.g., cardiothoracic surgery, such as, for example, CPB. The methods of the invention are particularly useful for preventing or reducing perioperative blood loss and/or SIR in a patient subjected to a CABG procedure requiring CPB or other cardiac surgery.

Preferred compositions for medical use comprise a KI polypeptide described herein. Such compositions useful can further comprise one or more pharmaceutically acceptable buffers, carriers, and excipients, which can provide a desirable feature to the composition including, but not limited to, enhanced administration of the composition to a patient, enhanced circulating half-life of the KI polypeptide of the composition, enhanced compatibility of the composition with patient blood chemistry, enhanced storage of the composition, and/or enhanced efficacy of the composition upon administration to a patient. In addition to a KI polypeptide described herein, compositions can further comprise one or more other pharmaceutically active compounds that provide an additional prophylactic or therapeutic benefit to a patient of an invasive surgical procedure.

Compositions useful in the methods of the invention comprise any of the Kunitz domain polypeptides or KI polypeptides comprising such Kunitz domain polypeptides described herein. Particularly preferred are KI polypeptides comprising a Kunitz domain polypeptide having a 58-amino acid sequence of amino acids 3-60 of SEQ ID NO:2. An example of such a particularly preferred KI polypeptide useful in the methods and compositions of the invention is the PEP-1 KI polypeptide having the 60-amino acid sequence of SEQ ID NO:2. A nucleotide sequence encoding the amino acid sequence of SEQ ID NO:2 is provided in SEQ ID NO:3 (see, e.g., nucleotides 309-488 in FIG. 2). It is understood that based on the known genetic code, the invention also provides degenerate forms of the nucleotide sequence of SEQ ID NO:3 by simply substituting one or more of the known degenerate codons for each amino acid encoded by the nucleotide sequence. Nucleotides 7-180 of SEQ ID NO:3, and degenerate forms thereof, encode the non-naturally occurring Kunitz domain polypeptide having the 58-amino acid sequence of amino acids 3-60 of SEQ ID NO:2.

Any of a variety of nucleic acid molecules can comprise the nucleotide sequence of nucleotides 7-180 of SEQ ID NO:3, degenerate forms, and portions thereof, including but not limited to, recombinant phage genomes, recombinant mammalian viral vectors, recombinant insect viral vectors, yeast mini chromosomes, and various plasmids. Such plasmids include those used to clone and/or express such nucleotide coding sequences. Expression vectors provide a promoter, which can be operably linked to a particular nucleotide sequence and an appropriate host cell, which is able to transcribe the particular nucleotide coding sequence into a functional messenger RNA (mRNA) and also translate the mRNA into the corresponding polypeptide. A polypeptide so produced can then be isolated from the host cell. Nucleic acid molecules comprising a nucleic acid sequence encoding a Kunitz domain or KI polypeptide described herein can be made by standard nucleic acid synthesis methods, recombinant DNA methodologies, polymerase chain reaction (PCR) methods, and any combination thereof.

Perioperative Blood Loss and Reduced Heart Bloodflow

Due to the many advances in medicine, a number of highly invasive surgical procedures are carried out each day that result in blood loss, or place patients at a high risk for blood loss. Such patients must be carefully monitored to restore and maintain normal blood supply and hemostasis, and they may need blood transfusions. Surgical procedures that involve blood loss include those involving extra-corporeal circulation methods such as cardiothoracic surgery, e.g., CPB. In such methods, a patient's heart is stopped and the circulation, oxygenation, and maintenance of blood volume are carried out artificially using an extra-corporeal circuit and a synthetic membrane oxygenator. These techniques are commonly used during cardiac surgery. Additionally, it is apparent that surgery involving extensive trauma to bone, such as the sternal split necessary in CABG or hip replacement procedures, is also associated with activation of the CAS, which can result in a variety of disruptions in the blood and vasculature.

Atherosclerotic coronary artery disease (CAD) causes a narrowing of the lumen of one or several of the coronary arteries; this limits the flow of blood to the myocardium (i.e., the heart muscle) and can cause angina, heart failure, and myocardial infarcts. In the end stage of coronary artery atherosclerosis, the coronary circulation can be almost completely occluded, causing life threatening angina or heart failure, with a very high mortality. CABG procedures may be required to bridge the occluded blood vessel and restore blood to the heart; these are potentially life saving. CABG procedures are among the most invasive of surgeries in which one or more healthy veins or arteries are implanted to provide a "bypass" around the occluded area of the diseased vessel. CABG procedures carry with them a small but important perioperative risk, but they are very successful in providing patients with immediate relief from the mortality and morbidity of atherosclerotic cardiovascular disease. Despite these very encouraging results, repeat CABG procedures are frequently necessary, as indicated by a clear increase in the number of patients who eventually undergo second and even third procedures; the perioperative mortality and morbidity seen in primary CABG procedures is increased in these re-do procedures.

There have been improvements in minimally invasive surgical techniques for uncomplicated CAD. However, nearly all CABG procedures performed for valvular and/or congenital heart disease, heart transplantation, and major aortic procedures, are still carried out on patients supported by CPB. In CPB, large cannulae are inserted into the great vessels of a patient to permit mechanical pumping and oxygenation of the blood using a membrane oxygenator. The blood is returned to the patient without flowing through the lungs, which are hypoperfused during this procedure. The heart is stopped using a cardioplegic solution, the patient cooled to help prevent brain damage, and the peripheral circulating volume increased by an extracorporeal circuit, i.e., the CPB circuit, which requires "priming" with donor blood and saline mixtures are used to fill the extracorporeal circuit. CPB has been extensively used in a variety of procedures performed for nearly half a century with successful outcomes. The interaction between artificial surfaces, blood cells, blood proteins, damaged vascular endothelium, and extravascular tissues, such as bone, disturbs hemostasis and frequently activates the CAS, which, as noted above, can result in a variety of disruptions in the blood and vasculature. Such disruption leads to excess perioperative bleeding, which then requires immediate blood transfusion. A consequence of circulating whole blood through an extracorporeal circuit in CPB can also include the systemic inflammatory response (SIR), which is initiated by contact activation of the coagulation and complement systems. Indeed, much of the morbidity and mortality associated with seemingly mechanically successful CPB surgical procedures is the result of the effects of activating coagulation, fibrinolysis, or complement systems. Such activation can damage the pulmonary system, leading to adult respiratory distress syndrome (ARDS), impairment of kidney and splanchnic circulation, and induction of a general coagulopathy leading to blood loss and the need for transfusions. In addition to the dangers of perioperative blood loss, additional pathologies associated with SIR include neurocognitive deficits, stroke, renal failure, acute myocardial infarct, and cardiac tissue damage.

Blood transfusions also present a significant risk of infection and elevate the cost of CABG or other similar procedures that require CPB. In the absence of any pharmacological intervention, three to seven units of blood must typically be expended on a patient, even with excellent surgical techniques. Accordingly, there is considerable incentive for the development of new and improved pharmacologically effective compounds to reduce or prevent perioperative bleeding and SIR in patients subjected to CPB and CABG procedures.

Administration and Dosing Considerations for KI Polypeptides

KI polypeptides described herein can be administered to a patient before, during, and/or after a surgical procedure in a pharmaceutically acceptable composition. The term "pharmaceutically acceptable" composition refers to a non-toxic carrier or excipient that may be administered to a patient, together with a compound of this invention, and wherein the carrier or excipient not destroy the biological or pharmacological activity of the composition. KI polypeptides described herein can be administered locally or systemically by any suitable means for delivery of a kallikrein inhibitory amount of the KI polypeptides to a patient including but not limited to systemic administrations such as, for example, intravenous and inhalation. Parenteral administration is particularly preferred.

For parenteral administration, the polypeptides can be injected intravenously, intramuscularly, intraperitoneally, or subcutaneously. Intravenous administration is preferred. Typically, compositions for intravenous administration are solutions in sterile isotonic aqueous buffer. Other pharmaceutically acceptable carriers include, but are not limited to, sterile water, saline solution, and buffered saline (including buffers like phosphate or acetate), alcohol, vegetable oils, polyethylene glycols, gelatin, lactose, amylose, magnesium stearate, talc, silicic acid, paraffin, etc. Where necessary, the composition can also include a solubilizing agent and a local anaesthetic such as lidocaine to ease pain at the site of the injection, preservatives, stabilizers, wetting agents, emulsifiers, salts, lubricants, etc. as long as they do not react deleteriously with the active compounds. Similarly, the composition can comprise conventional excipients, e.g., pharmaceutically acceptable organic or inorganic carrier substances suitable for parenteral, enteral or intranasal application which do not deleteriously react with the active compounds. Generally, the ingredients will be supplied either separately or mixed together in unit dosage form, for example, as a dry lyophilized powder or water free concentrate in a hermetically sealed container such as an ampoule or sachette indicating the quantity of active agent in activity units. Where the composition is to be administered by infusion, it can be dispensed with an infusion bottle containing sterile pharmaceutical grade "water for injection" or saline. Where the composition is to be administered by injection, an ampoule of sterile water for injection or saline can be provided so that the ingredients can be mixed prior to administration.

Preferably, the methods of the invention comprise administering a KI polypeptide to a patient as an intravenous infusion according to any approved procedure. Thus, a KI polypeptide described herein can be administered to a patient subjected to a CABG procedure at the times similar to those currently used in approved protocols for administering aprotinin and in an amount necessary to provide a patient with a required number or concentration of kallikrein inhibitory units (KIU). According to the invention, a KI polypeptide described herein can also be administered to a patient in the immediate postoperative period, when bleeding abnormalities can occur as a consequence of downstream effects of SIR. For example, in a procedure involving CPB, a KI polypeptide described herein can be administered to a patient as an initial loading dose, e.g., an effective amount over the course of a convenient time, such as 10 minutes, prior to induction of anesthesia. Then, at induction of anesthesia, a second dose of KI polypeptide can be injected into the CPB priming fluid ("pump prime volume"). The patient can then be placed on a continuous and controlled intravenous infusion dose for the duration of the surgical procedure, and after the procedure if indicated.

Currently there are two regimens approved in the United States for administering aprotinin to a patient undergoing a CABG procedure (see, product label and insert for TRASYLOL®, Bayer Corporation Pharmaceutical Division, West Haven, Conn.). One such approved regimen uses a 2 million KIU intravenous loading dose, 2 million KIU into the pump prime volume, and 500,000 KIU per hour of surgery. Another approved regimen uses 1 million KIU intravenous loading dose, 1 million KIU into the pump prime volume, and 250,000 KIU per hour of surgery. As these regimens are based on KIU, the regimens are readily adapted to any KI polypeptide described herein once the specific activity and KIU of a particular KI polypeptide has been determined by standard assays. Owing to the enhanced binding affinity and inhibitory activity in representative KI polypeptides described herein relative to aprotinin, it is expected that such compositions and methods of the invention are likely to require fewer milligrams (mg) per patient to provide a patient with the required number or concentration of KIU.

Several considerations regarding dosing with a KI polypeptide in methods of the invention can be illustrated by way of example with the representative PEP-1 KI polypeptide of the invention having the amino sequence of SEQ ID NO:2 (molecular weight of 7,054 Daltons).

Table 1, below, provides a comparison of the affinity ($K_{i,app}$) of the PEP-1 KI polypeptide for kallikrein and eleven other known plasma proteases.

TABLE 1

| Protease Substrate | PEP-1 $K_{i,app}$ (pM) | Aprotinin $K_{i,app}$ (pM) |
|---|---|---|
| human plasma kallikrein | 44 | $3.0 \times 10^4$ |
| human urine kallikrein | $>1 \times 10^8$ | $4.0 \times 10^3$ |
| porcine pancreatic kallikrein | $2.7 \times 10^7$ | 550 |
| human C1r, activated | $>2.0 \times 10^8$ | $>1.0 \times 10^7$ |
| human C1s, activated | $>2.0 \times 10^7$ | $>1.0 \times 10^8$ |
| human plasma factor XIa | $1.0 \times 10^4$ | ND |
| human plasma factor XIIa | $>2.0 \times 10^7$ | $>1.0 \times 10^8$ |
| human plasmin | $1.4 \times 10^5$ | 894 |
| human pancreatic trypsin | $>2 \times 10^7$ | ND |
| human pancreatic chymotrypsin | $>2.0 \times 10^7$ | $7.3 \times 10^5$ |
| human neutrophil elastase | $>2.0 \times 10^7$ | $1.7 \times 10^6$ |
| human plasma thrombin | $>2.0 \times 10^7$ | $>1.0 \times 10^8$ |

ND=not determined

Clearly, the PEP-1 KI polypeptide is highly specific for human plasma kallikrein. Furthermore, the affinity ($K_{i,app}$) of PEP-1 for kallikrein is 1000 times higher than the affinity of aprotinin for kallikrein: the $K_{i,app}$ of PEP-1 for kallikrein is about 44 pM (Table 1), whereas the $K_{i,app}$ of aprotinin for kallikrein is 30,000 pM. Thus, a dose of PEP-1 could be approximately 1000 times lower than that used for aprotinin on a per mole basis. However, consideration of several other factors may provide a more accurate estimation of the dose of PEP-1 required in practice. Such factors include the amount of kallikrein activated during CPB in a particular patient, the concentration of kallikrein required to elicit an SIR, and the bioavailability and pharmacological distribution of PEP-1 in a patient. Nevertheless, use of a KI polypeptide in methods according to the invention and provided in doses currently approved for the use of aprotinin is still expected to provide significant improvements over the current use of the less specific, lower affinity, bovine aprotinin.

For example, the total amount of circulating prekallikrein in plasma is estimated at approximately 500 nM (Silverberg, M. et al., "The Contact System and Its Disorders," in Blood: Principles and Practice of Hematology, Handin, R. et al., eds., J B Lippincott Co., Philadelphia, 1995). If all of the prekallikrein were activated, then at least 500 nM of PEP-1 would be required for a stoichiometric inhibition of kallikrein. An individual having 5 liters of plasma would therefore require about 18 mg of PEP-1 to achieve a plasma concentration of 500 nM.

Another factor to consider is the threshold concentration of kallikrein required to induce a SIR in a patient. If the concentration of active kallikrein must be maintained below, e.g., 1 nM, then owing to its high affinity for kallikrein, PEP-1 offers a significant advantage over aprotinin in the amount of protein that would be required to inhibit SIR. In particular, a concentration of PEP-1 of 1 nM would inhibit 99.6% of kallikrein present at 1 nM (i.e., only 0.4 pM free kallikrein remaining in the blood), whereas, an aprotinin concentration of 1 nM would only inhibit 24.5% of the kallikrein present at 1 nM. For aprotinin to inhibit 99% of the kallikrein at 1 nM, an aprotinin concentration in the plasma of at least 3 $\mu M$ is required (i.e., 3000 times higher concentration than for PEP-1).

For a patient undergoing CPB, an initial clinical dose of PEP-1 can be estimated from a recommended dose regimen of aprotinin (1 $\times 10^6$ KIU) mentioned above. Aprotinin is reported in a package insert to have as specific inhibitory activity of 7143 KIU/mg determined using a dog blood pressure assay. Therefore, 1 $\times 10^6$ KIU of aprotinin is equivalent to 140 mg of aprotinin (i.e., 1 $\times 10^6$ KIU/7143 KIU/mg=140 mg of aprotinin). In a patient having a blood plasma volume of 5 liters, 140 mg corresponds to approximately 4.3 $\mu M$ aprotinin (molecular weight of aprotinin is 6512 Daltons). The specific activity of aprotinin in the standard inhibitory assay used for PEP-1 is 0.4 KIU/mg of polypeptide. A dose of 140 mg would correspond to a loading dose for aprotinin of 56 KIU (140 mg $\times$ 0.4 KIU/mg=56 KIU). In contrast, since the specific activity of the PEP-1 KI polypeptide is 10 KIU/mg in the standard inhibition assay, a dose of only 5.6 mg of PEP-1 would be required to provide the number of KIUs equivalent to 140 mg of aprotinin. In a patient with a plasma volume of 5 liters, this corresponds to about 160 nM PEP-1 (molecular weight of PEP-1 is 7054 Daltons), although a higher dose of the PEP-1 KI polypeptide can be required if all of the plasma kallikrein (500 nM) is activated and/or if this KI polypeptide is poorly distributed in a patient.

Furthermore, the KI polypeptides can be non-naturally occurring, and they can be produced synthetically or recombinantly, as noted above, thereby avoiding potential contamination of transmissible diseases that can arise during isolation of a protein from a natural animal source, such as in the case of aprotinin, which is isolated from bovine lung. Increasingly important to administrative and public acceptance of a treatment or pharmaceutical composition comprising a polypeptide is the avoidance of possible contamination with and transmission to human patients of various pathological agents. Of particular interest for the safety of proteins isolated from a bovine tissue is the elimination of the possible risk of exposure to viral mediated diseases, bacterial mediated diseases, and, especially, transmissible bovine spongiform encephalopathies.

As variants of the Kunitz domain 1 of the human LACI protein, fewer side effects are expected from administering the KI polypeptides to patients than for aprotinin, which is a bovine protein that is documented to cause anaphylactic and anaphylactoid responses in patients, especially in repeat administrations, such as second time CABG procedures. Additionally, the highly specific binding of the KI polypeptides described herein to kallikrein will effectively limit or eliminate the thrombotic tendencies observed with aprotinin, and reduce the problems observed with graft patency following CABG procedures.

The invention will be further described with reference to the following non-limiting examples. The teachings of all the patents, patent applications and all other publications and websites cited herein are incorporated by reference in their entirety.

EXEMPLIFICATION

Example 1

A Representative KI Polypeptide

A non-naturally occurring, KI polypeptide useful in the compositions and methods of the invention was identified as a kallikrein binding polypeptide displayed on a recombinant phage from a phage display library. PEP-1 has the following amino acid sequence: Glu Ala Met His Ser Phe Cys Ala Phe Lys Ala Asp Asp Gly Pro Cys Arg Ala Ala His Pro Arg Trp Phe Phe Asn Ile Phe Thr Arg Gln Cys Glu Glu Phe Ile Tyr Gly Gly Cys Glu Gly Asn Gln Asn Arg Phe Glu Ser Leu Glu Glu Cys Lys Lys Met Cys Thr Arg Asp (SEQ ID NO:2). The molecular weight of PEP-1 is 7,054 Daltons.

The nucleotide sequence (SEQ ID NO:3) encoding the PEP-1 amino acid sequence (SEQ ID NO:2), was derived from a peptide that was isolated and sequenced by standard methods determined from the recombinant phage DNA. PEP-1 was produced in amounts useful for further characterization as a recombinant protein in His4.sup.-phenotype host cells of yeast strain *Pichia pastoris*.

Example 2

Construction of a Recombinant Plasmid to Express KI Polypeptides

The initial plasmid, pHIL-D2, is ampicillin resistant and contains a wild-type allele of His4 from *P. pastoris*. The final DNA sequence comprising the coding sequence for the mat.alpha. Prepro-PEP-1 fusion protein in the recombinant expression plasmid pPIC-K503 is shown in FIG. 2. The DNA sequence of pHIL-D2 was modified to produce pPIC-K503, as follows:

1. The BstBI site in the 3' AOX1 region of pHIL-D2, located downstream of the His4 gene, was removed by partial restriction digestion, fill-in, and ligation, altering the sequence from TTCGAA (SEQ ID NO:23) to TTCGCGAA (SEQ ID NO:24). This modification was made to facilitate and direct the cloning of the expression cassette into the plasmid.

2. The AatII site bearing the bla gene located downstream of His4 was removed by restriction digestion, fill-in, and ligation modifying the sequence from GACGTC (SEQ ID NO:25) to GACGTACGTC (SEQ ID NO:26). This modification was made to facilitate the cloning of expression cassettes having AatII sites into the plasmid. The DNA encoding PEP-1 was synthesized based on the nucleotide sequence from the original kallikrein-binding display phage and consisted of 450 base pairs (bp). The final DNA sequence of the insert in the pHIL-D2 plasmid is flanked by a 5' AOX1 sequence and a 3' AOX1 sequence (portions of which are shown in FIG. 2) and encode a fusion protein comprising the mat.alpha. prepro signal peptide of *S. cerevisiae* fused to the structural coding sequence for the PEP-1 KI polypeptide. The signal peptide was added to facilitate the secretion of PEP-1 from the yeast host cells. The oligonucleotides to form the insert were synthesized and obtained commercially (Genesis Labs, The Woodlands, Tex.), and the insert was generated by polymerase chain reaction (PCR). The linked synthetic DNA encoding the mat.alpha. prepro/PEP-1 fusion protein was then incorporated by ligation into the modified pHIL-D2 plasmid between the BstBI and EcoRI sites.

The ligation products were used to transform *Escherichia coli* strain XL1 Blue. A PCR assay was used to screen *E. coli* transformants for the desired plasmid construct. DNA from cell extracts was amplified by PCR using primers containing the 5' AOX1 and 3' AOX1 sequences (see above and FIG. 2). PCR products of the correct number of base pairs were sequenced. In addition, approximately 20-50 bp on either side of the cloning sites were sequenced, and the predicted sequence was obtained. The final DNA sequence of the insert in the pHIL-D2 plasmid (to yield plasmid pPIC-K503) is shown in FIG. 2 along with portions of flanking 5' and 3' AOX1 sequences and corresponding amino acid sequence of the fusion protein comprising the mat.alpha. prepro signal peptide of *S. cerevisiae* fused to the structural coding sequence for the PEP-1 KI polypeptide. A transformant with the desired expression plasmid construct, plasmid pPIC-K503, was selected for preparing yeast cell lines for routine production of PEP-1.

Example 3

Manufacture of PEP-1 from Recombinant Yeast Cell Line

Spheroplasts of *P. pastoris* GS115 having the His4.sup.-phenotype were transformed with the expression plasmid pPIC-K503 (above) following linearization of the plasmid at the SacI site and homologous recombination of the plasmid DNA into the host 5' AOX1 locus. The phenotype of the production strain is His4.sup.+. The entire plasmid was inserted into the 5' AOX1 genomic sequence of the yeast.

Isolates from the transformation were screened for growth in the absence of exogenous histidine with methanol as the sole carbon source. Greater than 95% of the transformants retained the wild-type ability to grow with methanol as the sole carbon source, thereby demonstrating that the plasmid had been inserted into the host genome by homologous recombination rather than transplacement. These transformants did not require exogenous histidine for growth, thereby demonstrating that the plasmid had integrated into the host genome. Selected colonies were cloned. Small culture expression studies were performed to identify clones secreting the highest levels of active PEP-1 into the culture medium. PEP-1 secretion levels in clarified culture supernatant solutions were quantified for PEP-1 levels by sodium dodecyl sulfate polyacrylamide gel electrophoresis (SDS-PAGE) and evaluated for kallikrein inhibition. A yeast clone was selected for PEP-1 production based on its high level of PEP-1 expression among cultures sampled.

Master and working cell banks of *P. pastoris* producing PEP-1 were prepared commercially (MDS Pharma Services, Bothell, Wash.). A standard production of PEP-1 in yeast comprised three steps as follows: (1) preparation of the seed culture, (2) fermentation, and (3) recovery of the culture.

The seed culture step consisted of the inoculation of six flasks (300 mL each) containing sterile inoculum broth (yeast nitrogen base, potassium phosphate, and glycerol, pH=5) with the contents of a single vial of a working cell bank of *P. pastoris* producing PEP-1. Flasks were inoculated in an orbital shaker (300 rpm) for approximately 13 hours at 30.degree. C.+-0.2.degree. C.

Fermentations were performed in a closed 100 liter Braun fermenter filled with sterile broth. Each fermentation was initiated with the transfer of the contents of the six seed culture flasks to the fermenter. After approximately 24 hours, the glycerol in the fermenter became exhausted and additional glycerol was added for approximately 8 additional hours.

A mixed feed phase, which lasted approximately 83 hours, was then initiated by the addition of a glycerol and methanol feed. At the end of this time, the fermentation was terminated, and the fermenter contents were diluted with purified water. The purification and processing of PEP-1 consisted of five steps as follows: (1) expanded bed chromatography, (2) cation exchange chromatography, (3) hydrophobic interaction chromatography (HIC), (4) ultrafiltration and diafiltration, and (5) final filtration and packaging.

The initial purification step consisted of expanded bed chromatography. The diluted fermenter culture was applied to the equilibrated column packed with Streamline SP resin (Amersham Pharmacia Streamline 200 chromatography column, Amersham Pharmacia, Piscataway, N.J.). The column was then washed (50 mM acetic acid, pH=3.0-3.5) in an up-flow mode to flush the yeast cells from the expanded bed. The top adaptor was raised above the expanded bed enhance washing. The flow was stopped and the bed was allowed to settle. The adaptor was moved down so that it was slightly above the settled bed. The direction of the flow was reversed. The effluent was collected. Washing was continued in a downward mode using 50 mM sodium acetate, pH 4.0. The effluent was collected. PEP-1 was eluted from the column using 50 mM sodium acetate, pH 6.0. The eluate was collected in a 50 liter container. The eluate was then filtered through a 0.22.mu. filter into a clean container located in the purification site. Additional samples were collected for the determination of PEP-1 concentration. A cation exchange chromatography step was then performed using the filtered eluate from the expanded bed column. PEP-1 was eluted from the column using 15 mM trisodium citrate, pH 6.2.

Additional proteins were removed from the PEP-1 preparation by hydrophobic interaction chromatography (HIC). Prior to HIC, the eluate from the cation exchange column was diluted with ammonium sulfate. The eluate was applied to the column, and the PEP-1 was eluted using ammonium sulfate (0.572 M) in potassium phosphate (100 mM), pH 7.0. The eluate was collected in fractions based on A280 values. All fractions were collected into sterile, pre-weighed PETG bottles.

Selected fractions were pooled into a clean container. The pool was concentrated by ultrafiltration. The concentrated PEP-1 preparation was immediately diafiltered against ten volumes of PBS, pH 7.0.

A final filtration step was performed prior to packaging in order to minimize the bioburden in the bulk PEP-1. The bulk solution was filtered through a 0.22.mu. filter and collected into a sterile, pre-weighed PETG bottle. A sample was removed for lot release testing. The remainder of the bulk was dispensed aseptically into sterile PETG bottles and stored at −20.degree. C.

Example 4

Kallikrein Inhibition Assay

A kinetic test was used to measure inhibitory activity of KI polypeptides, such as PEP-1. The kinetic assay measures fluorescence following kallikrein-mediated cleavage of a substrate, prolylphenylalanylarginyl amino methyl coumarin. A known amount of kallikrein was incubated with a serially diluted KI polypeptide reference standard or serially diluted KI polypeptide test samples, in a suitable reaction buffer on a microtiter plate. Each sample was run in triplicate. The substrate solution was added, and the plate read immediately using an excitation wavelength of 360 nm and an emission wavelength of 460 nm. At least two each of the reference standard and sample curves were required to have an R-squared value of 0.95 to be considered valid.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method for reducing blood loss in a patient comprising administering to the patient a composition comprising a pharmaceutically acceptable carrier and a polypeptide comprising the amino acid sequence: Xaa1 Xaa2 Xaa3 Xaa4 Cys Xaa6 Xaa7 Xaa8 Xaa9 Xaa10 Xaa11 Gly Xaa13 Cys Xaa15 Xaa16 Xaa17 Xaa18 Xaa19 Xaa20 Xaa21 Xaa22 Xaa23 Xaa24 Xaa25 Xaa26 Xaa27 Xaa28 Xaa29 Cys Xaa31 Xaa32 Phe Xaa34 Xaa35 Gly Gly Cys Xaa39 Xaa40 Xaa41 Xaa42 Xaa43 Xaa44 Xaa45 Xaa46 Xaa47 Xaa48 Xaa49 Xaa50 Cys Xaa52 Xaa53 Xaa54 Cys Xaa56 Xaa57 Xaa58 (SEQ ID NO:1), wherein Xaa1, Xaa2, Xaa3, Xaa4, Xaa56, Xaa57 or Xaa58 are each individually any amino acid or absent;

Xaa6, Xaa7, Xaa8, Xaa9, Xaa20, Xaa24, Xaa25, Xaa26, Xaa27, Xaa28, Xaa29, Xaa41, Xaa42, Xaa44, Xaa46, Xaa47, Xaa48, Xaa49, Xaa50, Xaa52, Xaa53 and Xaa54 are each any amino acid;

Xaa10 is Asp;

Xaa11 is an amino acid selected from the group consisting of: Asp, Gly, Ser, Val, Asn, Ile, Ala and Thr;

Xaa13 is an amino acid selected from the group consisting of: Arg, His, Pro, Asn, Ser, Thr, Ala, Gly, Lys and Gln;

Xaa15 is an amino acid selected from the group consisting of: Arg, Lys, Ala, Ser, Gly, Met, Asn and Gln;

Xaa16 is an amino acid selected from the group consisting of: Ala, Gly, Ser, Asp and Asn;

Xaa17 is an amino acid selected from the group consisting of: Ala, Asn, Ser, Ile, Gly, Val, Gln and Thr;

Xaa18 is an amino acid selected from the group consisting of: His, Leu, Gln and Ala;

Xaa19 is an amino acid selected from the group consisting of: Pro, Gln, Len, Asn and Ile;

Xaa21 is an amino acid selected from the group consisting of: Trp, Phe, Tyr, His and Ile;

Xaa22 is an amino acid selected from the group consisting of: Tyr and Phe;

Xaa23 is an amino acid selected from the group consisting of: Tyr and Phe;

Xaa31 is an amino acid selected from the group consisting of: Glu, Asp, Gln, Asn, Ser, Ala, Val, Leu, Ile and Thr;

Xaa32 is an amino acid selected from the group consisting of: Gln, Gln, Asp Asn, Pro, Thr, Leu, Ser, Ala, Gly and Val;

Xaa34 is an amino acid selected from the group consisting of: Asn, and Leu;

Xaa35 is an amino acid selected from the group consisting of: Tyr, Trp and Phe;

Xaa39 is an amino acid selected from the group consisting of: Glu, Gly, Ala, Ser and Asp;

Xaa40 is an amino acid selected from the group consisting of: Gly and Ala;

Xaa43 is an amino acid selected from the group consisting of: Asn and Gly;

Xaa45 is an amino acid selected from the group consisting of: Phe and Tyr;

and wherein the polypeptide inhibits kallikrein.

2. The method of claim 1, wherein Xaa13 is Pro, Xaa15 is Arg, Xaa16 is Ala, Xaa17 is Ala, Xaa18 is His, and Xaa19 is Pro.

3. The method of claim 1, wherein Xaa21 is Trp.

4. The method of claim 1, wherein Xaa31 is Glu.

5. The method of claim 1, wherein Xaa32 is Glu.

6. The method of claim 1, wherein Xaa34 is Ile.

7. The method of claim 1, wherein Xaa35 is Tyr.

8. The method of claim 1, wherein Xaa39 is Glu.

9. The method of claim 1, wherein the polypeptide comprises a flanking sequence of one to six amino acids in length.

10. The method of claim 1, wherein the administering is performed intravenous parenterally, or subcutaneously.

11. The method of claim 1, wherein the pharmaceutically acceptable carrier is a sterile isotonic aqueous buffer, or a sterile saline solution.

12. The method of claim 1, wherein a surgical procedure has been performed on the patient.

13. The method of claim 12, wherein the surgical procedure is a cardiothoracic surgery.

14. The method of claim 13, wherein the cardiothoracic surgery is cardiopulmonary bypass or coronary artery bypass grafting.

* * * * *